United States Patent [19]

Furutachi et al.

[11] Patent Number: 4,865,963
[45] Date of Patent: Sep. 12, 1989

[54] SILVER HALIDE COLOR PHOTOGRAPHIC MATERIALS CONTAINING NOVEL MAGENTA COUPLER

[75] Inventors: Nobuo Furutachi; Tadahisa Sato; Seiki Sakanoue; Akio Mitsui; Minoru Sakai; Masakazu Morigaki; Hidetoshi Kobayashi; Nobuo Sakai; Kiyoshi Nakazyo; Takeshi Hirose; Toshio Kawagishi, all of Kanagawa, Japan

[73] Assignee: Fuji Photo Film Co., Ltd., Kanagawa, Japan

[21] Appl. No.: 913,792

[22] Filed: Sep. 30, 1986

[30] Foreign Application Priority Data

| Sep. 30, 1985 | [JP] | Japan | 60-217314 |
| Oct. 3, 1985 | [JP] | Japan | 60-219192 |
| Oct. 9, 1985 | [JP] | Japan | 60-223810 |
| Oct. 18, 1985 | [JP] | Japan | 60-232634 |
| Oct. 19, 1985 | [JP] | Japan | 60-233869 |
| Oct. 19, 1985 | [JP] | Japan | 60-233870 |
| Oct. 20, 1985 | [JP] | Japan | 60-233879 |
| Oct. 20, 1985 | [JP] | Japan | 60-233880 |
| Oct. 21, 1985 | [JP] | Japan | 60-235009 |
| Oct. 25, 1985 | [JP] | Japan | 60-239049 |
| Nov. 1, 1985 | [JP] | Japan | 60-245926 |
| Nov. 5, 1985 | [JP] | Japan | 60-247804 |
| Nov. 5, 1985 | [JP] | Japan | 60-247805 |
| Jan. 22, 1986 | [JP] | Japan | 61-10240 |
| Jan. 22, 1986 | [JP] | Japan | 61-10241 |
| Jan. 22, 1986 | [JP] | Japan | 61-10242 |
| Jan. 22, 1986 | [JP] | Japan | 61-10243 |
| Jan. 22, 1986 | [JP] | Japan | 61-10244 |

[51] Int. Cl.⁴ ............ G03C 1/08; G03C 7/26; G03C 7/32
[52] U.S. Cl. .................. 430/558; 430/386; 430/387; 430/505; 430/512; 430/544; 430/545; 430/546; 430/548; 430/549; 430/551
[58] Field of Search ............... 430/558, 505, 512, 386, 430/387, 548, 546, 551, 549, 544, 545

[56] References Cited

U.S. PATENT DOCUMENTS 4,585,732 4/1986 Kawagishi et al. ............ 430/558
4,590,153 5/1986 Kawagishi et al. ............ 430/551
4,639,413 1/1987 Kawagishi et al. ............ 430/546

FOREIGN PATENT DOCUMENTS 0143570 11/1984 European Pat. Off. .
0218266 4/1985 European Pat. Off. .
0173256 8/1985 European Pat. Off. .
0176804 9/1985 European Pat. Off. .

OTHER PUBLICATIONS

Research Disclosure #17643, "Photographic Silver Halide, etc.", pp. 22-26.

Primary Examiner—Paul R. Michl
Assistant Examiner—Patrick A. Doody
Attorney, Agent, or Firm—Sughrue, Mion, Zinn, Macpeak & Seas

[57] ABSTRACT

A silver halide color photographic material comprising a support having thereon at least one silver halide emulsion layer, said silver halide emulsion layer containing a pyrazoloazole series magenta coupler represented by general formula [I]

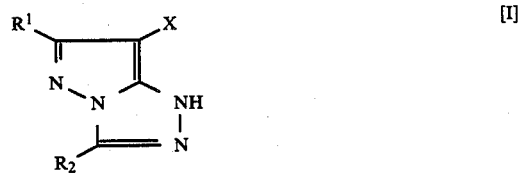

wherein, $R^1$ and $R^2$ each represents a hydrogen atom or a substituent; and X represents a hydrogen atom or a releasing group which is released at the reaction with the oxidation product of an aromatic primary amine developing agent; at least one of said $R^1$ and $R^2$ is an alkyl group having a secondary or tertiary carbon atom directly bonded to the skeleton, at least one of said $R_1$ and $R_2$ is a sulfonamidoalkyl group or a sulfamoylalkyl group; and the magenta coupler may form a dimer or more polymer at the position of said $R^1$, $R^2$ or X.

By the combined use of high boiling point organic solvent and ultraviolet absorbent, light fastness and coloring property are markedly improved.

13 Claims, No Drawings

SILVER HALIDE COLOR PHOTOGRAPHIC MATERIALS CONTAINING NOVEL MAGENTA COUPLER

FIELD OF THE INVENTION

This invention relates to a silver halide color photographic material and more particularly to a silver halide color photographic material having improved coloring property and light fastness of color images.

BACKGROUND OF THE INVENTION

Pyrazoloazole type couplers give dyes having less unnecessary spectral absorption at about 430 n.m. induced from dyes formed by coupling with the oxidation product of paraphenylenediamine as compared to conventional 5-pyrazolone couplers and hence various pyrazoloazole type couplers have been proposed for improving the color reproduction of color light-sensitive materials.

For example, there are proposed pyrazolobenzimidazole skeletons described in U.S. Pat. Nos. 3,061,432, 3,369,897, etc., 1H-pyrazolo[3,2-c][1,2,4]triazole skeletons described in U.S. Pat. No. 3,725,067, etc., 1H-imidazo[1,2-b]pyrazole skeletons described in U.S. Pat. No. 4,500,630, etc., 1H-pyrazolo[1,5-b][1,2,4]triazole skeletons described in U.S. Pat. No. 4,540,654, etc., and 1H-pyrazolo[1,5-b]tetrazole skeletons described in Japanese Patent Application (OPI) No. 33,552/85 (the term "OPI" as used herein means as "unexamined published Japanese patent application").

The azomethine dyes induced from the pyrazoloazole couplers having these skeletons surely have less unnecessary absorption near 430 n.m. and show sharp foot cut of-the characteristic curve at a long wavelength side, which are preferably for color reproduction, but they are yet insufficient for color photographic materials since the coupling speed of the couplers with the oxidation product of a developing agent is slow and also the light fastness of color images formed is low.

SUMMARY OF THE INVENTION

The object of this invention is to provide a silver halide color photographic material using pyrazoloazole series coupler(s) showing improved coloring property by increasing the coupling speed with the oxidation product of a developing agent, giving color images having improved fastness, in particular light fastness, and further capable of increasing the sensitivity of the photographic material.

As the result of making various investigations on pyrazoloazole skeletons and linkage groups of linking a non-diffusible group for attaining the above object, it has been discovered that the pyrazoloazole series magenta coupler represented by following general formula [I] is a coupler having excellent properties meeting the aforesaid object and also the aforesaid object can be attained by the silver halide color photographic material containing these couplers:

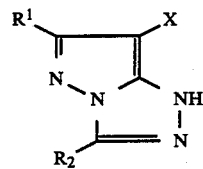

[I]

wherein, $R^1$ and $R^2$ each represents a hydrogen atom or a substituent; and X represents a hydrogen atom or a group releasing at reaction with the oxidation product of an aromatic primary amine developing agent; at least one of said $R^1$ and $R^2$ is an alkyl group having a secondary or tertiary carbon atom directly bonded to the skeleton; at least one of said $R^1$ and $R^2$ represents a sulfonamidoalkyl group or a sulfamoylalkyl group, and said coupler may form a dimer or a more polymer at $R^1$, $R^2$, or X.

DETAILED DESCRIPTION OF THE INVENTION

Then, the substituents, $R^1$, $R^2$, and X of general formula [I] described above are explained in detail.

$R^1$ and $R^2$ each represents a hydrogen atom, a halogen atom (e.g., a chlorine atom, a bromine atom, etc.,), an alkyl group (e.g., a methyl group, a propyl group, an i-propyl group, a cyclopentyl group, a cyclohexyl group, a 1-ethylpentyl group, a t-butyl group, a trifluoromethyl group, a tridecyl group, a 3-(2,4-di-t-amylphenoxy)propyl group, an allyl group, a 2-dodecyloxyethyl group, 3-(2-butoxy-5-t-octylphenylsulfonyl)propyl group, 3-phenoxypropyl group, a 2-hexylsulfonylethyl group, a benzyl group, etc.,), an aryl group (e.g., a phenyl group, a 4-t-butylphenyl group, a 2,4-di-t-amylphenyl group, a 4-tetradecanamidophenyl group, etc.,), a heterocyclic group preferably being 5- or 6-membered ring or condensed ring thereof containing at least one atom or O, N, and S, (e.g., a 2-furyl group, a 2-thienyl group a 2-pyrimidinyl group, a 2-benzothiazolyl group, etc.,), a cyano group, an alkoxy group (e.g., a methoxy group, an ethoxy group, a 2-methoxyethoxy group, a 2-phenoxyethoxy group, a 2-dodecyloxyethoxy group, a 2-methanesulfonylethoxy group, etc.,), an aryloxy group (e.g., a phenoxy group, a 2-methylphenoxy group, a 4-t-butylphenoxy group, etc.,), a heterocyclic oxy group preferably being 5- or 6-membered ring or condensed ring thereof containing at least one atom of O, N, and S (e.g., a 2-benzimidazolyloxy group, etc.,), an acyloxy group (e.g., an acetoxy group, a hexadecanoyloxy group, etc.,), a carbamoyloxy group (e.g., an N-phenylcarbamoyloxy group, an N-ethylcarbamoyloxy group, etc.,), a silyloxy group (e.g., a trimethylsilyloxy group, etc.,), a sulfonyloxy group (e.g., a dodecylsulfonyloxy group, etc.,), an acylamino group (e.g., an acetamido group, a benzamido group, a tetradecanamido group, an α-(2,4-di-t-amylphenoxy)-butylamido group, a γ-(3-t-butyl-4-hydroxyphenoxy)-butylamido group, an α-{4-(4-hydroxyphenylsulfonyl)-phenoxy}decanamido group, etc.,), an anilino group (e.g., a phenylamino group, a 2-chloroanilino group, a 2-chloro-5-tetradecanamidoanilino group, a 2-chloro-5-dodecyloxycarbonylanilino group, an N-acetylanilino group, a 2-chloro-5-{α-(3-t-butyl-4-hydroxyphenoxy)-dodecanamidoanilino group, etc.,), a ureido group (e.g., a phenylureido group, a methylureido group, an N,N-dibutylureido group, etc.,), an imido group (e.g., an N-succinimido group, a 3-benzylhydantoinyl group, a 4-(2-ethylhexanoylamino)phthalimido group, etc.,), a sulfamoylamino group (e.g., an N,N-dipropylsulfamoylamino group, a N-methyl-N-decylsulfamoylamino group, etc.),an alkylthio group (e.g., a methylthio group, an octylthio group, a tetradecylthio group, a 2-phenoxyethylthio group, a 3-phenoxypropylthio group, a 3-(4-t-butylphenoxy)propylthio group, etc.,), an arylthio group (e.g., a phenylthio group, a 2-butoxy-5-t-octylphenylthio group, a 3-pentadecylphenylthio group, a 2-carboxyphenylthio group, a 4-tetradecanamidophanylthio group, etc.,), a heterocyclic thio group preferably being 5- or or 6-membered ring containing at least one atom of O, S, and N (e.g., a 2-benzothiazolylthio group, etc.,), an alkoxycarbonylamino group (e.g., a methoxycarbonylamino group, a tetradecyloxycarbonylamino group, etc.,), an aryloxycarbonylamino group (e.g., a phenoxycarbonylamino group, a 2,4-di-tert-butylphenoxycarbonylamino group, etc.,), a sulfonamido group (e.g., a methanesulfonamido group, a hexadecanesulfonamido group, a benzenesulfonamido group, a p-toluenesulfonamido group, an octandecansulfonamido group, a 2-methyloxy-5-t-butylbenzenesulfonamido group, etc.,), a carbamoyl group (e.g., an N-ethylcarbamoyl group, an N,N-dibutylcarbamoyl group, an N-(2-dodecyloxyethyl)carbamoyl group, an N-methyl-N-dodecylcarbamoyl group, an N- 3-(2,4-di-tert-amylphenoxy)propyl carbamoyl group, etc.,), an acyl group (e.g., an acetyl group, a (2,4-di-tert-amylphenoxy)acetyl group, a benzoyl group, etc.,), a sulfamoyl group (e.g., an N-ethylsulfamoyl group, an N,N-dipropylsulfamoyl group, an N-(2-dodecyloxyethyl)sulfamoyl group, an N-ethyl-N-dodecylsulfamoyl group, an N,N-diethylsulfamoyl group, etc.,), a sulfonyl group (e.g., a methanesulfonyl group, an octanesulfonyl group, a benzenesulfonyl group, a toluenesulfonyl group, etc.,), a sulfinyl group (e.g., an octanesulfinyl group, a dodecylsulfinyl group, a phenylsulfinyl group, etc.,), an alkoxycarbonyl group (e.g., a methoxycarbonyl group, a butyloxycarbonyl group, a dodecylcarbonyl group, an octadecylcarbonyl group, etc.,), an aryloxycarbonyl group (e.g., a phenyloxycarbonyl group, or a 3-pentadecyloxycarbonyl group, etc.,).

The alkyl group, alkoxy group, alkylthio group, alkoxycarbonylamino group and alkoxycarbonyl group represented by $R^1$ and $R^2$ as is described above each preferably contains 1 to 38 carbon atoms and further may have substituents. The aryl group, aryloxy group, anilino group, arylthio group and aryloxycarbonyl amino group represented by $R^1$ and $R^2$ as is described above each preferably includes a phenyl group or a naphthyl group and further may have substituents.

The groups represented by $R^1$ and $R^2$ may have further substituents.

Also, X represents a hydrogen atom; a halogen atom (e.g., a chlorine atom, a bromine atom, an iodine atom, etc.,); a carboxy group; a group bonded with an oxygen atom preferably including an acyloxy group, an oxazolyloxy group, a pyruvinyloxy group, an alkenyloxy group, an aryloxy group, an arylalkoxycarbonyloxy group, an alkoxy group, a tetrazolyloxy group, a thiazolyloxy group and derivatives Therefore (e.g., an acetoxy group, a propanoyloxy group, a benzoyloxy group, a 2,4-dichlorobenzoyloxy group, an ethoxyoxazolyloxy group, pyruvinyloxygroup, a cinnamoyloxy group, a phenoxy group, a 4-cyanophenoxy group, a 4-metanesulfonamidophenoxy group, a 4-methanesulfonylphenoxy group, an α-naphthoxy group, a 3-pentadecylphenoxy group, a benzyloxycarbonyloxy group, an ethoxy group, a 2-cyanbethoxy group, a benzyloxy group, a 2-phenethyloxy group, a 2-phenoxyethoxy group, a 5-phenyltetrazolyloxy group, a 2-benzothiazolyloxy group, etc.,); a group bonded with a nitrogen atom preferably including a sulfonamido group, a piperidyl group, a carbonamido group, an ureido group, an amino group, an oxazolidinyl group, a hydantionyl group, an isothiazolyl group, a pyridinyl group, an imidazolyl group, a pyrazolyl group, a triazolyl group, a tetrazolyl group (e.g., a benzenesulfonamido group, an N-ethyltoluenesulfonamido group, a heptafluorobutaneamido group, a 2,3,4,5,6-pentafluorobenzamido group, an octanesulfonamido group, a p-cyanophenylureido group, an N,N-diethylsulfamoylamino group, a 1-piperidyl group, a 5,5-diemthyl-2,4-dioxo-3-oxazolidinyl group, a benzyl-ethoxy-3-hydantoinyl group, a 2N-1,1-dioxo-3(2H)-oxo-1,2-benzoisothiazolyl group, a 2-oxo-1,2-dihydro-1-pyridinyl group, an imidazolyl group, a pyrazolyl group, a 3,5-diethyl-1,2,4-triazol-1-yl, 5- or 6-bromo-benzotriazol-1-yl group, a 5-methyl-1,2,3,4-triazole-1-yl group, a benzimidazolyl group, a 3-benzyl-1-hydanoinyl group, a 1-benzyl 5-hexadecyloxy-3-hydanoinyl group, a 5-methyl-1-tetrazolyl group etc.,); a arylazo group preferably including a phenylazo group, a naphthylazo group and derivatives thereof (e.g., a 4-methoxyphenylazo group, a 4-pivaloylaminophenylazo group, a 2-naphthylazo group, a 3-methyl-4-hydroxyphenylazo group, etc.,) or a group bonded by a sulfur atom preferably including an arylthio group, an alkylthio group, a triazolylthio group, a tetrazolylthio group, a thiazolylthio group, a thiophenylthio group and derivatives thereof (e.g., a phenylthio group, a 2-carboxyphenylthio group, a 2-butoxy-5-t-octylphenylthio group, a 4-methanesulfonylphenylthio group, a 4-octanesulfonamidophenylthio group, a 2-butoxyphenylthio group, a 2-(2-hexanesulfonylethyl)-5-tert-octylphenylthio group, a benzylthio group, a 2-cyanoethylthio group, a 1-ethoxycarbonyltridecylthio group, a 5-phenyl-2,3,4,5-tetrazolylthio group, a 2-benzothiazolyl group, a 2-dodecylthio-5-thiophenylthio group, a 2-phenyl-3-dodecyl-1,2,4-triazolyl-5-thio group, etc.,).

The substituents, sulfonamidoalkyl group and sulfamoylalkyl group are explained in detail.

The sulfonamidoalkyl group and the sulfamoylalkyl group are represented by following general formulae [I-1] and [I-2], respectively.

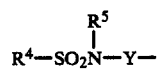

[I-1]

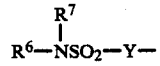

[I-2]

wherein, $R^4$ and $R^6$ each represents an alkyl group, an aryl group or a heterocyclic group, (preferably comprising 5- or 6-membered ring or condensed ring thereof containing at least one atom of O, S and N atoms), which may have at least one substituent selected from the groups represented by $R^1$ and $R^2$ disclosed above.

$R^5$ and $R^7$ each preferably represents a hydrogen atom, an alkyl group, an aryl group or a heterocyclic group (preferably comprising 5- or 6-membered ring or condensed ring thereof containing at least one atom of O, S and N atoms), which may have at least one substituents selected from the groups represented by $R^1$ and $R^2$ disclosed above. $R^5$ and $R^7$ each more preferably represents a hydrogen atom. Y represents an alkylene group The alkylene group preferably contains 1 to 10 carbon atoms in a straight-chain moiety thereof and may have at least one substituent selected from the same groups as those represented by $R^1$ and $R^2$ disclosed above.

Most preferred alkylene group includes one having a secondary or tertiary carbon atom directly bonded to the skeleton. The total carbon atoms of $R^4$, $R^5$ and Y, or $R^6$, $R^7$ and Y preferably are 2 to 65. Preferred examples of the aryl group represented by $R^4$, $R^5$, $R^6$ and $R^7$ include a phenyl group and a naphthyl group and their derivatives. Preferred examples of the heterocyclic group include the same as those disclosed above for the groups represented by $R^1$ and $R^2$.

When at least one of said $R^1$ and $R^2$ is a sulfonamidoalkyl group or a sulfamoylalkyl group, wherein the carbon atom directly bonded to the skeleton is secondary or tertiary in the alkyl moiety of the sulfonamidoalkyl group or the sulfamoylalkyl group, the other substituent of $R^2$ or $R^1$ may be a hydrogen atom or any groups represented by $R^1$ and $R^2$.

In Y, the term "secondary or tertiary carbon atom directly bonded to the skeleton" means a carbon atom substituted with one carbon atom for one hydrogen atom of a methylene group directly bonded to the skeleton, or substituted with two carbon atoms for two hydrogen atoms of the methylene group, respectively.

When $R^1$, $R^2$, or X in general formula [I] is a divalent group to form a bis-form, $R^1$ and $R^2$ each represents a substituted or unsubstituted alkylene group (e.g., a methylene group, an ethylene group, a 1,10-decylene group, —$CH_2CH_2$—O—$CH_2CH_2$—, etc.), a substituted or unsubstituted phenylene group (e.g., a 1,4-phenylene group, a 1,3-phenylene group,

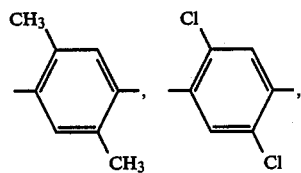

etc.), —NHCO—$R_3$—CONH— group (wherein $R^3$ represents a substituted or unsubstituted alkylene or phenylene group), such as, for example, —NHCOCH$_2$CH$_2$CONH—,

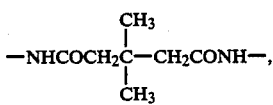

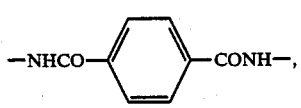

etc., or —S—$R^{3'}$—S— group (wherein, $R^{3'}$ represents a substituted or unsubstituted alkylene group), such as, for example, —S—CH$_2$CH$_2$—S—,

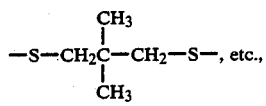

and X represents a group formed by converting the above-described univalent group about X to a divalent group at a proper position of X.

As described above, the magenta coupler represented by general formula [I] above may form a dimer or more oligomer and the oligomer in this invention means a compound having two or more moieties shown by general formula [I] and a bis-compound and a polymer coupler are included in the oligomers. Now, the polymer coupler in this invention may be a homopolymer composed of a monomer (preferably a vinyl group-having monomer, hereinafter, such a monomer is referred to as a vinyl monomer) including the moiety represented by general formula [I] described above or may be a copolymer of the monomer and a non-coloring ethylenical monomer which does not cause coupling with the oxidation product of an aromatic amine developing agent.

When the coupler represented by general formula [I] described above is included in a vinyl monomer as described above, the linkage group shown by $R^1$, $R^2$, or X includes a group selected from a substituted or unsubstituted alkylene group (e.g., a methylene group, an ethylene group, a 1,10-decylene group, —CH$_2$CH$_2$OCH$_2$CH$_2$—, etc.), a substituted unsubstituted phenylene group (e.g., a 1,4-phenylene group, a 1,3-phenylene group,

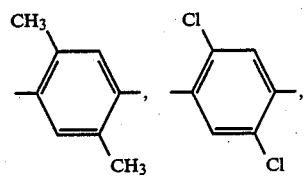

etc.), —NHCO—, —CONH—, —O—, and —OCO—, or combination of them, the combination of the groups includes, for example,

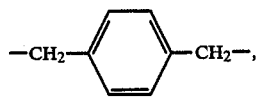

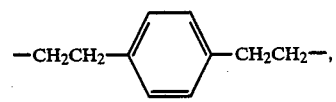

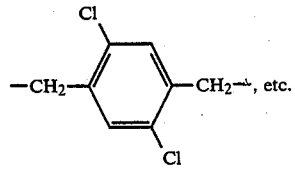

The alkylene group of the linkage group represented by $R^7$, $R^2$ or X which is included in a dimer or a more polymer preferably contains 1 to 38 carbon atoms and substituent of the linkage group above described preferably includes an alkyl group, an alkoxy group, an aryl group, a halogen atom, etc.

Examples of the preferred linkage group are as follows.

—NHCO—, —CH₂CH₂—,

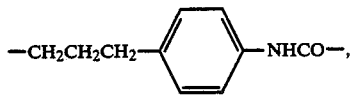

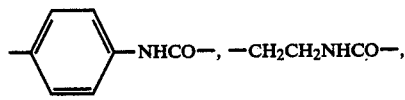

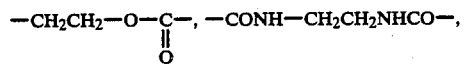

—CH₂CH₂O—CH₂CH₂—NHCO—,

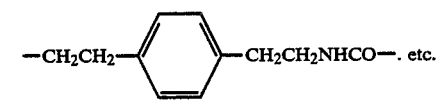

In addition, the vinyl group may have substituent(s) in addition to the moiety shown by general formula [I] and examples of the preferred substituent are a chlorine atom, or a lower alkyl group having 1 to 4 carbon atoms (e.g., a methyl group, an ethyl group, etc.,).

As described above, the monomer including the moiety represented by general formula [I] may form a copolymer with a non-coloring ethylenical monomer which does not cause coupling with the oxidation product of an aromatic primary amine developing agent.

Examples of the non-coloring ethylenical monomer which does not cause coupling with the oxidation product of an aromatic primary amine developing agent are acrylic acid, α-chloroacrylic acid, α-alkylacrylic acid (e.g., methacrylic acid, etc.,), the esters or amides induced from these acrylic acids (e.g., acrylamide, n-butylacrylamide, t-butylacrylamide, diacetoneacrylamide, methacrylamide, methylacrylate, ethylacrylate, n-propyl acrylate, n-butyl acrylate, t-butyl acrylate, iso-butyl acrylate, 2-ethylhexyl acrylate, n-octyl acrylate, lauryl acrylate, methyl methacrylate, ethyl methacrylate, n-butyl methacrylate, and β-hydroxy methacrylate), methylenedibisacrylamide, vinyl esters (e.g., vinyl acetate, vinyl propionate, and vinyl laurate, ), acrylonitrile, methacrylonitrile, aromatic vinyl compounds (e.g., styrene and the derivatives thereof, vinyltoluene, divinylbenzene, vinylacetophenone, and sulfostyrene), itaconic acid, citraconic acid, crotonic aicd, vinylidene chloride, vinyl alkyl ethers (e.g., vinyl ethyl ether, etc.,), maleic acid, maleic anhdyride, maleic acid ester, N-vinyl-2-pyrrolidone, N-vinylpyridine, and 2- or 4-vinylpyridine. The above-described monomers can be used solely or as a combination thereof. Examples of the combination are a combination of n-butyl acrylate and methyl acrylate, a combination of styrene and methacrylic acid, a combination of methacyrlic acid and acrylamide, and a combination of methyl acrylate and diacetonacrylamide.

As well known in the field of polymer couplers, the non-coloring ethylenically unsaturated monomer which is copolymerized with a solid water-insoluble monomer coupler can be selected so that the physical properties and/or chemical properties of the copolymer formed thereby, such as the solubility, the compatibility with a binder for photographic colloid composition such as gelatin, the flexibility, the heat stability, etc., obtain good influences.

The polymer coupler for use in this invention may be water soluble or water insoluble and in these polymer couplers, polymer coupler latex is particularly preferred.

The magenta coupler used in this invention is used in an amount of $1 \times 10^{-3}$ mol to 1 mol, preferably $3 \times 10^{-3}$ mol to $3 \times 10^{-1}$ mol per mol of light-sensitive silver halide.

Then, typical examples of the magenta coupler and the polymer coupler for use in this invention are illustrated below but the invention is not limited to these compounds.

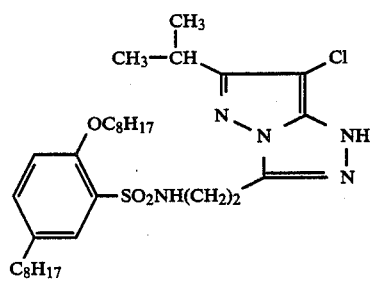

(M-1)

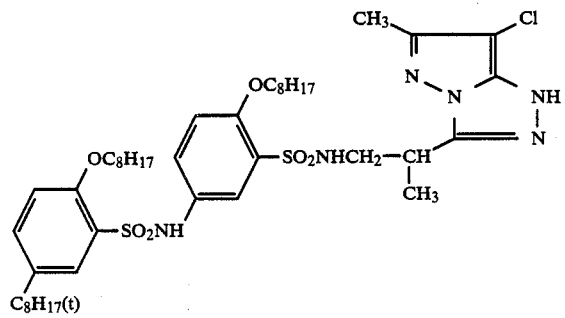

(M-2)

-continued
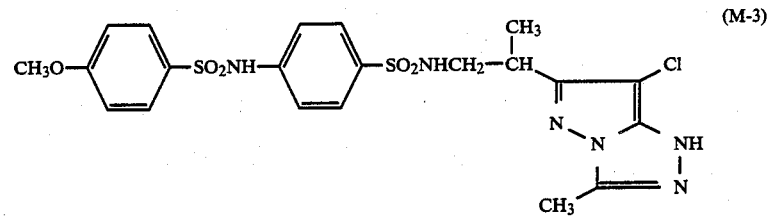
(M-3)
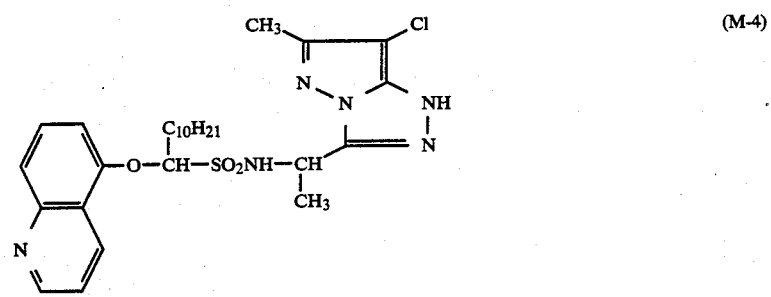
(M-4)
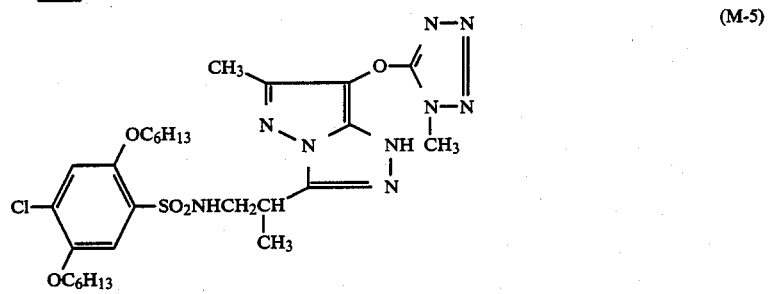
(M-5)
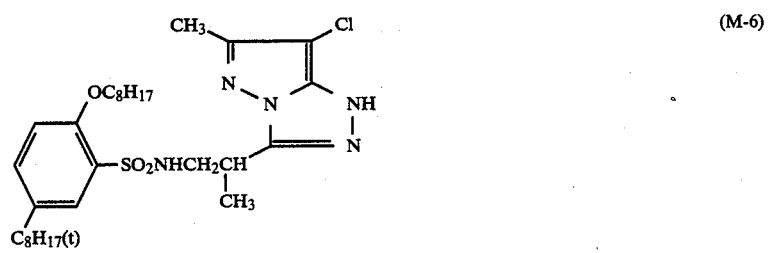
(M-6)
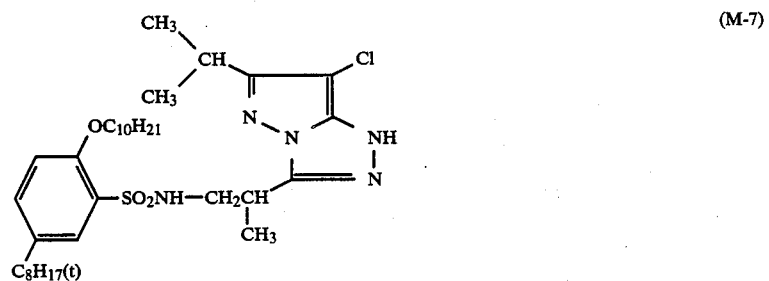
(M-7)
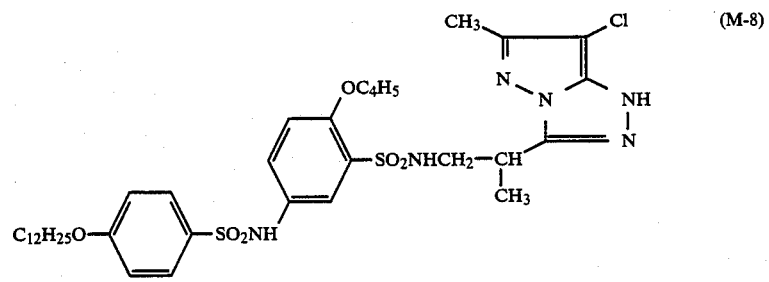
(M-8)

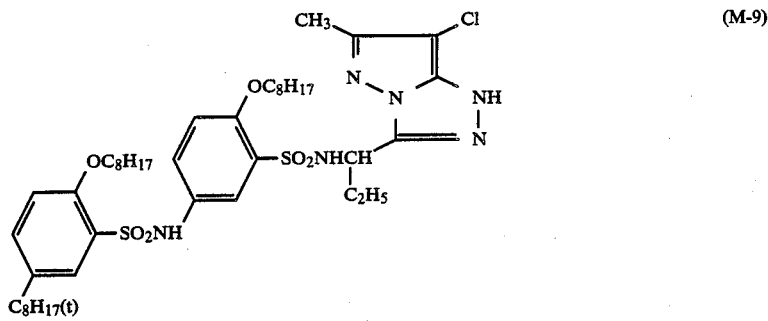
(M-9)
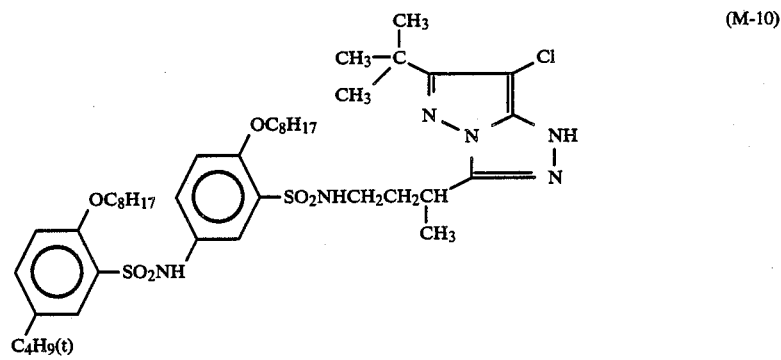
(M-10)
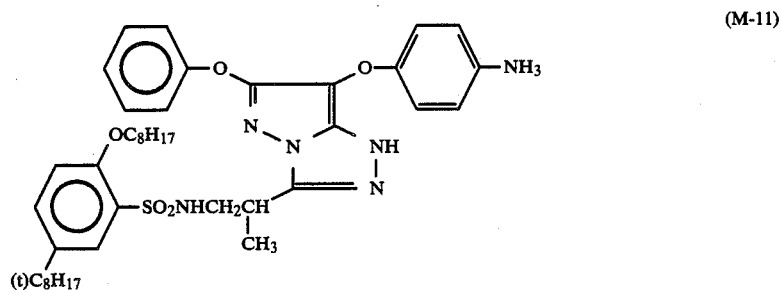
(M-11)
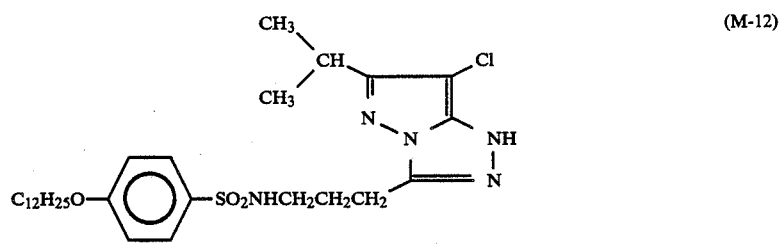
(M-12)
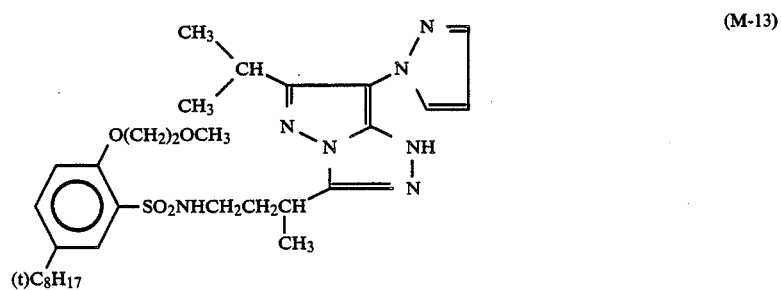
(M-13)

(M-14)

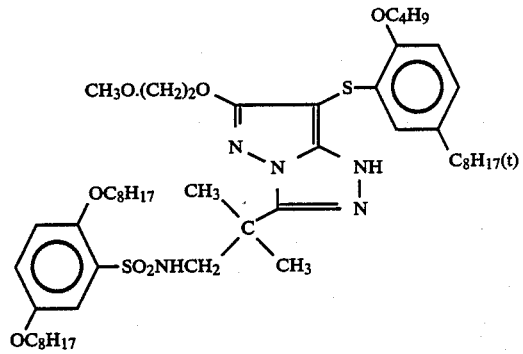

(M-15)

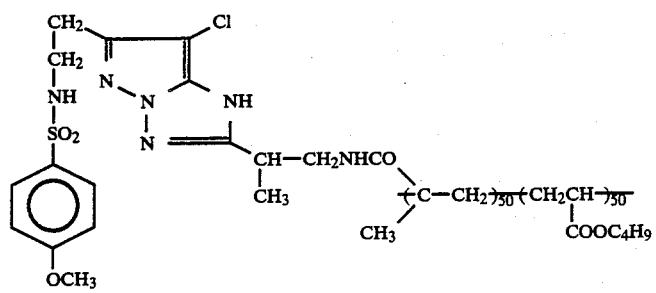

(M-16)

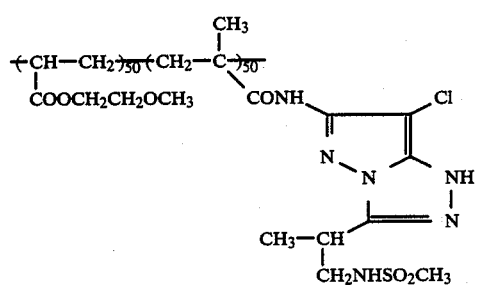

The coupler skeletons for use in this invention can by synthesized according to the methods described in U.S. Pat. No. 3,725,067 and also the moieties of the non-diffusible groups synthesized according to the methods described in Japanese Patent Application (OPI) No. 65,246/86. Synthesis examples of the typical couplers are shown below.

Synthesis Example [Synthesis Example of Compound (M-2)]:

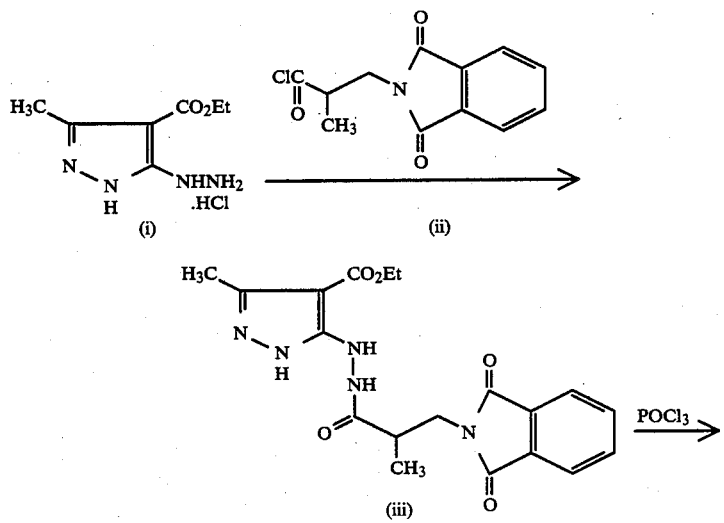

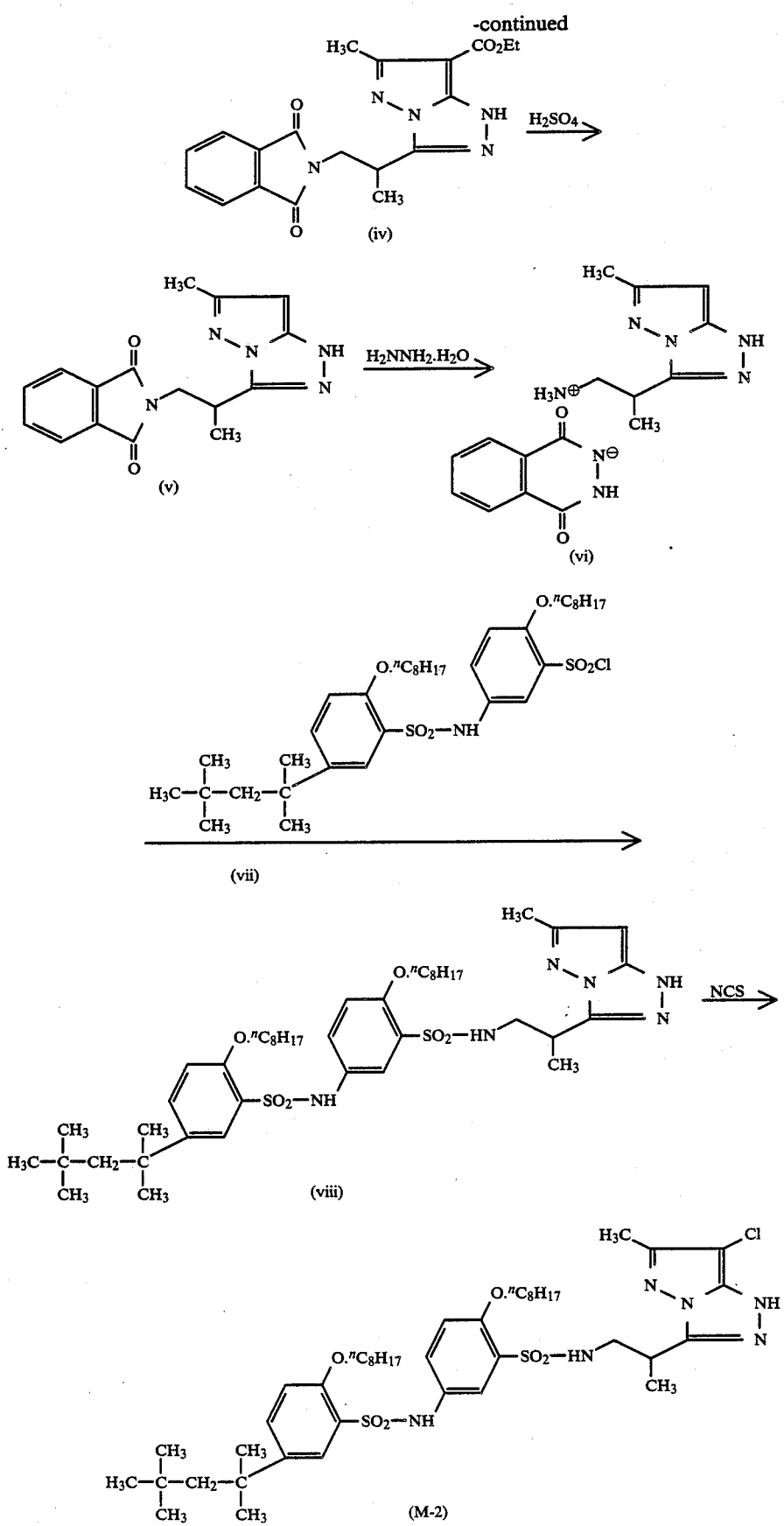

(1) Synthesis of Compound (iii):

To 54.2 g (0.25 mol) of Compound (i) described above was added 324 ml of pyridine and with stirring the mixture under ice-cooling, 68.0 g (0.28 mol) of Compound (ii) described above was added thereto little by little. The mixture was stirred while allowing to increase the temperature to room temperature and thereafter, the mixture was refluxed for 30 minutes. After allowing to cool the mixture, 324 ml of water was added thereto extracted with ethyl acetate. The ethyl acetate phase thus obtained was allowed to stand overnight to desposit crystals, which were collected by filtration under suction, sufficiently washed with water and the ethyl acetate to provide 69.0 g (0.18 mol) of desired compound (iii) shown above at a yield of 69%.

Melting Point: 235.5° C.

NMR (DMSO-$d_6$): $\delta$=10.06 (s, 1H), 8.87 (d, J=6.0 Hz, 1H), 7.85 (s, 4H), 4.5-6.5 (br, s, 1H), 4.20 (q, J=7.0 Hz, 2H), 3.68 (d, J=7.5 Hz, 2H), 2.7-3.0 (m, 1H), 2.30 (s, 3H), 1.28 (t, J=7.0 Hz, 3H), 1.05 (d, 7.5 Hz, 3H).

(2) Synthesis of Compound (iv):

To 29,0 g (0.073 mol) of Compound (iii) shown above was added 580 ml of ethylene chloride and while stirring the mixture, 16.9 ml (0.18 mol) of phosphorus oxychloride was dropwise to the mixture. Thereafter, the mixture was stirred under refluxing for 5 hours and after allowing to cool, the reaction mixture thus formed was extracted with ethyl acetate. The ethyl acetate phase thus formed was washed thrice with an aqueous saturated sodium chloride solution, dried by anhydrous sodium sulfate, and concentrated. The residue thus obtained was dissolved in 200 ml of methanol and while stirring the solution at room temperature, 2 ml of triethylamine was added dropwise to the solution. Thereafter, the mixture was concentrated under reduced pressure until the amount of the residue became 100 ml. The residue was stirred under ice-cooling and the crystals thus deposited were collected by filtration under suction to provide 18.3 g (0.048 mol) of desired compound (iv) with a yield of 66%. Melting point: 193.8° C.

NMR (CDCl$_3$): $\delta$: 7.6-7.9 (m, 4H), 4.33 (q, J=7.5 Hz, 2H), 3.7-4.5(m, 1H), 3.7-4.5 (br, 1H), 3.83 (d, J=10 Hz, 2H), 2.30 (s, 3H), 1.65 (d, J=6 Hz, 3H), 1.43 (t, J=7.5 Hz, 3H).

(3) Synthesis of Compound (v):

To 16.1 g (0.042 mol) of Compound (iv) obtained above was added 80 ml of sulfuric acid and after stirring the mixture for 90 minutes at bath temperature of 110° to 120° C., the mixture was cooled to room temperature. To the reaction mixture was added 500 ml of ice-water and after neutralizing the mixture with sodium hydrogencarbonate, the reaction mixture was extracted with ethyl acetate. The ethyl acetate phase was dried by anhydrous sodium sulfate, concentrated under reduced pressure until the amount of the residue became 100 ml, and the crystals thus deposited were collected by filtration under suction to provide 5.70 g (0.018 mol) of desired compound (V) with a yield of 44%.

Melting point: 189.0° C.

NMR (CDCl$_3$): $\delta$: 7.0-7.9 (m, 5H), 5.29 (s, 1H), 3.4-4.3 (m, 3H), 2.10 (s, 3H), 1.12 (d, J=6.9 Hz, 3H).

(4) Synthesis of Compound (vi):

To 5.20 g (0.017 mol) of Compound (v) obtained above was added 50 ml of isopropyl alcohol followed by stirring at room temperature. To the mixture was added dropwise 1.35 ml (0.022 mol) of hydrazine hydrate (80%) and then the mixture was stirred under refluxing for 7 hours. The reaction mixture was ice-cooled and after filtering off insoluble matters, the filtrate thus obtained was concentrated under reduced pressure. The residue thus obtained was used for the synthesis of Compound (viii) shown below without being purified.

(5) Synthesis of Compound (viii):

To Compound (vi) obtained above was added 15 ml of N,N-dimethylacetamide and then a solution of 9.41 g (0.013 mol) of Compound (vii) dissolved in 15 ml of N,N-dimethylacetamide was added dropwise to the mixture under water-cooling. Furthermore, 1.86 ml (0.013 mol) of triethylamine was added dropwise to the mixture followed by stirring as it was for 15 minutes, and after adding thereto 20 ml of water, the product was extracted with ethyl acetate. The ethyl acetate phase thus obtained was washed with an aqueous saturated sodium chloride solution, dried using anhydrous sodium sulfate, and then concentrated under reduced pressure. The residue formed was dissolved in 10 ml of ethyl acetate, 150 ml of hexane was added to the solution, and after allowing to stand the mixture overnight at room temperature, the crystals thus deposited were collected by filtrated under suction to provide 9.10 g (0.11 mol) of desired compound (VIII) with a yield of 64%.

Melting point: 97.5° C.

NMR (CDCl$_3$): $\delta$:=10.5 (br s, 1H), 6.5-7.9 (m, 6H), 5.6 (brs, 1H), 5.1 (s, 1H), 4.20 (t, J=6.0 Hz, 2H), 3.90 (t, J=6.0 Hz, 2H), 3.0-3.6 (m, 3H), 2.30 s, 3H), 0.7-2.1 (m, 41H), 0.53 (s, 9H).

(6) Synthesis of Compound (M-2):

16.2 g (0.019 mol) of Compound (viii) obtained above was added 500 ml of ethyl acetate and while stirring at room temperature, 2.56 g (0.019 mol) of N-chlorosuccinic acid imide was added thereto. The reaction mixture was washed with an aqueous saturated sodium chloride solution, dried by anhydrous sodium sulfate, and concentrated under reduced pressure. The residue thus obtained was purified by chromatography to provide 16.8 g of oily desired compound (M-2) with a yield of 100%.

NMR (CDCl$_3$): $\delta$:=10.5 (br s, 1H), 6.5-7.9 (m, 6H), 5.6 (br, s, 1H), 4.18 (t, J=6.0 Hz, 2H), 3.90 (t, J=6.0 Hz, 2H), 3.0-3.6 (m, 3H), 2.33 (s, 3H), 0.7-2.1 (m, 41H), 0.53 (s, 9H).

The couplers of general formula [I] for use in this invention can be added to a silver halide emulsion as a solution in a high-boiling point organic solvent having boiling point (1 atm.) of about 175° C. or more.

For example, it is preferred to use at least one kind of high-boiling point organic solvents shown by following general formula [II], [III] [IV], or [V], having a dielectric constant of at least 4.00 (25° C., 10 KHz) and a viscosity of at least 20 c.p. (25° C.):

[II]

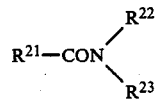

[III]

-continued

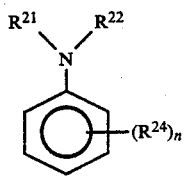

$$R^{21}-O-R^{22} \quad [V]$$

wherein, $R^{21}$, $R^{22}$, and $R^{23}$ each represents a substituted or unsubstituted alkyl group, a substituted on unsubstituted cycloalkyl group, a substituted or unsubstituted alkenyl group, a substituted or unsubstituted aryl group, or a substituted or unsubstituted heterocyclic group; said $R^{21}$ and $R^{22}$ in general formula [V] described above may form a condensed ring; $R^{24}$ represents $R^{21}$, —$OR^{21}$, or —$SR^{21}$; and n represents an integer of 1 to 5; when n is 2 or more, plural $R^{24}$s may be the same or different. The heterocyclic group preferably comprises 5- or 6-membered ring or a condensed ring thereof containing at least one atom of S, N and O.

Then, the high-boiling organic solvents represented by above-described general formula [II], [III], [IV] or [V] are explained in detail. The high-boiling point organic solvents shown by the above formulae wherein the sum of the carbon atoms of $R^{21}$, $R^{22}$, $R^{23}$, or $R^{24}$ is at least about 8 in each general formulae [II] to [V] the dielectric constant is at least 4,00 (25° C., 10 KHz), and the viscosity is at least 20 (25° C.) are particularly preferred.

In addition, the dielectric constant can be measured by a transformer bridge method (TRS-10, trade name, made by Ando Denki K.K.), and the viscosity can be measured by a cone plate-type rotational viscometer (VICONIS EMD, trade name, made by Tokyo Keiki K.K.).

The groups shown by $R^{21}$, $R^{22}$, and $R^{23}$ in general formula [II], [III], [IV], or [V] described above may have substituent(s) as described above and the substituent may be a group having at least one linkage group selected from

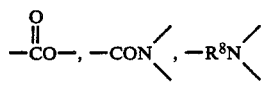

(wherein, $R^8$ represents a 1 to 4 valent group formed by removing hydrogen atom from a phenyl group), and —O—.

In general formula [II], [III], [IV], or [V], the alkyl group shown by $R^{21}$, $R^{22}$, $R^{23}$, or $R^{24}$ is a straight chain or branched alkyl group such as, for example, a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, an eicosyl group, etc.

The allowable substituents for these alkyl groups are explained be referring to the case of general formula [II] described above. As such a substituent, there are, for example, a halogen atom, a cycloalkyl group, an aryl group, an ester group, etc., and examples of such substituted alkyl groups are halogen (F, Cl, Br, etc.)-substituted alkyl groups (e.g., —$C_2HF_4$, —$C_5H_3F_8$, —$C_9H_3F_{16}$, —$C_2H_4Cl$, —$C_3H_6Cl$, —$C_3H_5C_2$, —$C_3H_5ClBr$, —$C_3H_5Br$, etc.), substituted cycloalkyl groups (e.g.,

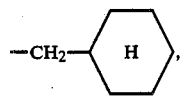

etc.), substituted aryl groups (e.g.,

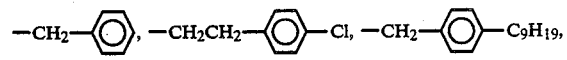

etc.), substituents giving the esters of dibasic acid together with the —COO— group of general formula II (e.g.,

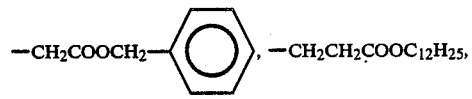

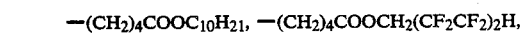

substituents giving lactic acid esters, etc., (e.g.,

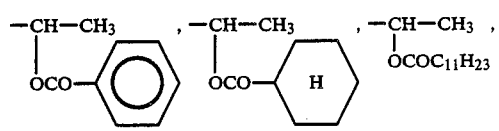

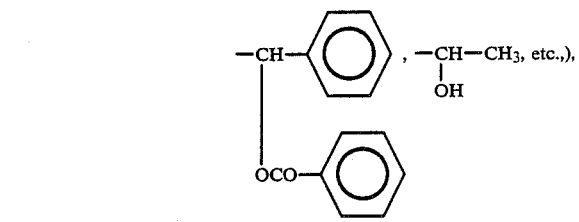

substituents giving citric acid esters

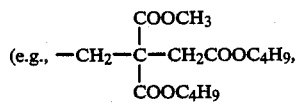

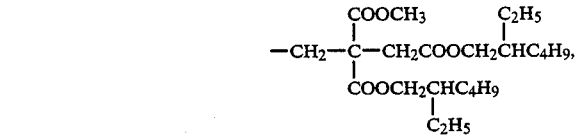

etc.), substituents giving malic acid esters (e.g., —$CH_2CH(OH)COOC_6H_{13}$, —$CH_2CH(OH)COOC_{12}H_{25}$, etc.), substituents giving tartaric acid esters, etc., (e.g., —$CH(OH)CH(OH)COOC_8H_{17}$,

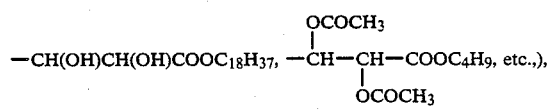

—CH$_2$—C(OH)—CH$_2$COOC$_8$H$_{17}$, etc.
|
COOC$_8$H$_{17}$

The alkyl groups in general formulae [IV] and [V] may have the substituent(s) as in the above-described alkyl group in general formula [II]. Furthermore, in general formula [V], R$^{21}$ and R$^{22}$ may contain an oxirane, an oxolane or an oxane ring forming a condensed ring.

The cycloalkyl group shown by R$^{21}$, R$^{22}$, R$^{23}$ or R$^{24}$ is, for example,

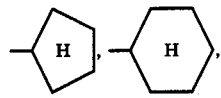

etc., and substituted cyclohexyl group preferably includes those having an alkoxycarbonyl group, an aryloxycarbonyl group or derivatives thereof such as

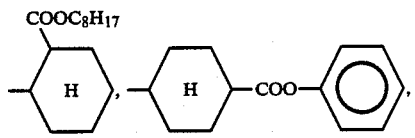

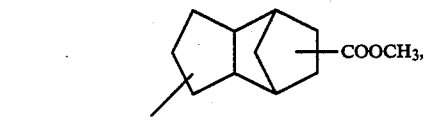

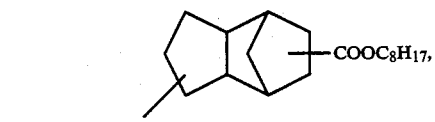

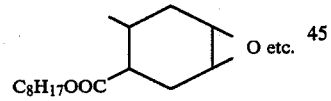 O etc.

Examples of the aryl group shown by R$^{21}$, R$^{22}$, R$^{23}$ or R$^{24}$ are

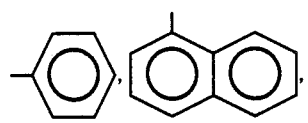

etc. The substituent for the aryl group preferably includes an alkoxycarbonyl group, a cycloalkoxy carbonyl group, an aryloxy carbonyl group, an alkoxyalkoxy carbonyl group, a halogen atom (e.g., Cl, Br, F, etc.), a halogen-substituted alkoxy carbonyl group, an alkenyloxy carbonyl group, an alkyl group, an alkoxy group or groups derived from them. Examples of substituted aryl group are those providing esters of phthalic acid, isophthalic acid, terephthalic acid, trimellitic acid, etc., such as

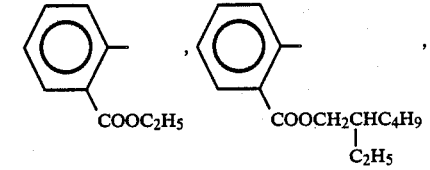

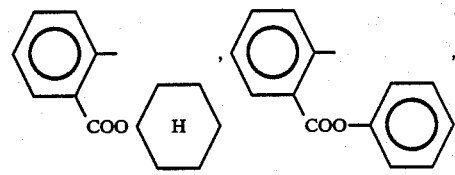

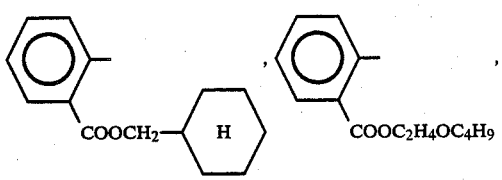

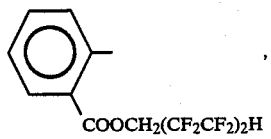

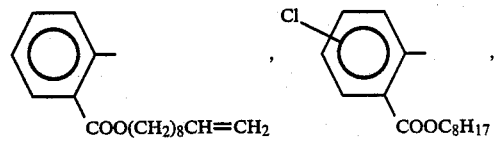

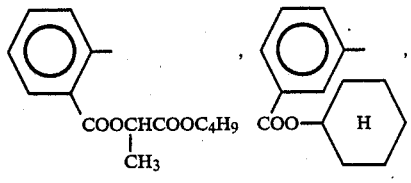

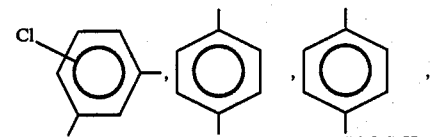

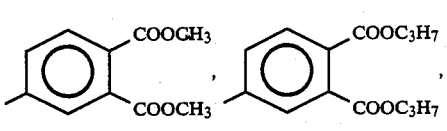

and substituted benzoic acid esters such as

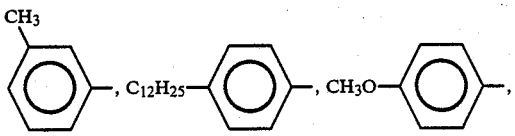

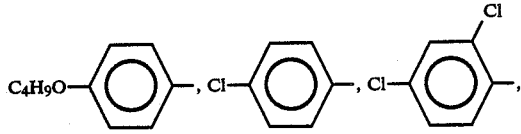

Also, examples of the alkenyl group shown by $R^{21}$, $R^{22}$, $R^{23}$ or $R^{24}$ are $-C_4H_7$, $-C_5H_9$, $-C_6H_{11}$, $-C_7H_{13}$, $-C_8H_{15}$, $-C_{10}H_{19}$, $-C_{12}H_{23}$, $-C_{18}H_{35}$, etc., and substituted alkenyl group are, preferably alkenyl groups substituted with a halogen atom (e.g., fluorine, chlorine, bromine, etc.,), an alkoxy group, a cycloalkoxy group, an aryl group, an aryloxy group, an acyloxy group, an alkyl group, an alkenyl group or groups derived from them. Substituted alkenyl groups are, for example, alkenyl groups substituted by $-Cl$, $-F$, $-Br$, $-OC_8H_{17}$, $-OC_{12}H_{25}$,

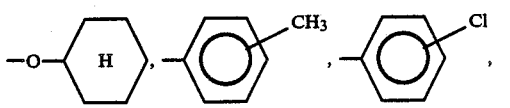

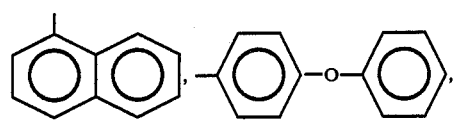

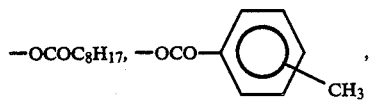

$-C_8H_{15}$, $-C_{12}H_{23}$, etc., such as

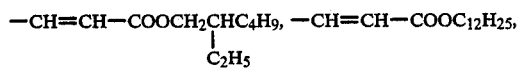

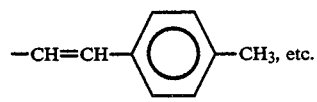

It is desirable that the high-boiling point organic solvents shown by general formula [II], [III], [IV] or [V] in which $R^{21}$, $R^{22}$, $R^{23}$, or $R^{24}$ is, preferably, substituted as described above has a dielectric constant of at least 4.00 at 25° C. and the viscosity is at least 20 c.p. at 25° C. It is astonishing that when the dielectric constant of a high-boiling organic solvent is at least 4.00 (25° C.) and the viscosity thereof is at least 20 c.p. (25° C.), in this invention can be further improved and also the color reproducibility and the light fastness thereof can be improved. The reason of obtaining such effects has not yet been clarified but it is considered a high-boiling point organic solvent having high dielectric constant largely receives a color developing agent and a high-boiling point solvent having a viscosity higher than an intermediate value makes weak some bad action of the coupler(s) in oil drops and silver halide.

The amount of the high-boiling point organic solvent shown by general formula [II], [III], [IV], or [V] for use in this invention may be optionally selected according to the kind and using amount of the magenta coupler shown by general formula [I] described above but it is preferred that the ratio of the high-boiling point organic solvent/the magenta coupler is from 0.05 to 20 by weight ratio.

Also, the high-boiling point organic solvent shown by general formula [II], [III], [IV], or [V] for use in this invention may be used solely or as a mixture thereof or together with other conventional high-boiling point organic solvents in the range capable of attaining the objects of this invention. Examples of these conventional high-boiling point organic solvents which can be used together with the high-boiling point organic solvent(s) shown by the above general formulae are preferably phosphoric acid ester series solvents such as tricresyl phosphate, tri-2-ethylhexyl phosphate, 7-methyloctyl phosphate, tricyclohexyl phosphate, etc., phenolic solvents such as 2,5-di-tert-amylphenol, 2,5-sec-amylphenol, etc.

Then, specific examples of the high-boiling organic solvents shown by general formula [II], [III], [IV], and [V] are illustrated below but the invention is not limited by these examples.

| Compound No. | Structural Formula | Dielectric constant 25° C., (10 KHz) | Viscosity 25° C., cp |
|---|---|---|---|
| P-1 | ⌬(COOC₄H₉(n))₂ | 6.45 | 20.3 |
| P-2 | ⌬(COOC₄H₉(iso))₂ | 6.52 | 34.0 |
| P-3 | ⌬(COOC₅H₁₁(n))₂ | 5.91 | 21.0 |

-continued

| Compound No. | Structural Formula | Dielectric constant 25° C., (10 KHz) | Viscosity 25° C., cp |
|---|---|---|---|
| P-4 | Benzene-1,2-dicarboxylic acid bis(2-ethylbutyl) ester: C₆H₄(COOCH₂CH(C₂H₅)C₂H₅)₂ | 5.88 | 44.2 |
| P-5 | Benzene-1,2-dicarboxylic acid bis(cyclohexyl) ester | 6.45 (Supercooling Liquid) | Solid (mp 58~65° C.) |
| P-6 | Benzene-1,2-dicarboxylic acid bis(cyclohexylmethyl) ester | 6.44 | 35.2 |
| P-7 | Benzene-1,2-dicarboxylic acid bis(2-ethylhexyl) ester: C₆H₄(COOCH₂CH(C₂H₅)C₄H₉)₂ | 5.18 | 62.7 |
| P-8 | Benzene-1,2-dicarboxylic acid bis(n-octyl) ester: C₆H₄(COOC₈H₁₇(n))₂ | 5.04 | 40.0 |
| P-9 | Benzene-1,2-dicarboxylic acid bis(n-nonyl) ester: C₆H₄(COOC₉H₁₉(n))₂ | 4.70 | 1.03. |
| P-10 | Benzene-1,2-dicarboxylic acid bis(n-decyl) ester: C₆H₄(COOC₁₀H₂₁(n))₂ | 4.39 | 43.0 |
| P-11 | Benzene-1,2-dicarboxylic acid bis(iso-decyl) ester: C₆H₄(COOC₁₀H₂₁(iso))₂ | 4.44 | 92.9 |
| P-12 | Benzene-1,2-dicarboxylic acid bis(n-dodecyl) ester: C₆H₄(COOC₁₂H₂₅(n))₂ | 4.17 | 52.1 |
| P-13 | Benzene-1,2-dicarboxylic acid 1-butyl 2-benzyl ester | 6.56 | 50.0 |

-continued
| Compound No. | Structural Formula | Dielectric constant 25° C., (10 KHz) | Viscosity 25° C., cp |
|---|---|---|---|
| P-14 | 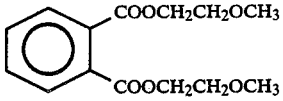 | 8.72 | 31.7 |
| P-15 | 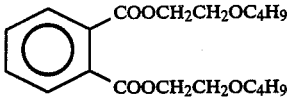 | 6.78 | 42.0 (20° C.) |
| P-16 | 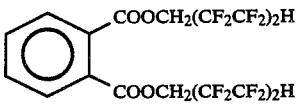 | 8.87 | 20.1 |
| P-17 | 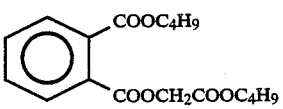 | 6.96 | 64.9 |
| P-18 | 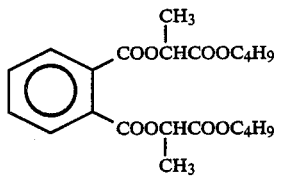 | 6.99 | 207. |
| P-19 | 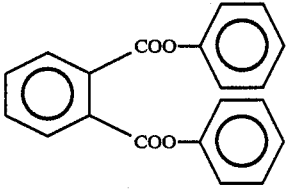 | 6.80 (Extrapolation) | Solid (mp 69° C.) |
| P-20 | 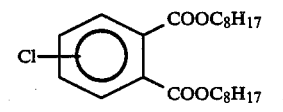 | 5.01 | 43.3 |
| P-21 | 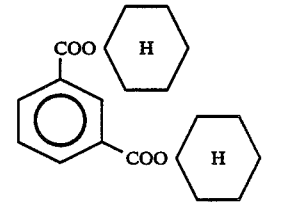 | 5.84 | 200 |
| P-22 | 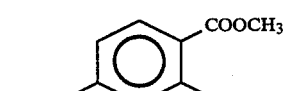 | 9.09 | 96.5 |
| P-23 | 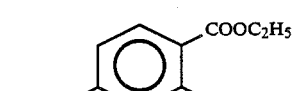 | 7.98 | 92.6 |

-continued

| Compound No. | Structural Formula | Dielectric constant 25° C., (10 KHz) | Viscosity 25° C., cp |
|---|---|---|---|
| P-24 | 1,2,4-C₆H₃(COOC₃H₇)₃ | 7.12 | 85.4 |
| P-25 | 1,2,4-C₆H₃(COOC₄H₉(n))₃ | 6.07 | 55.7 |
| P-26 | C₆H₅—COO(CH₂)₃OCO—C₆H₅ | 7.84 | Solid (mp 47° C.) |
| P-27 | CH₃O—C₆H₄—COOC₈H₁₇(n) | 5.90 | 15.3 |
| P-28 | CH₃CHCOOCH₂CHC₄H₉ with C₂H₅ and OCO—C₆H₅ substituents | 5.72 | 21.3 |
| P-29 | CH(CH₂OCO—C₆H₅)₂(CHOCO—C₆H₅) — glyceryl tribenzoate | 6.51 | Solid (mp 71° C.) |
| P-30 | CH₃—C(CH₂OCO—C₆H₅)₂(OCO—C₆H₅) | 4.99 | Solid (mp 81° C.) |
| P-31 | CH₃OCO—C(CH₂COOC₄H₉)₂(COOC₄H₉) | 6.02 | 42.7 |
| P-32 | C₄H₉(n)OOC—CH(OCOCH₃)—CH(OCOCH₃)—COOC₄H₉(n) | 5.29 | 76.6 |

-continued

| Compound No. | Structural Formula | Dielectric constant 25° C., (10 KHz) | Viscosity 25° C., cp |
|---|---|---|---|
| P-33 | HO—C(CH₂COOCH₂CH(C₂H₅)C₄H₉)₂—COOCH₂CH(C₂H₅)C₄H₉ with three CH₂COOCH₂CH(C₂H₅)C₄H₉ branches | 5.39 | 76.6 |
| P-34 | Cyclohexane-1,2-diyl bis[COOCH₂CH(C₂H₅)C₄H₉] | 4.43 | 32.5 |
| P-35 | Epoxycyclohexane-1,2-dicarboxylic acid di-C₈H₁₇ ester (COOC₈H₁₇) | 5.37 | 88.9 |
| P-36 | C₆H₅—COOCH₂(CF₂CF₂)₃H | 6.46 | 18.4 |
| P-37 | CHCOOCH₂(CF₂CF₂)₂H ‖ CHCOOCH₂(CF₂CF₂)₂H | 7.67 | 53.8 |
| P-38 | CH₂(COOCH₂C₆H₅)₂ | 6.12 | 27.5 |
| P-39 | (CH₂)₄[COOCH(CF₂CF₂)₂H][COOCH₂(CF₂CF₂)₂H] | 7.24 | 4.04 |
| P-40 | C₁₁H₂₃CON(C₂H₅)₂ | 13.45 | (mp 3–4° C.) |
| P-41 | Phthalic acid bis[(CH₂)₉—CH—CH₂ epoxide] ester | 5.8 | 140 |
| P-42 | Benzene-1,2,4-tricarboxylic acid tris[(CH₂)₂—CH—CH₂ epoxide] ester | 8.1 | 180 |

| Compound No. | Structural Formula | Dielectric constant 25° C., (10 KHz) | Viscosity 25° C., cp |
|---|---|---|---|
| P-43 | 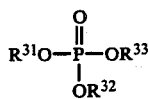 | 7.0 | 250 |

It is also preferred to use a phosphoric acid ester series compound represented by general formula [VI] show below as the high-boiling point organic solvent for dissolving the magenta couplers shown by general formula [I] for use in this invention.

$$R^{31}O-\underset{\underset{OR^{32}}{|}}{\overset{\overset{O}{\|}}{P}}-OR^{33} \qquad [VI]$$

wherein, $R^{31}$, $R^{32}$, and $R^{33}$ each represents an alkyl group, a substituted alkyl group, a cycloalkyl group, a substituted cycloalkyl group, an alkenyl group, a substituted alkenyl group, an aryl group, or a substituted aryl group, the sum of total carbon atoms shown by $R^{31}$, $R^{32}$, and $R^{33}$ being from 12 to 60.

When the high-boiling point organic solvent shown by abovedescribed general formula [VI] is used, the light absorption characteristics (e.g., half value width) and the light fastness of magenta dye images formed from the magenta couplers for use in this invention can be further improved.

The amount of the high-boiling organic solvent shown by general formula [VI] described above may be suitably selected according to the kind and the using amount of the magenta coupler but it is preferred that the ratio of the high-boiling point organic solvent to the magenta coupler is from 0.05 to 20 by weight ratio. Also, the high-boiling point organic solvent(s) shown by general formula [VI] may be used together with other conventional high-boiling point organic solvent(s) in the range capable of attaining the object of this invention. As these conventional high-boiling point organic solvents, there are, for example, phthalic acid ester series solvents such as dibutyl phthalate, di-2-ethylhexyl phthalate, etc., amide series solvents such as N,N-diethyldodecanamide, etc., aliphatic acid ester series solvents, benzoic acid ester series solvents, phenolic solvents such as 2,5-di-tert-amylphenol, etc., ether series solvents such as dihexadecyl ether. etc.

Then, specific examples of the high-boiling point organic solvent shown by general formula [VI] are illustrated below but the invention is not limited by these examples.

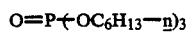 (P-44)

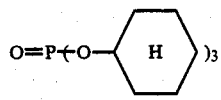 (P-45)

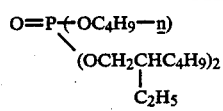 (P-46)

 (P-47)

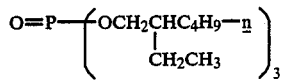 (P-48)

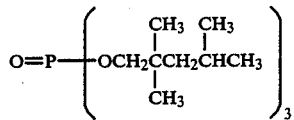 (P-49)

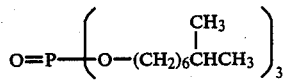 (P-50)

 (P-51)

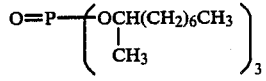 (P-52)

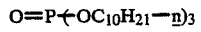 (P-53)

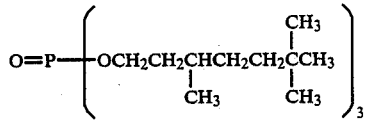 (P-54)

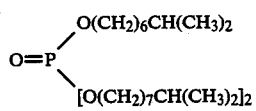 (P-55)

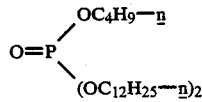 (P-56)

 (P-57)

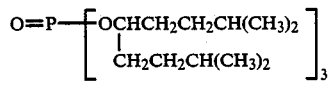 (P-58)

-continued (P-59) 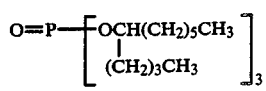

(P-60) 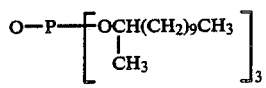

(P-61) 

(P-62) 

(P-63) 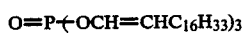

(P-64) 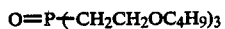

(P-65) 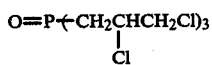

(P-66) 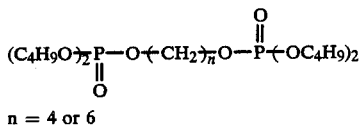
n = 4 or 6

(P-67) 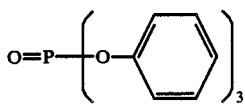

(P-68) 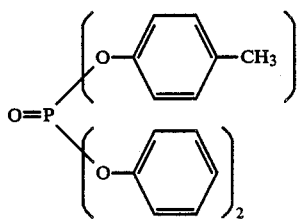

(P-69) 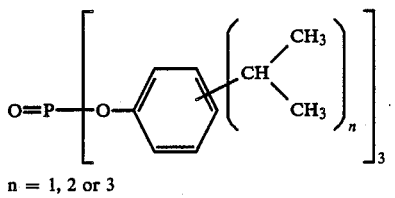
n = 1, 2 or 3

(P-70) 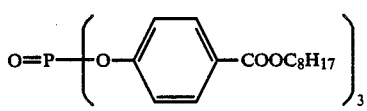

(P-71) 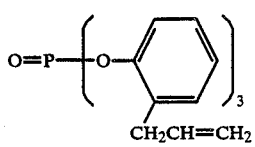

-continued (P-72) 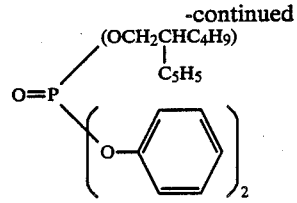

(P-73) 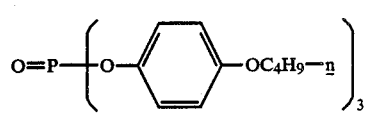

(P-74) 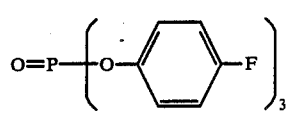

(P-75) 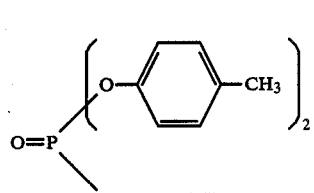

(P-76) 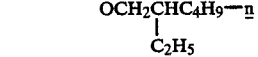

(P-77) 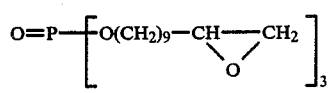

(P-78) 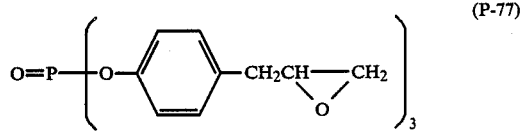

(P-79) 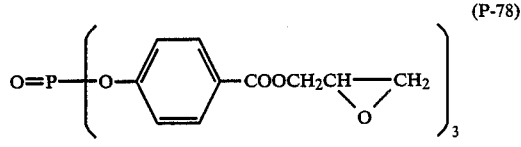

(P-80) 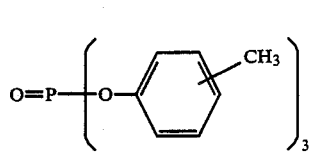

For introducing couplers in silver halide emulsion layers, the known method as described, for example, in U.S. Pat. No. 2,322,027 can be generally used.

The above-described high-boiling point organic solvents for use in this invention generally show very good dissolving power for the magenta couplers for use in this invention but if the solubility of the couplers is still insufficient for further reducing the coupler solvent to coupler ratio, other coupler solvents, such as phthalic acid ester series coupler solvents can be used together.

Also, in this invention, in the case of dissolving the couplers in the coupler solvents, an organic solvent having boiling point of about 30° to 150° C., such as lower alkyl acetates (e.g., ethyl acetate, butyl acetate, etc.,), ethyl propionate, secondary butyl alcohol, methyl isobutyl ketone, β-ethoxyethyl acetate, methylcellosolve acetate, etc., may exist together with the above-described coupler solvent(s).

In the case of introducing the coupler(s) dissolved in the coupler solvent(s) by the aforesaid method, a dispersion method by polymer described, for example, in Japanese Patent Publication No. 39,853/76, Japanese Patent Application (OPI) No. 59,943/76 can be used.

When the coupler has an acid group such as a carboxylic acid group and a sulfonic acid group, the coupler can be introduced into a hydrophilic colloid as an alkaline aqueous solution thereof.

For further improving the light fastness of magenta dye images, it is preferred to incorporate an ultraviolet absorbent in a layer or layers disposed at the opposite side of the layer containing the magenta coupler shown by general formula [I] described above to the support.

Ultraviolet absorbents which are generally used for photographic light-sensitive materials can be used in this invention but the ultraviolet absorbents shown by following general formula [VII], [VIII], or [IX] can be preferably used and in such a case, the light fastness of the magenta dye images can be greatly improved.

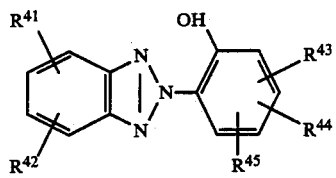

[VII]

wherein, $R^{41}$, $R^{42}$, $R^{43}$, $R^{44}$, and $R^{45}$ each represents a hydrogen atom, a halogen atom, an alkyl group, a cycloalkyl group, an alkoxy group, an aryl group, an aryloxy group, an alkenyl group, a nitro group, or a hydroxy group. (In the compounds shown by general formula [VII], resonance occurs in the benzotriazole moiety thereof.)

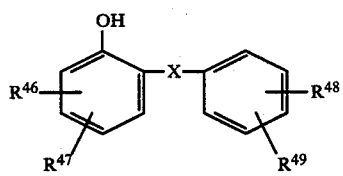

[VIII]

wherein, $R^{46}$, $R^{47}$, $R^{48}$, and $R^{49}$ each represents an hydrogen atom, a halogen atom, a nitro group, a hydroxy group, an alkyl group, an alkoxy group, an aryl group, or an aryloxy group and X represents —CO— or —COO—.

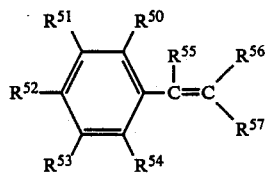

[IX]

wherein, $R^{50}$ to $R^{54}$ each represents a hydrogen atom, a halogen atom, an alkyl group, an aryl group, an alkoxy group, an aryloxy group, an alkylthio group, an arylthio group, an amino group, a hydroxy group, a cyano group, a nitro group, a carbamoyl group, a sulfonyl group, a sulfamoyl group, a sulfonamido group, an acyloxy group, or an oxycarbonyl group; $R^{55}$ represents a hydrogen atom or an alkyl group, $R^{56}$ and $R^{57}$ each represents a cyano group, —COOR$^{58}$, —CONHR$^{58}$, —COR$^{58}$ or —SO$_2$R$^{58}$; and $R^{58}$ represents an alkyl group or an aryl group.

The layers containing the ultraviolet absorbents for use in this invention include interlayers (e.g., an interlayer disposed between a green-sensitive emulsion layer and a red-sensitive emulsion layer), protective layers, silver halide emulsion layers (e.g., a red-sensitive emulsion layer, etc.,), etc.

The 2-(2'-hydroxyphenyl)benzotriazole series ultraviolet absorbent represented by general formula [VII] described above for use in this invention may be solid or liquid at normal temperature but the liquid ultraviolet absorbent is preferred. Specific examples of liquid ultraviolet absorbent which can be preferably used in this invention are described in Japanese Patent Publication Nos. 36,984/80, 12,587/80, Japanese Patent Application (OPI) No. 214,152/83, etc.

Details of the ultraviolet absorbents shown by general formula [VII] for use in this invention are described, for example, in Japanese Patent Application (OPI) Nos. 221,844/83, 46,646/84, 109,055/84, Japanese Patent Publication Nos. 10,466/61, 26,187/67, 5496/73, 41,572/73, U.S. Pat. Nos. 3,754,919, 4,220,711, etc.

Details of the benzophenon series ultraviolet absorbents represented by general formula [VIII] described above in U.S. Pat. No. 3,698,907 and Japanese Patent Publication No. 31,255/73, etc.

Also, details of the ultraviolet absorbents represented by general formula [IX]described above are described, for example, in Japanese Patent Application (OPI) Nos. 10,537/72, 111,942/83, U.S. Pat. No. 3,707,375, etc.

It is preferred that the above-described ultraviolet absorbent exists in the layer of the photographic light-sensitive material of this invention in an amount of about 0.01 to 2 parts by weight per part by weight of a binder for the layer to which the compound is added. Incidentaly, the coating amount of the binder for a photographic layer of a photographic light-sensitive material is usually about 0.1 to 3 g/m$^2$.

Then, specific examples of the ultraviolet absorbents shown by gneral formula [VII] to [IX] described above are illustrated below.

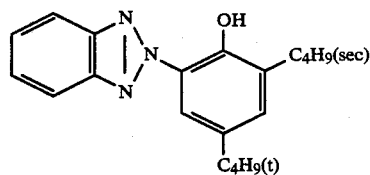

VII-1

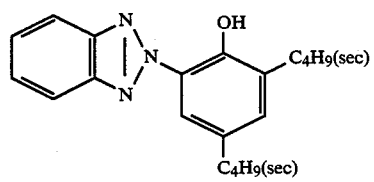

VII-2

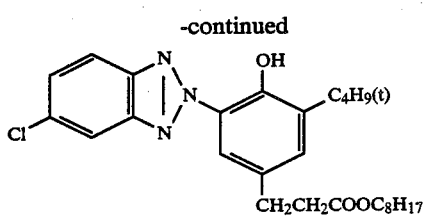

VII-3

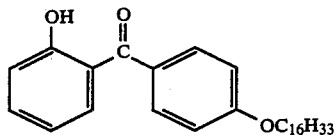

VIII-1

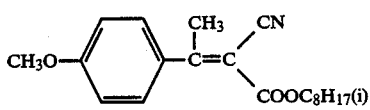

IX-1

Also, for further improving the light fastness of the magenta dye images in this invention, it is preferred that the pyrazoloazole type magenta coupler represented by above-described general formula [I] exists in the photographic layers(s) together with at least one of (i) an aromatic compound represented by general formula [Xa] shown below, (ii) an amine compound represented by general formula [Xb] shown below, and (iii) a metal complex having at least one organic ligand center metal such as copper, cobalt, nickel, palladium, or platinum and at least one organic ligand having two or more conformations.

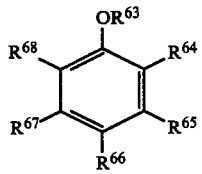

[Xa]

wherein, $R^{63}$ represents a hydrogen atom, an alkyl group, an alkenyl group, an aryl group, a heterocyclic group, or

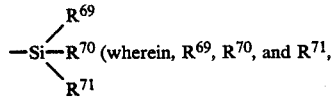

(wherein, $R^{69}$, $R^{70}$, and $R^{71}$, which may be the same or different, each represents an alkyl group, an alkenyl group, an aryl group, an alkoxy group, an alkenoxy group, or an aryloxy group); $R^{64}$, $R^{65}$, $R^{66}$, $R^{67}$, and $R^{68}$, which may be the same or different, each represents a hydrogen atom, an alkyl group, an alkenyl group, an aryl group, an acylamino group, an alkylamino group, an alkylthio group, an arylthio group, an alkoxycarbonyl group, an aryloxycarbonyl group, a halogen atom, or —O—$R^{63'}$ (wherein, $R^{63'}$ represents each of the groups shown by $R^{63}$); said $R^{63}$ and $R^{64}$ may combine with each other to form a 5-membered ring, a 6-membered ring, or a spiro ring; and said $R^{64}$ and $R^{65}$ or said $R^{65}$ and $R^{66}$ may combine with each other to form a 5-membered ring, a 6-membered ring, or a spiro ring.

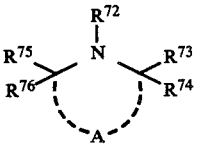

[Xb]

wherein, $R^{72}$ represents a hydrogen atom, an alkyl group, an alkenyl group, an alkinyl group, an acyl group, a sulfonyl group, a sulfinyl group, an oxyradical group or a hydroxy group; $R^{73}$, $R^{74}$, $R^{75}$ and $R^{76}$, which may be the same or different, each represents a hydrogen atom or an alkyl group; and A represents a non-metallic atomic group necessary for forming a 5-membered, 6-membered or 7-membered ring.

In the groups of general formulae [Xa] and [Xb] described above, the groups containing even partially an alkyl group, an aryl group, or a heterocyclic ring may be further substituted.

In the amine compounds represented by general formula [Xb] described above, it is preferred that A represents a non-metallic atomic group necessary for forming a 6-membered ring.

The metal complex (iii) for use in this invention is explained in detail. The metal complex for use in this invention is a compound having a center metal such as copper, cobalt, nickel, palladium or platinum and having at least one organic ligand having 2 or more conformations. In the center metals, nickel is particularly preferred. As the coordination atom coordinating to the center metal, a nitrogen atom, a sulfur atom, an oxygen atom, and a phosphorus atom are preferred.

The aromatic compound represented by general formula [Xa], the amine compound represented by general formula [Xb] and the metal complex described above are disclosed in detail in Japanese Patent Application (OPI) No. 217314/85, at pages 11 to 18.

Then, specific examples of the compounds shown by general formulae [Xa] and [Xb] and the metal complexes are illustrated below but the invention are not limited to these compounds.

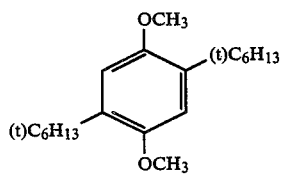

A-1

-continued
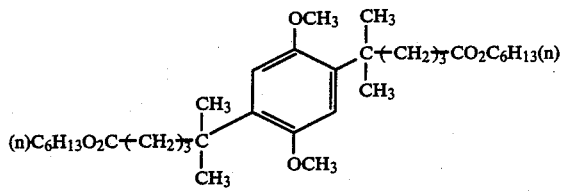
A-2
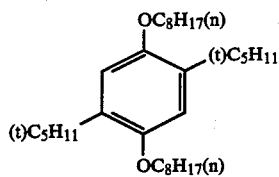
A-3
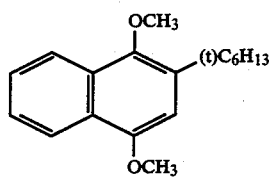
A-4
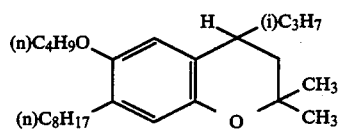
A-5
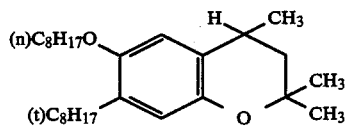
A-6
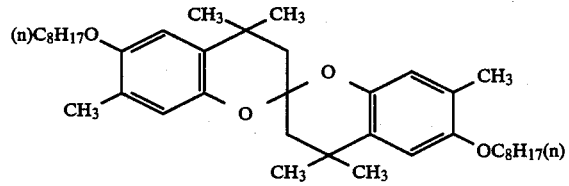
A-7
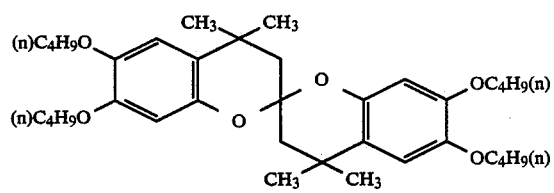
A-8
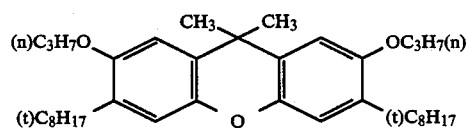
A-9
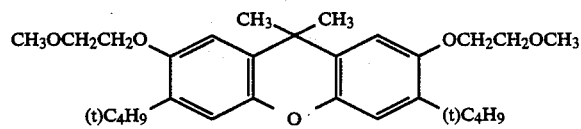
A-10
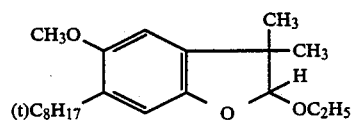
A-11

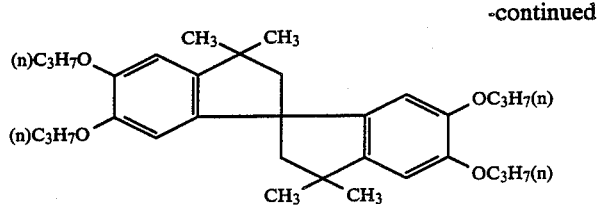
A-12
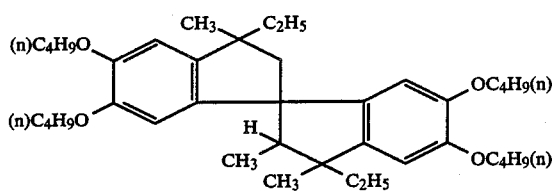
A-13
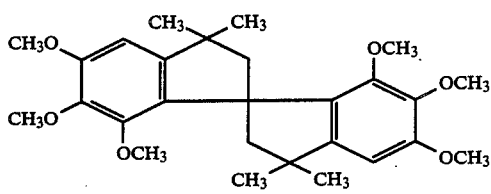
A-14
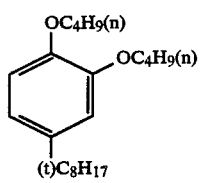
A-15
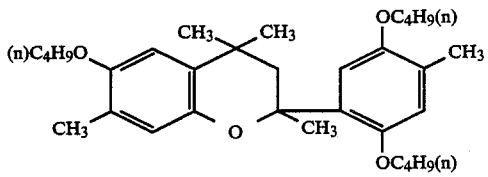
A-16
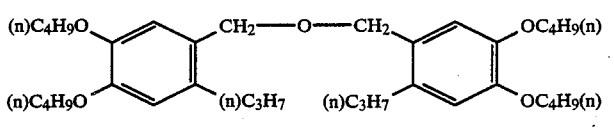
A-17
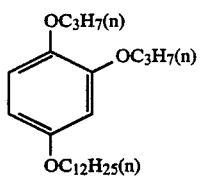
A-18
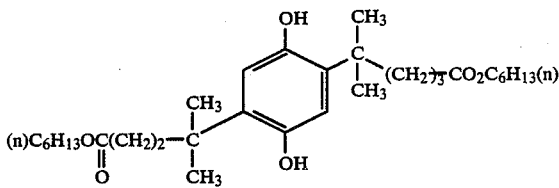
A-19
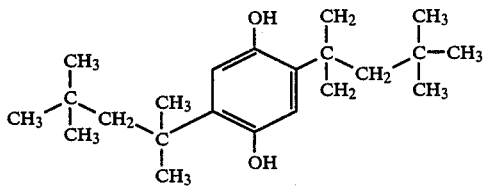
A-20

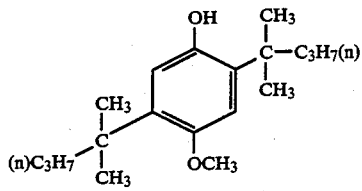 A-21
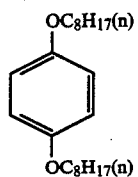 A-22
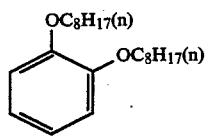 A-23
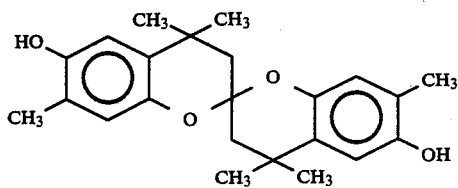 A-24
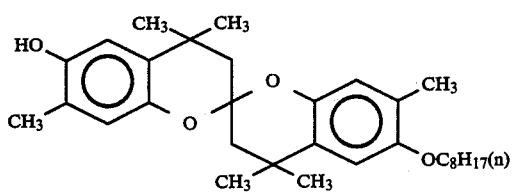 A-25
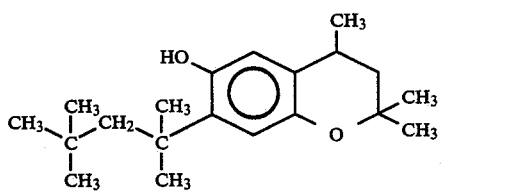 A-26
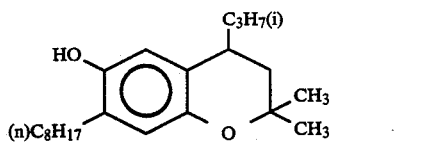 A-27
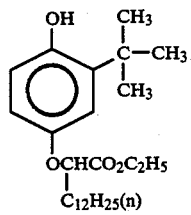 A-28
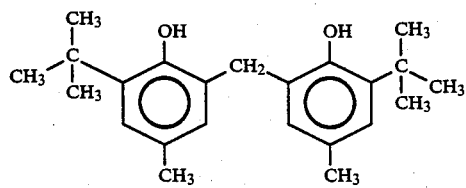 A-29

-continued
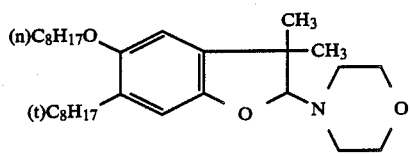
A-30
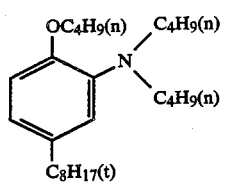
A-31
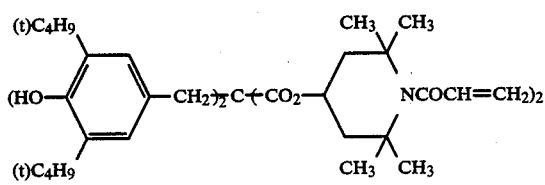
A-32
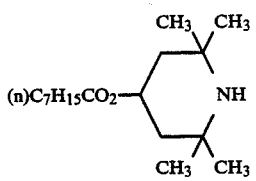
A-33
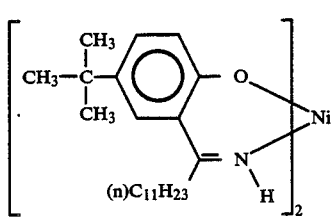
A-34
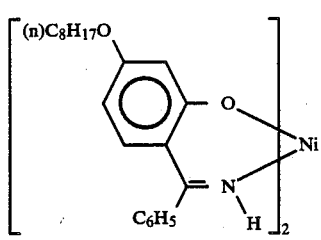
A-35
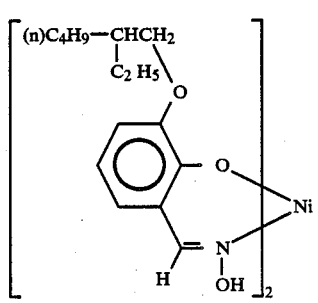
A-36

-continued
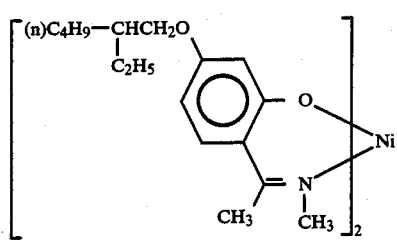
A-37
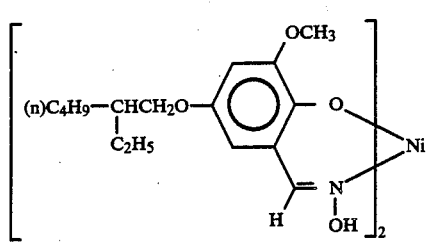
A-38
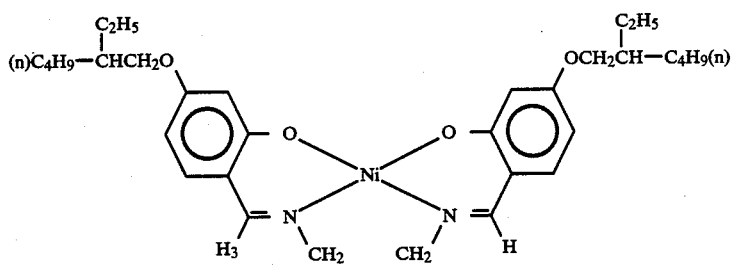
A-39
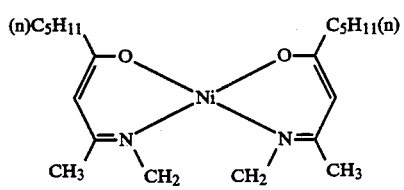
A-40
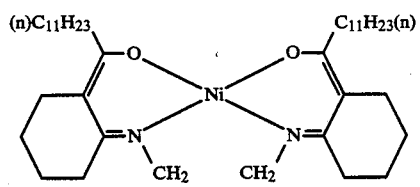
A-41
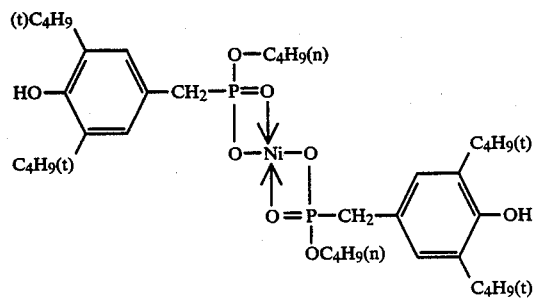
A-42

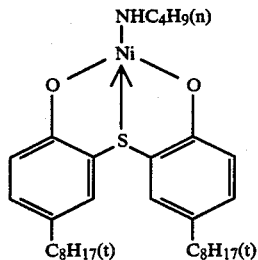

A-43

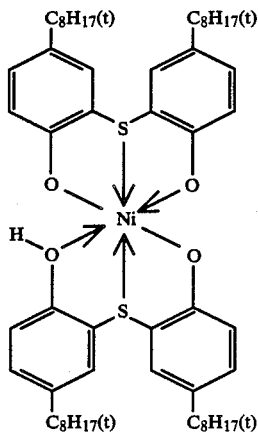

A-44

The compound shown by general formula [Xa] or [Xb] described above for use in this invention is used in an amount of from 10 to 400 mol %, preferably from 30 to 300 mol % to the magenta coupler shown by general formula [I] described above. On the other hand, the metal complex for use in this invention is used in an amount of from 1 to 100 mol %, preferably from 3 to 40 mol % to the coupler shown by general formula [I].

The magenta couplers and the above-described fading preventing agents represented by general formulae [Xa] and [Xb] can be incorporated in at least one hydrophilic organic colloid layer constituting the photographic emulsion layer(s) of the silver halide color photographic material of this invention, using a high-boiling point organic solvent, preferably the above-described high-boiling point organic solvent.

In this invention, it is preferred that the silver halide emulsion containing the pyrazoloazole series magenta coupler represented by general formula [XI] shown below contains a water-soluble iridium salt in an amount of from $10^{-9}$ to $10^{-3}$ mol per mol of the silver halide thereof.

Thus, the silver halide color photographic material composed of the above-described silver halide emulsion(s) is excellent in sensitivity, color reproducibility, and image storing property as well as can reduce the reliability to the surrounding conditions at photographying or developing. Also, the silver halide color photographic material has an excellent advantage that in color images obtained, the occurence of yellowing of the background portions caused during storage is greatly reduced.

Preferred examples of the iridium salt which is incorporated in the silver halide emulsion are shown below.

| (Ir-1) | K₃IrCl₆ |

-continued

| (Ir-2) | K₂IrCl₆ |
| (Ir-3) | K₃IrBr₆ |
| (Ir-4) | K₂IrBr₆ |
| (Ir-5) | IrCl₃ |
| (Ir-6) | IrBr₄ |

It is preferred that the iridium salt is added to the silver halide emulsion in the above-described amount at the formation of silver halide.

Also, according to a still other embodiment of this invention, by using the magenta coupler(s) represented by general formula [XI] shown below together with a nitrogen-containing heterocyclic compound represented by general formula [XII], [XIIIa], [XIIIb], [XIV], [XV], [XVIa], or [XVIb] described hereinbelow, color photograhpic images having no color stains at the background portions and low density image portions.

Also, the silver halide color photographic material having the above-described combination of the magenta coupler and the nitrogen-containing heterocyclic compound has an improved advantage that the color images formed have high fastness and the formation of stains in the background portions is less. Furthermore, in the photographic light-sensitive material, magenta dye images having good spectral absorption characteristics are obtained and also photographic images having excellent color reproducibility are formed.

The photographic layer containing the nirtogen-containing heterocyclic compound shown by general formula XII] to [XVI] described below may be any layer in the color photographic light-sensitive material, or the heterocyclic compound may exist in two or more layers, but it is preferred that the compound exists in the emulsion layer containing the magenta coupler shown by general formula [XI] described below.

Also, the addition amount of the nirtogen-containing hetreocyclic compound shown by general formula

[XII] to [XVI] is from $10^{-7}$ mol to $10^{-1}$ mol, preferably from $10^{-5}$ mol to $10^{-2}$ mol per mol of the silver halide of the layer containing the magenta coupler shown by general formula [XI].

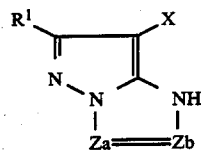
[XI]

wherein, Za and Zb each represents

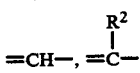

(wherein, $R^2$ represents a substituent), or =N—; $R^1$ and $R^2$ each represents a hydrogen atom or a substituent; and X represents a hydrogen atom or a group capable of releasing by a coupling reaction with the oxidation product of an aromatic primary amine developing agent. When the bond Za=Zb is a carbon-carbon double bond, the bond may be a part of an aromatic ring and the coupler shown by the general formula may form a dimer or more polymer at said $R_1$, $R_2$, or X.

When two $R^2$ exist in one molecule, said $R^2$s may be the same or different and also (i) when $R^2$ does not exist in the molecule, $R^1$ represents a group bonding to the pyrazoloazole ring through a secondary tertiary carbon atom or (ii) when $R^2$ exists in the molecule, at least one of $R^1$ and $R^2$ represents a group bonding to the pyrazoloazole ring through a secondary or tertiary carbon atom.

Furthermore, at least one of $R^1$ and $R^2$ is a group having at least one group —NHSO$_2$—.

Then, the pyrazoloazole series magenta coupler shown by general formula [XI] above are explained in detail.

In general formula [XI], the term "dimer or more polymer" means a compound having 2 or more moieties shown by general formula [XI] in one molecule and a bis-compound and a polymer coupler are included therein.

In this case, the polymer coupler may be a homopolymer composed of a monomer (preferably a monomer having a vinyl group, hereinafter, the monomer is referred to as a vinyl monomer) only having the moiety shown by general formula [XI] or a copolymer of the vinyl monomer and the noncoloring ethylenical monomer which does not cause coupling with the oxidation product of an aromatic primary amine developing agent.

The term "secondary or tertiary carbon atom" in a group bonding to the pyrazoloazole ring through a secondary or tertiary carbon atom means a carbon atom substituted with one carbon atom for one hydrogen atom of a methylene group bonding to the pyrazoloazole ring, or substituted with two carbon atoms for two hydrogen atoms of the methylene groups, respectively.

Now, the pyrazoloazole series magenta couplers shown by general formula [XI] described above can be also represented by general formula [XI - 1], [XI - 2], [XI - 3], [XI - 4], and (XI - 5] shown below.

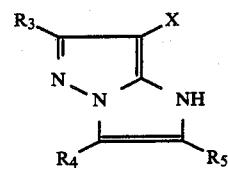
(XI-1)

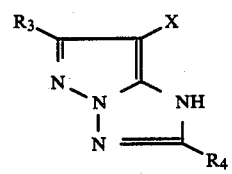
(XI-2)

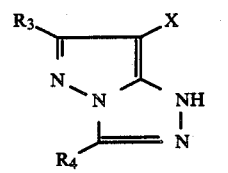
(XI-3)

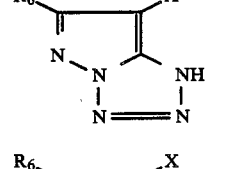
(XI-4)

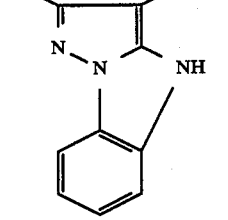
(XI-5)

In the above-described magenta couplers shown by general formulae [XI - 1] to [XI - 5] described above, the couplers shown by general formulae [XI - I], [XI - 2] and [XI - 3] are preferred and also the couplers shown by general formula [XI - 2] are more preferred for the objects of this invention.

In general formulae [XI - 1] to [XI - 3], $R^3$, $R^4$, and $R^5$ each represents a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, or an aryloxycarbonyl group; at least one of said $R^3$, $R^4$, and $R^5$ represents a group directly bonding to the pyrazoloazole ring through a secondary or tertiary carbon atom and further at least one of said $R^3$, $R^4$, and $R^5$ is a group having at least one —NHSO$_2$— group which is present at any position of the group shown above for $R^3$, $R^4$ or $R^5$. It is preferred that $R^4$ in general formula [XI-3] is not a substituted or unsubstituted aralkyl groupl. In particular, it is most preferred that above-described —NHSO₂— group is directly bonded to an alkylene group directly bonded to the pyrazoloazole ring.

The —NHSO₂— group bonded to an alkylene group which is bonded to the pyrazoloazole ring is represented by following general formulae [XI-1] and [XI-2].

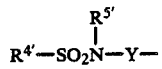  [XI-6]

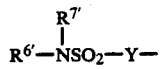  [XI-7]

wherein, $R^{4'}$ and $R^{6'}$ each represents an alkyl group, an aryl group or a heterocyclic group, (preferably comprising 5- or 6-membered ring or condensed ring thereof containing at least one atom of O, S and N atoms), which may have at least one substituent selected from the groups represented by $R^3, R^4$ and $R^5$ disclosed above.

$R^{5'}$ and $R^{7'}$ each preferably represents a hydrogen atom, an alkyl group, an aryl group or a heterocyclic group (preferably comprising 5- or 6-membered ring or condensed ring thereof containing at least one atom of O, S and N atoms), which may have at least one substituents selected from the groups represented by $R^3, R^4$ and $R^5$ disclosed above. $R^{5'}$ and $R^{7'}$ each more preferably represents a hydrogen atom. Y represents an alkylene group. The alkylene group preferably contains 1 to 10 carbon atoms in a straight-chain moiety thereof and may have at least one substituent selected from the same groups as those represented by $R^3, R^4$ and $R^5$ disclosed above.

Most preferred alkylene group includes one having a secondary or tertiary carbon atom directly bonded to the skeleton. The total carbon atoms of $R^{4'}, R^{5'}$ and Y, or $R^{6'}, R^{7'}$ and Y preferably are 2 to 65. Preferred examples of the aryl group represented by $R^{4'}, R^{5'}, R^{6'}$ and $R^{7'}$ include a phenyl group and a naphthyl group and their derivatives. Preferred examples of the heterocyclic group include the same as those disclosed above for the groups represented by $R^3, R^4$ and $R^5$.

In general formulae [XI-4] to [XI-5] described above, $R^6$ represents a group directly bonding to the pyrazoloazole ring through a secondary or tertiary carbon atom. $R^6$ represents a group bonding to the group shown above for $R^3, R^4$ or $R^5$ through the secondary or tertiary carbon atom and contains —NHSO₂— group at any position of the group shown above for $R^3, R^4$ or $R^5$. It is preferred that, in $R^6$, the —NHSO₂— group is bonded to the pyrazoloazole ring through an alkylene group, wherein a carbon atom of the alkylene group which is directly bonded to the pyrazoloazole ring is a secondary or tertiary carbon atom. Further, it is most preferred that, in $R^6$, the —NHSO₂— group is directly bonded to an alkylene group directly bonded to the pyrazoloazole ring.

In general formulae [XI-1] to [XI-5], X represents a hydrogen atom, a halogen atom, a carboxy group or a group which is bonded to a carbon atom of the coupling position through an oxygen atom, a nitrogen atom, or a sulfur atom and is released at coupling.

X represents a hydrogen atom or a group capable of releasing by a coupling reaction with the oxidation product of an aromatic primary amino developing agent.

Also, the couplers shown by general formula [XI - 1] to [XI - 5] include the case that $R^3, R^4, R^5, R^6$, or X becomes a divalent group and the coupler forms a bi-compound. Furthermore, when the moiety shown by general formula [XI - 1] to [XI - 5] exists in the vinyl monomer, $R^3, R^4, R^5$, or $R^6$ represents a single bond or a linkage group, through which a vinyl group is bonded to the moiety shown by general formula [XI - 1] to [XI - 5].

The groups of general formulae [XI - 1] to [XI - 5] are further explained in more detail.

$R^3, R^4$, and $R^5$ each represents a hydrogen atom, a halogen atom (e.g., a chlorine atom, a bromine atom, etc.,), an alkyl group (e.g., a methyl group, a propyl group, a hexyl group, a trifluoromethyl group, a tridecyl group, a 3-(2,4-di-t-amylphenoxy)propyl group, a 2-dodecyloxyethyl group, a 3-phenoxypropyl group, a 2-hexylsulfonyl-ethyl group, a cyclopentyl group, a benzyl group, etc.,), an aryl group (e.g., a phenyl group, a 4-t-butylphenyl group, a 2,4-di-t-amylphenyl group, a 4-tetradecanamidophenyl group, etc.,), a heterocyclic group preferalby being 5- or 6-membered ring or condensed ring thereof containing at least one atom of O, N, and S, (e.g., a 2-furyl group, a 2-thienyl group, a 2-pyrimidinyl group, a 2-benzothiazolyl group, etc.,), a cyano group, an alkoxy group (e.g., a methoxy group, an ethoxy group, a 2-methoxyethoxy group, a 2-phenoxyethoxy group, a 2-dodecyloxyethoxy group, a 2-methanesulfonylethoxy group, etc.,), an aryloxy group (e.g., a phenoxy group, a 2-methylphenoxy group, a 4-t-butylphenoxy group, etc.,), a heterocyclic oxy group preferably being 5- or 6-membered ring or condensed ring thereof containing at least one atom of O, N, and S (e.g., a 2-benzimidazolyloxy group, etc.,), an acyloxy group (e.g., an acetoxy group, a hexadecanoyloxy group, etc.,), a carbamoyloxy group (e.g., an N-phenylcarbamoyloxy group, an N-ethylcarbamoyloxy group, etc.,), a silyloxy group (e.g., a trimethylsilyloxy group, etc.,), a sulfonyloxy group (e.g., a dodecylsulfonyloxy group, etc.,), an acylamino group (e.g., an acetamido group, a benzamido group, a tetradecanamido group, an α-(2,4-di-t-amylphenoxy)-butylamido group, a γ-(3-t-butyl-4-hydroxyphenoxy)-butylamido group, an α-{4-(4-hydroxyphenylsulfonyl)-phenoxy}decanamido group, etc.,), an anilino group (e.g., a phenylamino group, a 2-chloroanilino group, a 2-chloro-5-tetradecanamidoanilino group, a 2-chloro-5-dodecyloxycarbonylanilino group, an N-acetylanilino group, a 2-chloro-5-{α-(3-t-butyl-4-hydroxyphenoxy)-dodecanamido}anilino group, etc.,), a ureido group (e.g., a phenylureido group, a methylureido group, an N,N-dibutylureido group, etc.,), an imido group (e.g., an N-succinimido group, a 3-benzylhydantoinyl group, a 4-(2-ethylhexanoylamino)phthalimido group, etc.,), a sulfamoylamino group (e.g., an N,N-dipropylsulfamoylamino group, an N-methyl-N-decylsulfamoylamino group, etc.,), an alkylthio group (e.g., a methylthio group, an octylthio group, a tetradecylthio group, a 2-phenoxyethylthio group, a 3-phenoxypropylthio group, a 3-(4-t-butylphenoxy)propylthio group, etc.,), an arylthio group (e.g., a phenylthio group, a 2-butoxy-5-t-octylphenylthio group, a 3-pentadecylphenylthio group, a 2-carboxyphenylthio group, a 4-tetradecanamidophenylthio group, etc.,), a heterocyclic thio group preferably being 5- or 6-membered ring containing at least one atom of O, S, and N (e.g., a 2-benzothiazolylthio group, etc.,), an alkoxycarbonylamino group (e.g., a methoxycarbonylamino group, a tetradecyloxycarbonylamino group, etc.,), an aryloxycarbonylamino group (e.g., a phenoxycarbonylamino group, a 2,4-di-tert-butylphenoxycarbonylamino group, etc.,), a sulfonamido group (e.g., a methanesulfonamido group, a hexadecanesulfonamido group, a benzenesulfonamido group, a p-toluenesulfonamido group, an octandecansulfonamido group, a 2-methyloxy-5-t-butylbenzenesulfonamido group, etc.,), a carbamoyl group (e.g., an N-ethylcarbamoyl group, an N,N-dibutylcarbamoyl group, an N-(2-dodecyloxyethyl)carbamoyl group, an N-methyl-N-dodecylcarbamoyl group, an N-3-(2,4-di-tert-amylphenoxy)propyl carbamoyl group, etc.,), an acyl group (e.g., an acetyl group, a (2,4-di-tert-amylphenoxy)acetyl group, a benzoyl group, etc.,), a sulfamoyl group (e.g., an N-ethylsulfamoyl group, an N,N-dipropylsulfamoyl group, an N-(2-dcdecyloxyethyl)sulfamoyl group, an N-ethyl-N-dodecylsulfamoyl group, an N,N-diethylsulfamoyl group, etc.,), a sulfonyl group (e.g., a methanesulfonyl group, an octanesulfonyl group, a benzensulfonyl group, a toluenesulfonyl group, etc.,), a sulfinyl group (e.g., an octanesulfinyl group, a dodecylsulfinyl group, a phenylsulfinyl group, etc.,), an alkoxycarbonyl group (e.g., a methoxycarbonyl group, a butyloxycarbonyl group, a dodecylcarbonyl group, an octadecylcarbonyl group, etc.,), an aryloxycarbonyl group (e.g., a phenyloxycarbonyl group, or a 3-pentadecyloxycarbonyl group, etc.,).

The alkyl group, alkoxy group, alkylthio group, alkoxycarbonylamino group and alkoxycarbonyl group represented by $R^1$ and $R^2$ as is described above each preferably contains 1 to 38 carbon atoms and further may have substituents. The aryl group, aryloxy group, anilino group, arylthio group and aryloxycarbonyl amino group represented by $R^1$ and $R^2$ as is described above each preferably includes a phenyl group or a naphthyl group and further may have substituents.

The groups represented by $R^1$ and $R^2$ may have further substituents.

Also, as described above, at least one of said $R^3$, $R^4$ and $R^5$ represents a group directly bonding to the pyrazoloazole ring through a secodnary or tertiary carbon atom. Examples of such a group are an isopropyl group, a t-butyl group, a t-hexyl group, a cyclohexyl group, an adamantyl group, a 1-ethoxyisopropyl group, a 1-phenoxy-1,1-dimethylmethyl group, an α,α-dimethylbenzyl group, an α,α-dimethylphenylethyl group, an α-ethylbenzyl group, a 1-ethyl-1-[4-(2-butoxy-5-tert-octylbenzenesulfonamido)phenyl]methyl group, a 1-methyl-2-[4-(4-dodecyloxybenzenesulfonamido)phenyl]ethyl group, a 1-methyl-2-(2-octyloxy-5-tert-octylbenzenesulfonamido)ethyl group, a 1,1-dimethyl-2-(2-octyloxy-5-tert-octylbenzenesulfonamido)ethyl group, a 1-methyl-2-[2-oxtyloxy-5-(2-octyloxy-5-tert-octylbenzenesulfonamido)benzenesulfonamido]ethyl group, a 1-ethyl-2-(2-dodecyloxy-5-tert-octylbenzenesulfonamido)ethyl group, a 1-(2-hydroxyethyl)-2-{α-[3-(2-octyloxy-5-tert-octylbenzenesulfonamido)phenoxy]dodecanamido,}ethyl group, etc.

Also, X represents a hydrogen atom; a halogen atom (e.g., a chlorine atom, a bromine atom, an iodine atom, etc.,); a carboxy group; a group bonded with an oxygen atom preferably including an acyloxy group, an oxazolyloxy group, a pyruvinyloxy group, an alkenyloxy group, an aryloxy group, an arylalkoxycarbonyloxy group, an alkoxy group, a tetrazolyloxy group, a thiazolyloxy group and derivatives thereof (e.g., an acetoxy group, a propanoyloxy group, a benzoyloxy group, a 2,4-dichlorobenzoyloxy group, an ethoxyoxazolyloxy group, pyruvinyloxy group, a cinnamoyloxy group, a phenoxy group, a 4-cyanophenoxy group, a 4-metanesulfonamidophenoxy group, a 4-methanesulfonylphenoxy group, an α-naphthoxy group, a 3-pentadecylphenoxy group, a benzyloxycarbonyloxygroup, an ethoxy group, a 2-cyanoethoxy group, a benzyloxy group, a 2-phenethyloxy group, a 2-phenoxyethoxy group, a 5-phenyltetrazolyloxy group, a 2-benzothiazolyloxy group, etc.,); a group bonded with a nitrogen atom preferably including a sulfonamido group, a piperidyl group, a carbonamido group, an ureido group, an amino group, an oxazolidinyl group, a hydantionyl group, an isothiazolyl group, a pyridinyl group, an imidazolyl group, a pyrazolyl group, a triazolyl group, a tetrazolyl group (e.g., a benzenesulfonamido group, an N-ethyltoluenesulfonamido group, a heptafluorobutaneamido group, a 2,3,4,5,6-pentafluorobenzamido group, an octanesulfonamido group, a p0cyanophenylureido group, an N,N-diethylsulfamoylamino group, a 1-piperidyl group, a 5,5-dimethyl-2,4-dioxo-3-oxazolidinyl group, a benzyl-ethoxy-3-hydantoinyl group, a 2N-1,1-dioxo-3(2H)-oxo-1,2-benzoisothiazolyl group, a 2-oxo-1,2-dihydro-1-pyridinyl group, an imidazolyl group, a pyrazolyl group, a 3,5-diethyl-1,2,4-triazol-1-yl, 5- or 6-bromo-benzotriazol1-yl group, a 5-methyl-1,2,3,4-triazole-1-yl group, a benzimidiazolyl group, a 3-benzyl-1-hydanoinyl group, a 1-benzyl-5-hexadecyloxy-3-hydanoinyl group, a 5-methyl-1-tetrazolyl group etc.; a arylazo group preferably including a phenylazo group, a naphthylazo group and derivatives thereof (e.g., a 4-methoxyphenylazo group, a 4-pivaloylaminophenylazo group, a 2-naphthylazo group, a 3-methyl-4-hydroxyphenylazo group, etc.,) or a group bonded by a sulfur atom preferably including an arylthio group, an alkylthio group, a triazolyl thio group, a tetrazolylthio group, a thiazolylthio group, a thiophenylthio group and derivatives thereof (e.g., a phenylthio group, a 2-carboxyphenylthio group, a 2-butoxy-5-t-octylphenylthio group, a 4-methanesulfonylphenylthio group, a 4-octanesulfonamidophenylthio group, a 2-butoxyphenylthio group, a 2-(2-hexanesulfonylethyl)-5-tert-octylphenylthio group, a benzylthio group, a 2-cyanoethylthio group, a 1-ethoxycarbonyltridecylthio group, a 5-phenyl-2,3,4,5-tetrazolylthio group, a 2-benzothiazolyl group, a 2-dodecylthio-5-thiophenylthio group, a 2-phenyl-3-dodecyl-1,2,4-triazolyl-5-thio group, etc.,).

Also, as described above, the coupler shown by general formula [XI - 1] to [XI - 5] described above includes the case that $R^3$, $R^4$, $R^5$, or X becomes a divalent group and the coupler forms a bis-compound, and examples of the divalent group are a substituted or unsubstituted alkylene group (e.g., a methylene group, an ethylene group, a 1-ethylethylene group, a 1,10-decylene group, —CH$_2$CH$_2$—O—CH$_2$CH$_2$—, etc.,), a substituted or unsubstituted phenylene group (e.g., a 1,4-phenylene group, a 1,3-phenylene group,

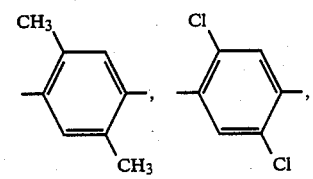

(etc.), —NHCO—R[7]—CONH— (wherein, R[7] represents a substituted or unsubstituted alkylene group or a substituted or unsubstituted phenylene group), etc.

In the case that $R_6$ in general formula [XI - 4] or [XI - 5] described above becomes a divalent group and the coupler shown by the general formula forms a bis-compound, the divalent group forms the above-described alkylene group which is bonded to the pyrazoloazole ring through a secondary or tertiary carbon atom.

Also, as described above, when the coupler moiety shown by general formula [XI - 1] to [XI - 5] exists in the vinyl monomer, $R^3$, $R^4$, or $R^5$ represents a linkage group and examples of the linkage group include a combination of the groups selected from an alkylene group (i.e., a substituted or unsubstituted alkylene group such as a methylene group, an ethylene group, a 1-methylethylene group, a 1,10-decylene group, —CH$_2$CH$_2$OCH$_2$CH$_2$—, etc.,), a phenylene group (i.e., a substituted or unsubstituted phenylene group such as a 1,4-phenylene group, a 1,3-phenylene group,

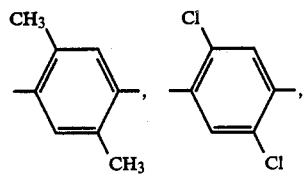

(etc.), —NHCO—, —CONH—, —O—, and —OCO—, or combination of them, the combination of the groups includes, for example,

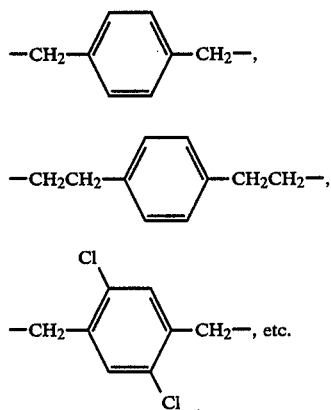

The alkylene group of the linkage group represented by $R^1$, $R^2$ or X which is included in a dimer or a more polymer preferably contains 1 to 38 carbon atoms and substituent of the linkage group above described preferably includes an alkyl group, an alkoxy group, an aryl group, a halogen atom, etc.

The alkylene linkage group shown by $R^6$ represents the above-described alkylene group which is bonded to the pyrazoloazole ring through a secondary or tertiary carbon atom.

In addition, the vinyl group in the vinyl monomer includes the case of having a substituent in addition to those shown by general formulae [XI - 1] to [XI - 5]. Examples of the preferred substituent are a hydrogen atom, a chlorine atom and a lower alkyl group having 1 to 4 carbon atoms.

Also, examples of the non-coloring ethylenical monomer which does not cause coupling with the oxidation product of an aroamtic primary amine developing agent are acrylic acid, α-chloroacrylic acid, α-aracrylic acid (e.g., methacrylic acid, etc.,), esters or amides derived from these acrylic acids (e.g., acrylamide, n-butylacrylamide, t-butylacrylamide, diacetonacrylamide, methacrylamide, methyl acrylate, ethyl acrylate, n-propyl acrylate, n-butyl acryalte, t-butyl acrylate, iso-butyl acrylate, 2-ethylhexyl acrylate, n-octyl acrylate, laurylacrylate, methyl methacrylate, ethyl methacrylate, n-butyl methacyrlate, β-hydroxy methacrylate, etc.,), methylenedibisacrylamide, a vinyl ester (e.g., vinyl acetate, vinyl propionate, vinyl laurate, etc.,), acrylonitrile, methacrylonitrile, an aromatic vinyl compound (e.g., styrene and the derivatives thereof, vinyltoluene, divinylbenzene, vinylacetophenone, sulfostyrene, etc.,), itaconic acid, citraconic acid, crotonic acid, vinylidene chloride, a vinyl alkyl ether (e.g., vinyl ethyl ether, etc.,), maleic acid, maleic anhydride, maleic acid ester, N-vinyl-2-pyrrolidone, N-vinylpyridine, 2- and 4-vinylpyridine, etc. Two or more kinds of such non-coloring ethylenically unsatruated monomers may be used Then, examples of the pyrazoloazole type magenta couplers for use in this invention are illustrated below but the invention is not limited to these couplers.

XI-1

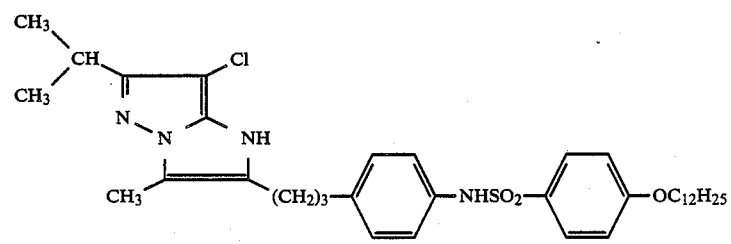

-continued
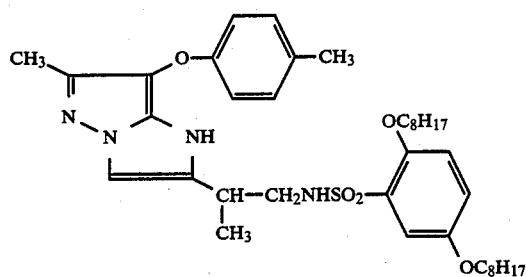
XI-2
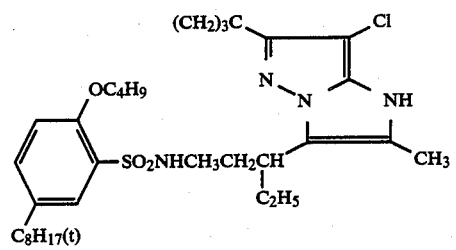
XI-3
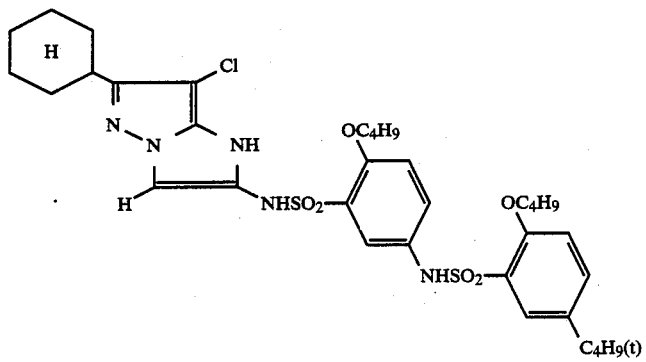
XI-4
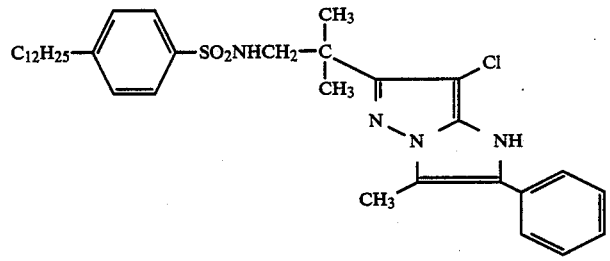
XI-5
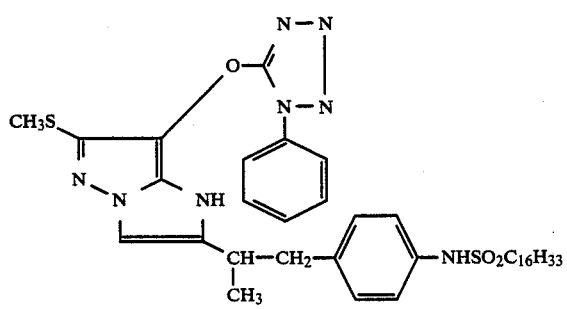
XI-6

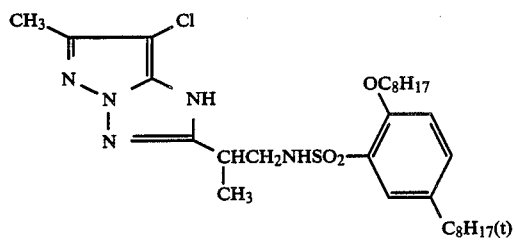
XI-7
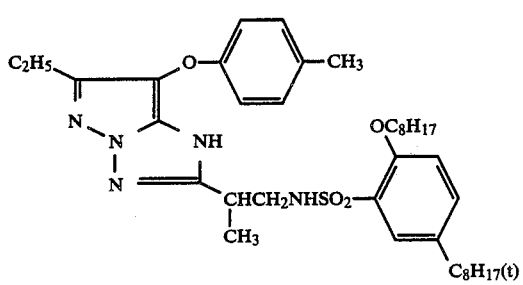
XI-8
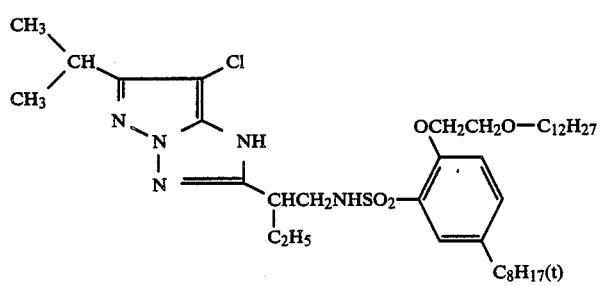
XI-9
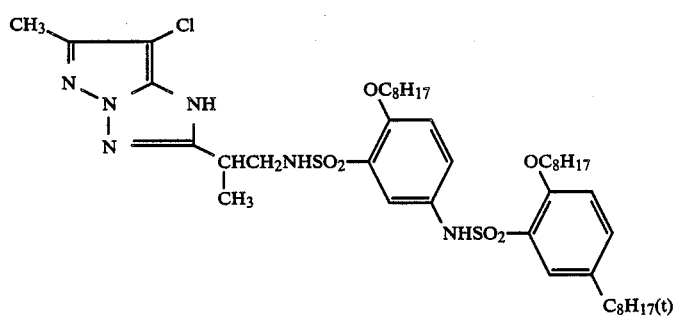
XI-10
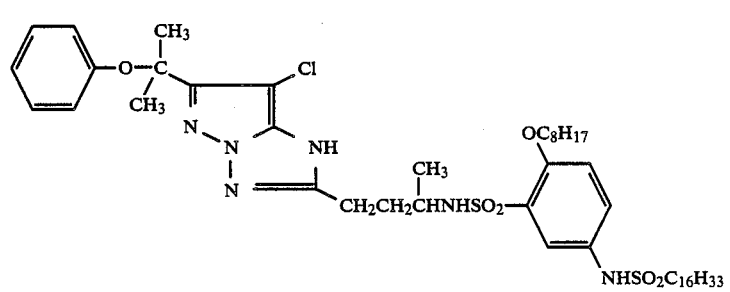
XI-11

-continued
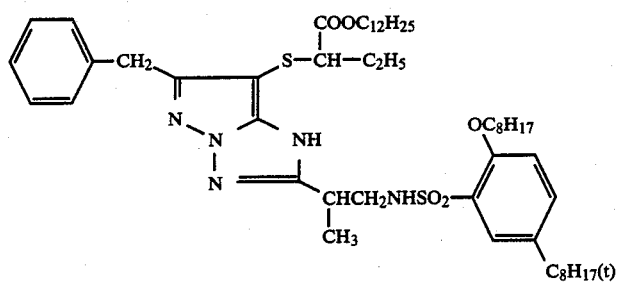
XI-12
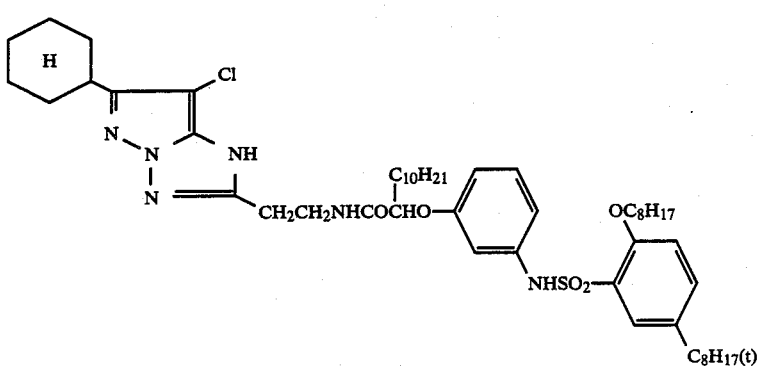
XI-13
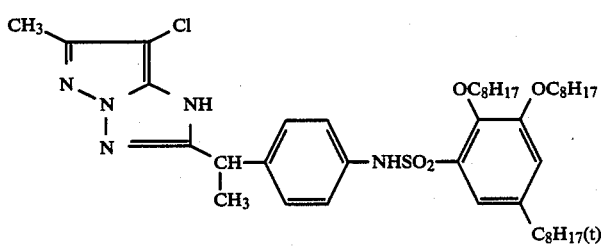
XI-14
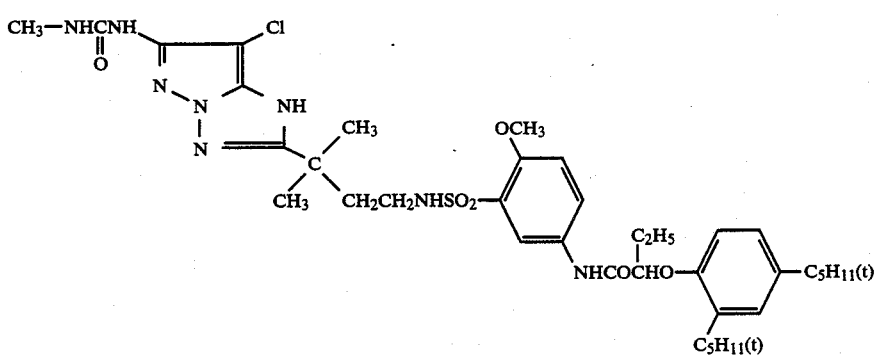
XI-15
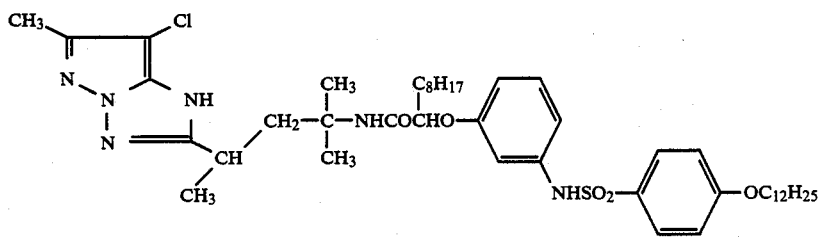
XI-16

-continued
XI-17
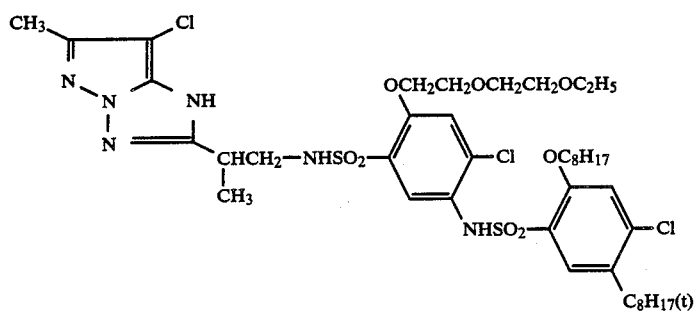
XI-18
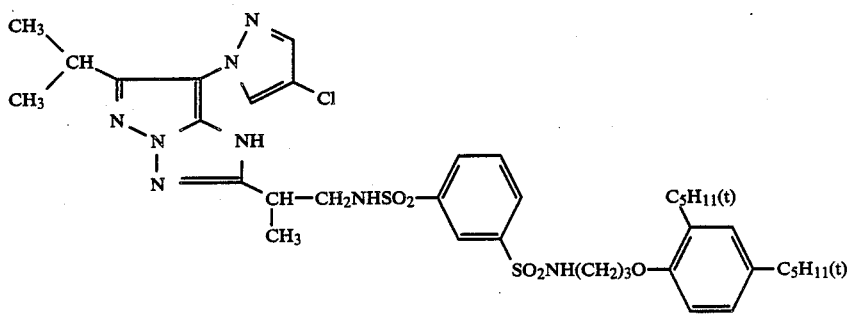
XI-19
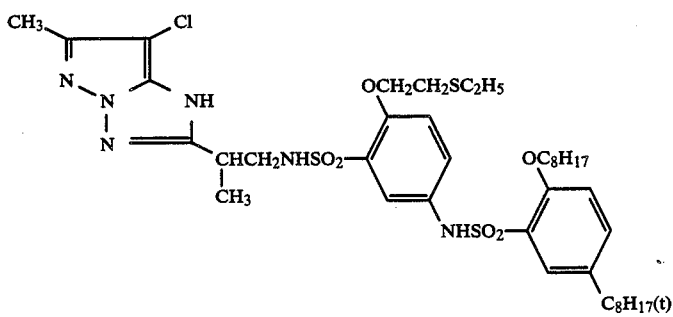
XI-20
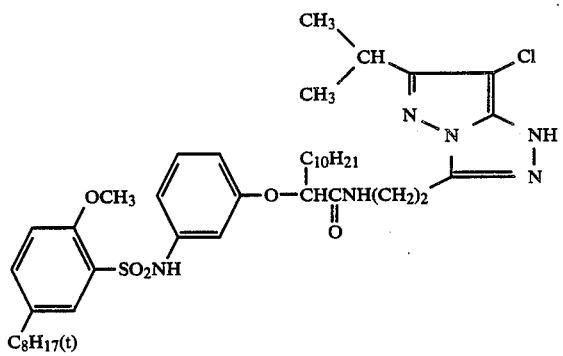
XI-21
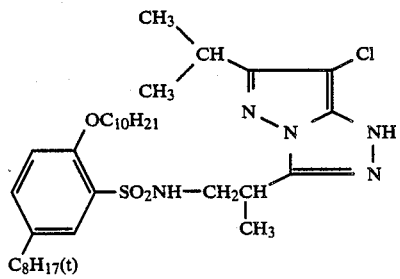

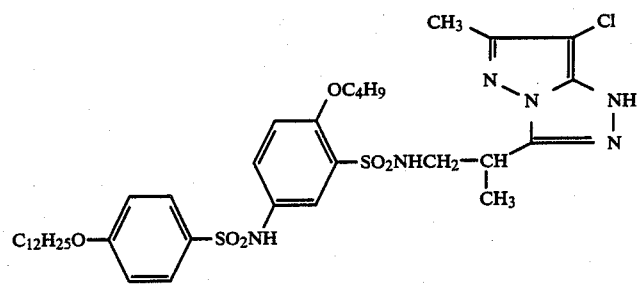
XI-22
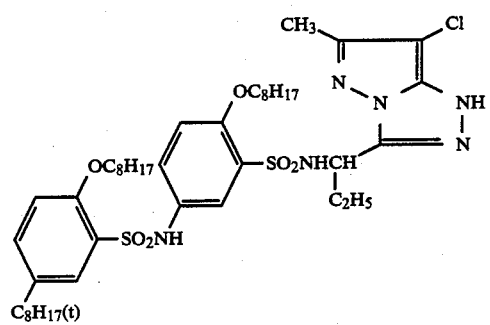
XI-23
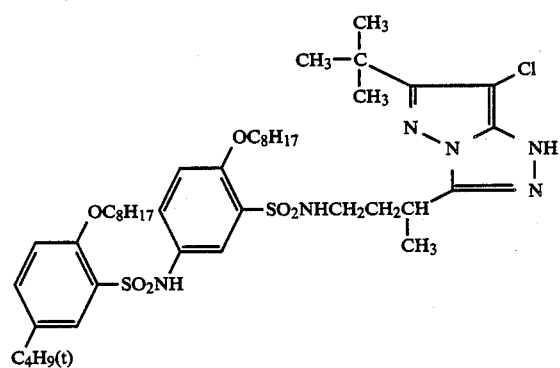
XI-24
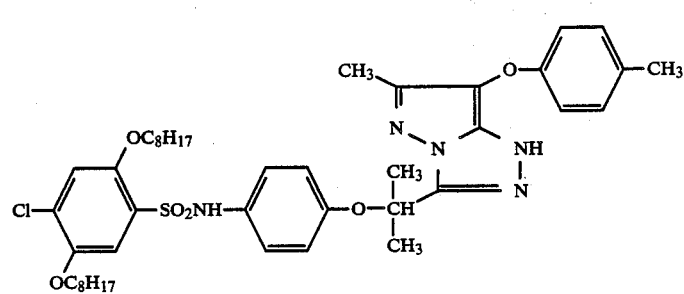
XI-25
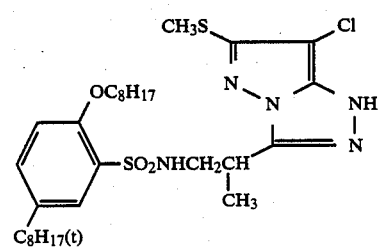
XI-26

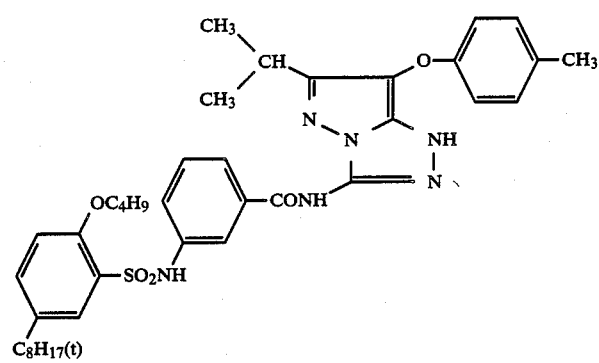
XI-27
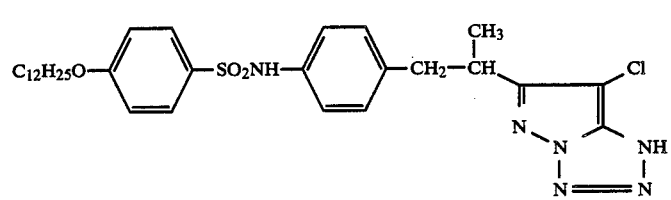
XI-28
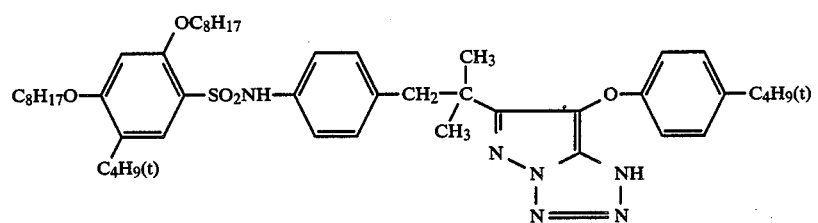
XI-29
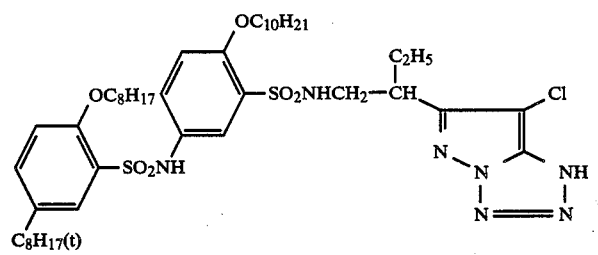
XI-30
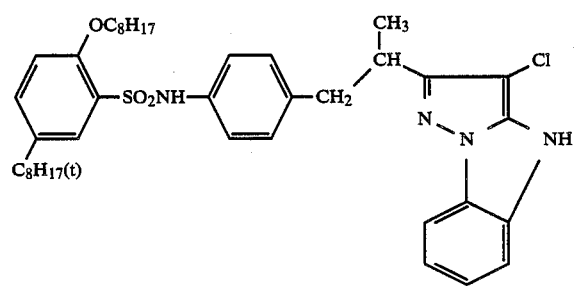
XI-31

XI-32

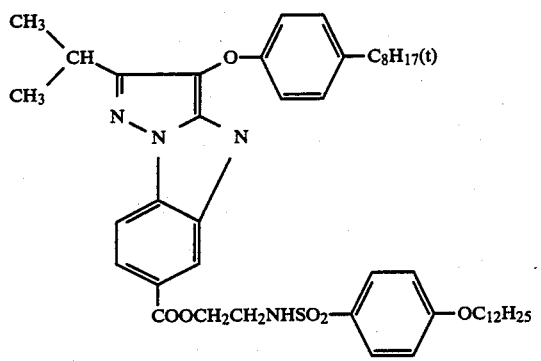

XI-33

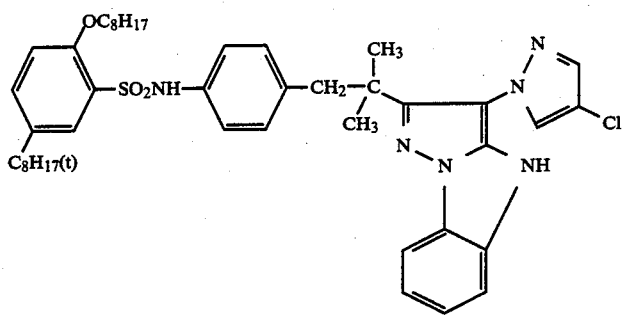

XI-34

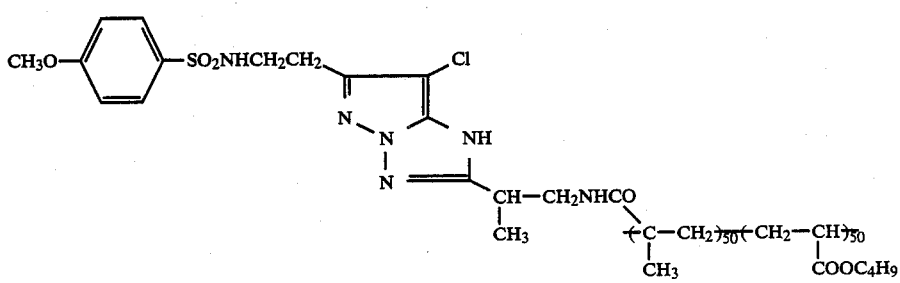

XI-35

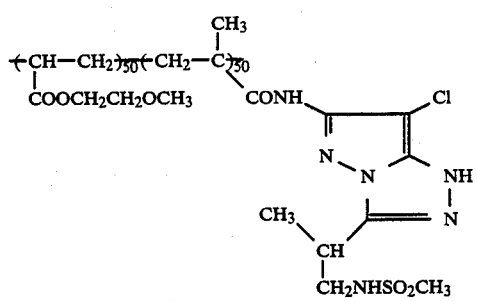

The pyrazoloazole series magenta couplers represented by general formulae [XI - 1] to [XI - 5] can be prepared according to the methods described in the following literatures.

That is, the couplers shown by general formula [XI - 1] can be prepared by the methods described by Japanese Patent Application (OPI) No. 162,548/84, the couplers shown by general formula [IX - 2] can be prepared by the methods described in Japanese Patent Application (OPI) No. 171,956/84, the couplers shown by general formula [XI - 3] can be prepared by the methods of U.S. Pat. No. 3,725,067, etc., the couplers shown by general formula [XI - 4] can be prepared by the methods of Japanese Patent Application (OPI) No. 33,552/85, etc., and the couplers shown by general formula [XI - 5] can be prepared by the methods of U.S. Pat. Nos. 3,061,432, 3,369,897, etc.

Then, synthesis examples of the typical magenta couplers for use in this invention are illustrated below.

Synthesis Example 1.

Synthesis of 7-chloro-6-methyl-2-{1-methyl-2-(2-octyloxy-5-tert-octylbenzenesulfonamido)ethyl}-1H-pyrazolo-[1,5-b][1,2,4]triazole (Coupler X-7):

Synthesis Scheme

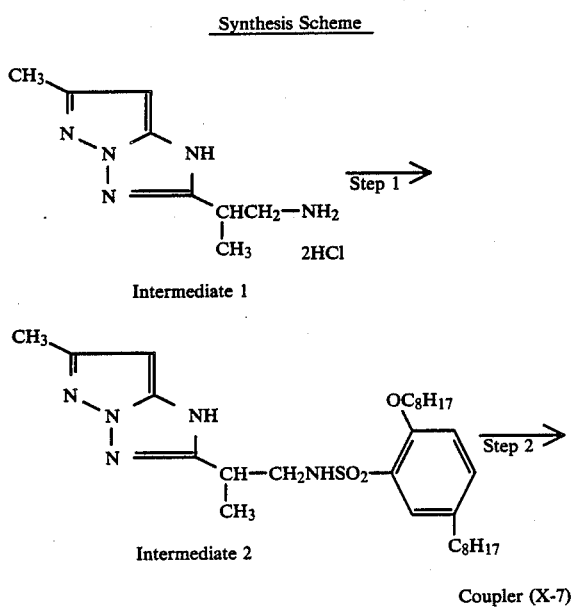

Coupler (X-7)

(1) Synthesis of Intermediate 2:

In 150 ml of a mixed solvent of acetonirtile and dimethylacetamide (mixing ratio of 1:1 by volume) was dissolved 21.7 g of Intermediate 1 synthesized by the same method as that described in Japanese Patent Application No. 101,730/85 and after adding thereto 30 g of triethylamine, the mixture was cooled below 10° C. Then, 48 g of 2-octyloxy-5-tert-octylbenzenesulfonyl chloride was gradually added dropwise to the mixture and then the mixture was stirred for one hour. Then, 300 ml of ethyl acetate was added to the reaction mixture and after washing the mixture twice with 200 ml of a saturated aqueous sodium chloride solution, once with 200 ml of an aqueous solution of 2% sodium hydrogencarbonate, and then with 200 ml of a saturated aqueous sodium chloride solution, the ethyl acetate phase formed was collected, dried by 20 g of anhydrous sodium sulfate, and concentrated under reduced pressure to provide 50.5 g of an oily residue (Intermediate 2).

(2) Synthesis of Coupler (X - 7):

In 300 ml of methylene chloride was dissolved 2.47 g of Intermediate 2 obtained in the above step and while stirring the mixture at room temperature, 12 g of N-chlorosuccinic acid imide was added thereto in five-split parts. After stirring the mixture for 2 hours at room temperature, succinic acid imide precipitated was filtered off and the filtrate thus formed was concentrated. The residue was dissolved well in 300 ml of ethyl acetate, the solution was washed twice with a saturated aqueous sodium chloride solution, dried by 20 g of anhydrous sodium sulfate, and concentrated. The residue thus formed was crystallized from acetonitrile to provide 44 g of the colorless crystals of the desired coupler having melting point of 135° C. to 137° C.

Elemental Analysis for $C_{30}H_{48}N_5ClSO_3$ (594.25)

|  | C | H | N |
|---|---|---|---|
| Calculated: | 60.6% | 8.14% | 11.8% |
| Found: | 60.4% | 8.15% | 11.8% |

Synthesis Example 2.

Synthesis of 7-chloro-6-methyl-2-[1-methyl-2-{2-octyloxy-5-(2-octyloxy-5-tert-octylbenzenesulfonamido)benzenesulfonamido}ethyl]-1H-pyrazolo[1,5-b]-[1,2,4]triazole (Coupler X - 10):

By reacting Intermediate 1 in Synthesis Example 1 above and 2-octyloxy-5-(2-octyloxy-5-tert-octylbenzenesulfonamido)benzenesulfonyl chloride and then chlorinating the product with N-chlorosuccinic acid imide as in Synthesis Example 1, colorless crystals of Coupler 10 having melting point of 129° C. to 131° C. (crystallized from solution of hexane and ethyl acetate of 5:1) was obtained.

Elemental Analysis for $C_{44}H_{69}N_6O_6ClS_2$ (877.66)

|  | C | H | N |
|---|---|---|---|
| Calculated: | 60.2% | 7.92% | 9.58% |
| Found: | 60.1% | 7.93% | 9.59% |

Then, the nitrogen-containing heterocyclic rings which give desired advantages when used together with the magenta coupler shown by general formula [XI] described above in this invention are explained below.

That is, the nitrogen-containing heterocyclic rigs are represented by general formulae [XII] [XIIIa], [XIIIb], [XIV], [XV], [XVIa] and [XVb] described hereinbelow.

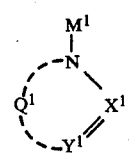 [XII]

wherein, $X^1$ and $Y^1$ each represents a carbon atom or a nitrogen atom; $Q^1$ represents an atomic group necessary for forming a 5-membered or 6-membered heterocyclic ring, which may be condensed; and $M^1$ represents a hydrogen atom or a cation such as an alkali metal ion (e.g., sodium ion, potassium, etc.), an ammonium ion, etc.

Now, examples of the heterocyclic ring shown by $Q^1$ are triazole, imidazole, benzotriazole, naphthotriazole, azabenzotriazole, benzimidazole, naphthimidazole, azabenzimidazole, indazole, etc. Benzotriazole is particularly preferred.

These heterocyclic rings (including condensed rings) may be substituted by substituents. The substituents preferably include the same substituents for the heterocyclic ring nuclei disclosed at page 117 to 118 of this specification.

Specific examples nuclei of the preferred heterocyclic rings shown by general formula [XII] described above are shown below.

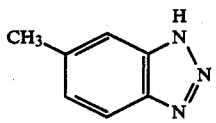　XII-1

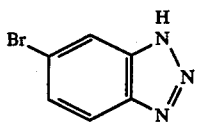　XII-2

The nitrogen containing heterocyclic rings represented by general formulae [XIIIa] and [XIIIb] are shown below.

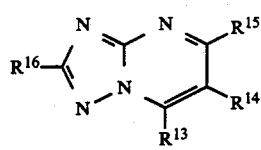　[XIIIa]

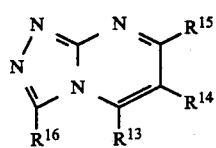　[XIIIb]

wherein, $R^{13}$, $R^{14}$, $R^{15}$, and $R^{16}$, which may be the same or different, each represents a hydrogen atom; a substituted or unsubstituted alkyl group preferably containing 1 to 20 carbon atoms in the alkyl moiety; a substituted or unsubstituted aryl group, preferably containing 6 to 20 carbon atoms; a substituted or unsubstituted amino group; a hydroxy group; an alkoxy group, preferably containing 1 to 20 carbon atoms in the alkoxy moiety; an alkylthio group preferably containing 1 to 20 carbon atoms in the alkyl moiety; a substituted or unsubstituted carbamoyl group; a halogen atom; a cyano group; a carboxy group, preferably containing 1 to 12 carbon atoms; an alkoxycarbonyl group, preferably containing 2 to 22 carbon atoms; or a heterocyclic group, preferably being 5-membered or 6-membered ring or a condensed ring thereof containing at least one of S, N and O atoms, said $R^{13}$ and $R^{14}$ or $R^{15}$ may combine together to form a 5-membered or 6-membered ring; at least one of said $R^{13}$ and $R^{15}$ being a hydroxy group. The substituents above described preferably include the same substituents for the group $R^{23}$ or $R^{24}$ disclosed at pages 115 to 116 of this specification.

Specific examples of the compounds shown by general formula [XIIa] or [XIIIb] described above are illustrated below.

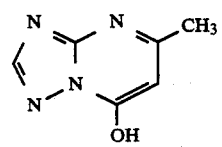　XIIIa-1

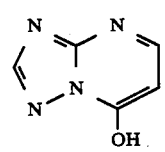　XIIIa-2

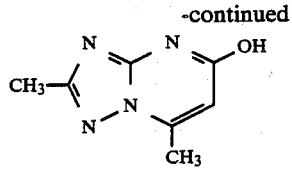　XIIIa-3

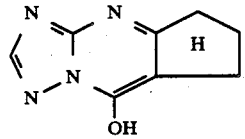　XIIIa-4

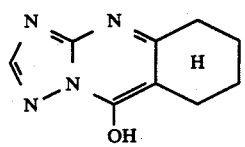　XIIIa-5

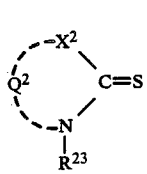　[XIV]

wherein, $R^{23}$ represents a substituted or unsubstituted alkyl group, a substituted or unsubstituted aralkyl group, a substituted or unsubstituted alkenyl group, a substituted or unsubstituted aryl group, or a substituted or unsubstituted heterocyclic group; $X^2$ represents O, S, Se or $NR^{24}$ (wherein, $R^{24}$ represents a substituted or unsubstituted alkyl group, a substituted or unsubstituted aralkyl group, a substituted or unsubstituted alkenyl group, a substituted or unsubstituted aryl group, or a substituted or unsubstituted heterocyclic group and $R^{24}$ may be the same as $R^{23}$); and $Q^2$ represents an atomic group necessary for forming a 5-membered or 6-membered heterocyclic ring, which may be condensed).

Then, the thion type antifogging agents shown by above formula [XIV] are explained below in detail.

In general formula [XIV], the alkyl group shown by $R^{23}$ and $R^{24}$ includes an alkyl group having 1 to 20 carbon atoms (e.g., a methyl group, an ethyl group, a butyl group, a hexyl group a dodecyl group, etc.,) and also includes substituted alkyl groups. Examples of the substituent are a halogen atom (e.g., a chlorine atom), a cyano group, a carboxy group, a hydroxy group, an acyloxy group having 2 to 6 carbon atoms (e.g., an acetoxy group, etc.,), an alkoxycarbonyl group having 2 to 22 carbon atoms (e.g., an ethoxycarbonyl group, a butoxycarbonyl group, etc.,), a carbamoyl group, a sulfamoyl group, a sulfo group, an amino group, a substituted amino group, etc.

The alkenyl group shown by $R^{23}$ and $R^{24}$ includes a benzyl group, a phenetyl group, etc.

The alkenyl group shown by $R^{23}$ and $R^{24}$ includes an allyl group, etc.

The aryl group shown by $R^{23}$ and $R^{24}$ is a monocyclic or dicyclic, preferably monocyclic aryl group, which may be substituted and examples of the substituent for the aryl group are an alkyl group having 1 to 20 carbon atoms (e.g., a methyl group, an ethyl group, a nonyl group, etc.,), an alkoxy group having 1 to 20 carbon atoms (e.g., a methoxy group, an ethoxy group, etc.,), a hydroxy group, a halogen atom (e.g., a chlorine atom, a bromine atom, etc.,), a carboxy group, a sulfo group, etc.

The 5-membered or 6-membered heterocyclic ring shown by $Q^2$ in general formula [XIV] includes a thiazoline ring, a thiazolidine ring, a selenazoline ring, an oxazoline ring, an oxazolidine ring, an imidazoline ring, an imidazolidine ring, a 1,3,4-thioazoline ring, a 1,3,4-oxadiazoline ring, a 1,3,4-triazoline ring, a tetrazoline ring, a pyrimidine ring, etc.

These heterocyclic rings as a matter of course include the rings to which a 5-membered, 6-membered, or 7-membered carbon ring or a heterocyclic ring is condensed. That is, they also include a benzothiazoline nucleus, a naphthothiazoline nucleus, a dihydronaphthothiazoline nucleus, a tetrahydrobenzothiazoline nucleus, a benzoselenazoline nucleus, a benzoxazoline nucleus, a naphthoxazoline nucleus, a benzimidazoline nucleus, a dihydroimidazolopyrimidine nucleus, a dihydrotriazolopyridine nucleus, a dihydrotriazolopyrimidine nucleus, etc.

These heterocyclic ring nuclei each may have a substituent. Examples of the substituent are an alkyl group having 1 to 20 carbon atoms (e.g., a methyl group, etc.,), an alkoxy group having 1 to 20 carbon atoms (e.g., a methoxy group, etc.,), an alkylthio group having 1 to 20 carbon atoms (e.g., a methylthio group, etc.,), a hydroxy group, a substituted or unsubstituted amino group (e.g., a dimethylamino group, an acylamino group such as an acetylamino group, etc.,), an aryl group (e.g., a phenyl group, etc.,), an alkenyl group having 2 to 20 carbon atoms (e.g., an allyl group, etc.,), an aralkyl group (e.g., a benzyl group, etc.,), a halogen atom (e.g., chlorine, bromine, etc.,), a cyano group, a carboxy group, a sulfo group, a carbamoyl group (e.g., a carbamoyl group, a methylcarbamoyl group, etc.,), an alkoxycarbonyl group having 2 to 22 carbon atoms (e.g., a methoxycarbonyl group, etc.,), an aryloxycarbonyl group (e.g., a phenoxycarbonyl group, etc.,), an alkylcarbonyl group having 2 to 22 carbon atoms (e.g., an acetyl group, etc.,), etc.

Then, specific examples of the thion type antifoggant represented by above-described general formula [XIV] are shown below.

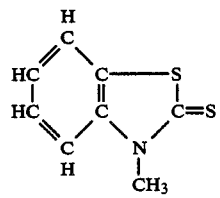

(XIV-1)

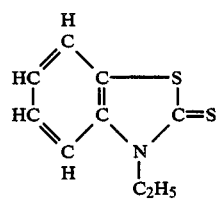

(XIV-2)

-continued

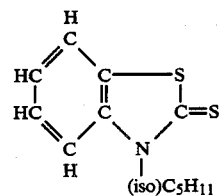

(XIV-3)

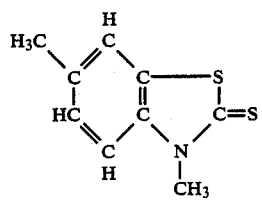

(XIV-4)

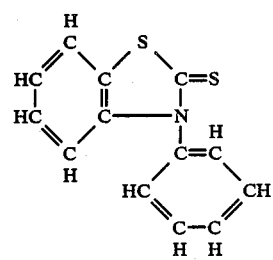

(XIV-5)

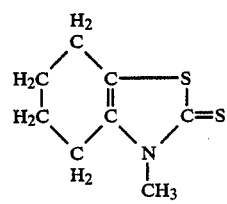

(XIV-6)

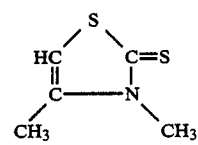

(XIV-7)

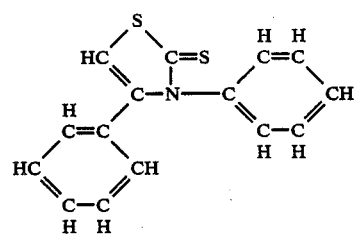

(XIV-8)

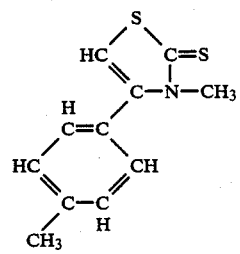

(XIV-9)

-continued

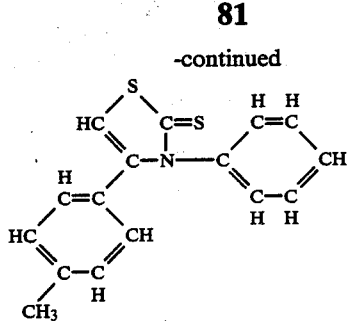 (XIV-10)

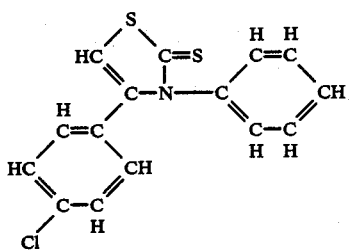 (XIV-11)

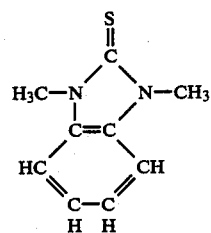 (XIV-12)

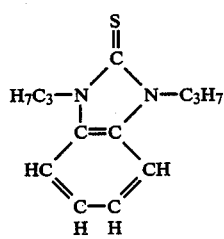 (XIV-13)

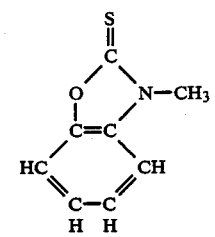 (XIV-14)

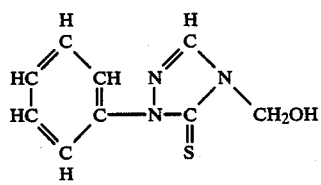 (XIV-15)

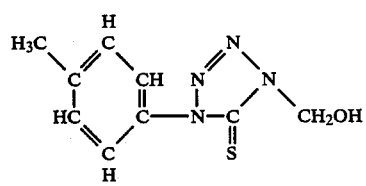 (XIV-16)

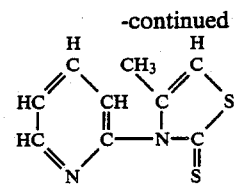 (XIV-17)

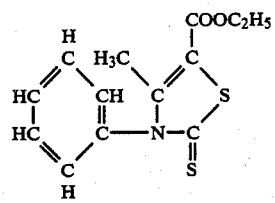 (XIV-18)

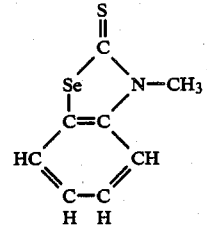 (XIV-19)

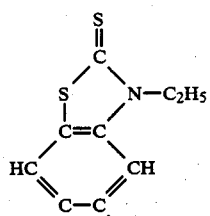 (XIV-20)

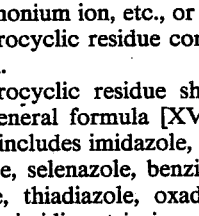 (XIV-21)

$$Z^1-S-M^2 \qquad [XV]$$

wherein, $M^2$ represents a hydrogen atom, a cation, such as an alkali metal ion (e.g., sodium ion, potassium ion, etc.) an ammonium ion, etc., or $-S-Z^1$; and $Z^1$ represents a heterocyclic residue containing at least one nitrogen atom.

The heterocyclic residue shown by $Z^1$ in above-described general formula [XV] may be further condensed and includes imidazole, triazole, tetrazole, thiazole, oxazole, selenazole, benzimidazole, benzoxazole, benzthiazole, thiadiazole, oxadiazole, benzselenazole, pyrazole, pyrimidine, triazine, pyridine, naphthothiazole, naphthimidazole, naphthoxazole, azabenzimidazole, purine, azaindene (e.g., triazaindene, tetraazaindene, pentaazaindene, etc.,), etc.

Also, these heterocyclic ring residues and condensed rings may be substituted by a proper substituent. Examples of the substituent are an alkyl group (e.g., a methyl group, an ethyl group, a hydroxyethyl group, a trilfuoromethyl group, a sulfopropyl group, a dipropylaminoethyl group, an adamantyl. group, etc.,), an alkenyl group (e.g., an allyl group, etc.,), an aralkyl group (e.g., a benzyl group, a p-chlorophenetyl group, etc.,), an aryl group (e.g., a phenyl group, a naphthyl group, a p-carboxyphenyl group, a 3,5-di-carboxyphenyl group, a m-sulfophenyl group, a p-acetamidophenyl group, a 3-capramidophenyl group, a p-sulfamoylphenyl group, a m-hydroxyphenyl group, a p-nitrophenyl group, a 3,5-dichlorophenyl group, a 2-methoxyphenyl group, etc.,), a heterocyclic ring residue (e.g., pyridine furan thiophene, etc.,),a halogen atom (e.g., chlorine atom, a bromine atom, etc.,), a mercapto group, a cyano group, a carboxy group, a sulfo group, a hydroxy group, a carbamoyl group, a sulfamoyl group, an amino group, a nitro group, an alkoxy group (e.g., a methoxy group, etc.,), an aryloxy group (e.g., a phenoxy group, etc.,), an acyl group (e.g., an acetyl group, etc.,), an acylamino group (e.g., an acetylamino group, a capramido group, a methylsulfonylamino group, etc.,), a substituted amino group (e.g., a diethylamino group, a hydroxyamino group, etc.,), an alkylthio or arylthio group (e.g., a methylthio grup, a carboxylethylthio group, a sulfobutylthio group, etc.,), an alkoxycarbonyl group (e.g., a methoxycarbonyl group, etc.,), an aryloxycarbonyl group (e.g., a phenoxycarbonyl group, etc.,), etc.

Then, specific examples of the mercapto compound shown by general formula [XV] described above are illustrated below.

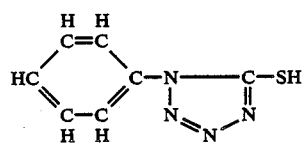

(XV-1)

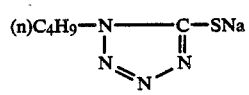

(XV-2)

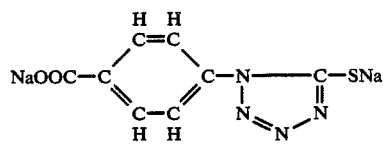

(XV-3)

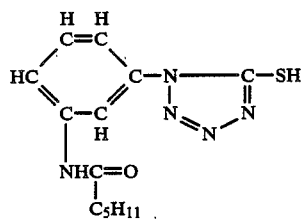

(XV-4)

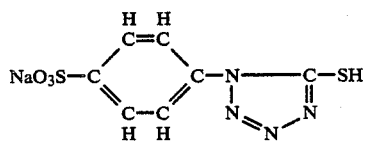

(XV-5)

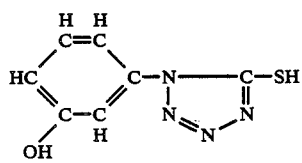

(XV-6)

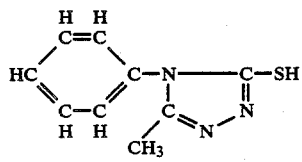

(XV-7)

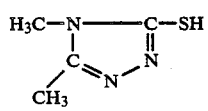

(XV-8)

-continued
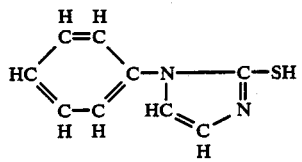 (XV-9)
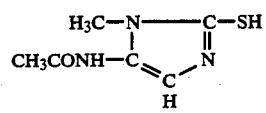 (XV-10)
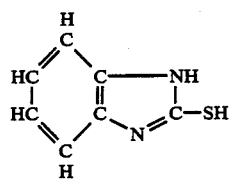 (XV-11)
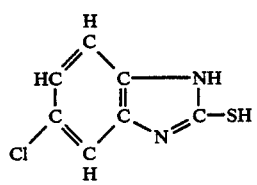 (XV-12)
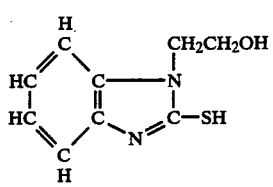 (XV-13)
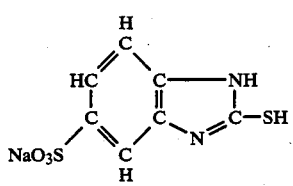 (XV-14)
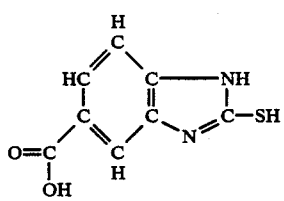 (XV-15)
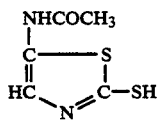 (XV-16)
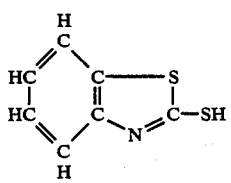 (XV-17)

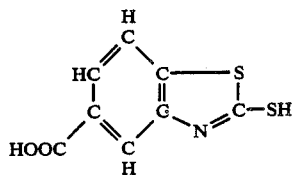 (XV-18)
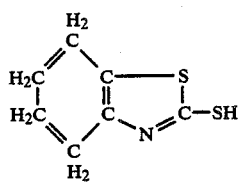 (XV-19)
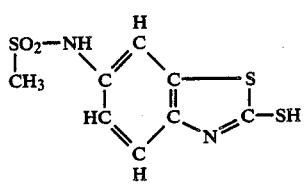 (XV-20)
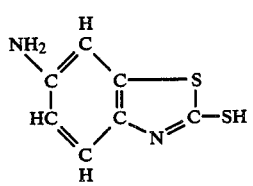 (XV-21)
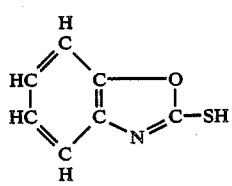 (XV-22)
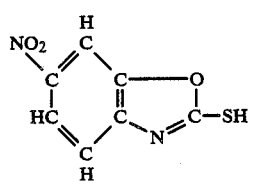 (XV-23)
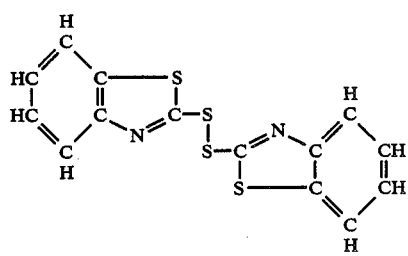 (XV-24)
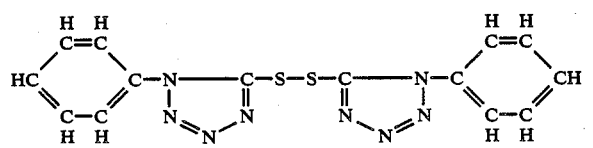 (XV-25)
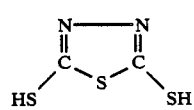 (XV-26)

-continued
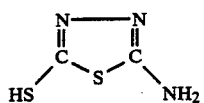 (XV-27)
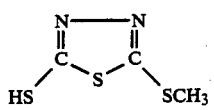 (XV-28)
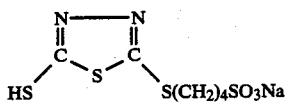 (XV-29)
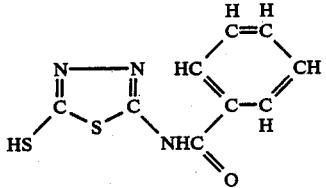 (XV-30)
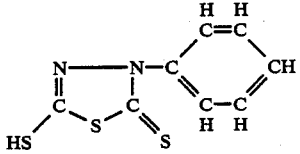 (XV-31)
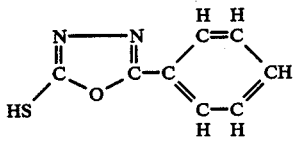 (XV-32)
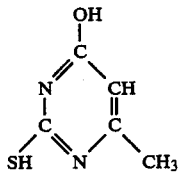 (XV-33)
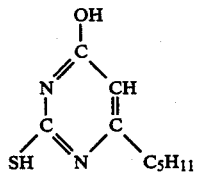 (XV-34)
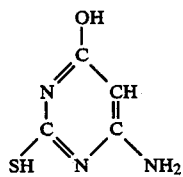 (XV-35)
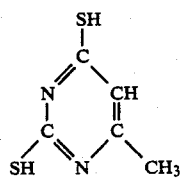 (XV-36)

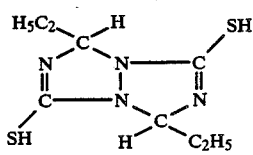 (XV-37)

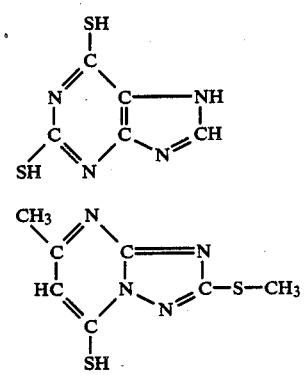 (XV-38)

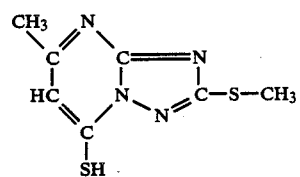 (XV-39)

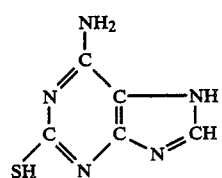 (XV-40)

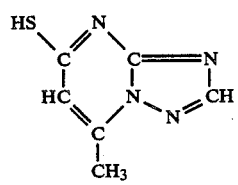 (XV-41)

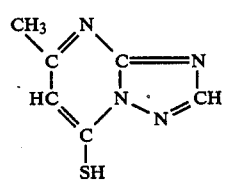 (XV-42)

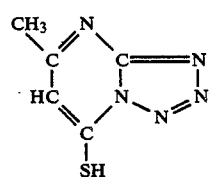 (XV-43)

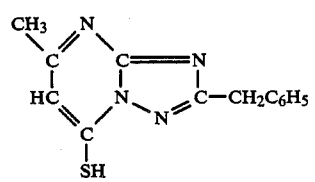 (XV-44)

Also, in other embodiment of the silver halide color photographic materials of this invention, the deterioration in photographic properties of the photographic light-sensitive materials by the regression of latent images can be effectively prevented by using the compound represented by general formula [XVIa] or [XVIb] described below together with the magenta coupler shown by general formula [XI] described above.

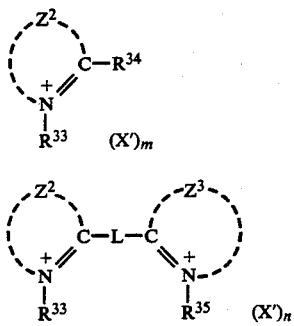
[XVIa]

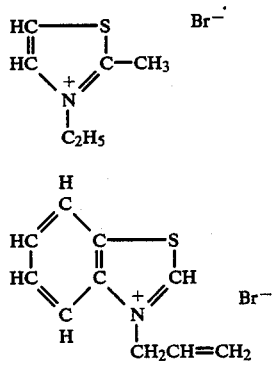
[XVIb]

wherein, $Z^2$ and $Z^3$ each represents an atomic group necessary for forming an imidazole ring, a pyridine ring, a thiazole ring or a selenzole ring and they may be combined; $R^{33}$ and $R^{35}$ each represents a substituted or unsubstituted alkyl group, a substituted or unsubstituted alkenyl group, a substituted or unsubstituted aralkyl group, or a substituted or unsubstituted aryl group; $R^{34}$ represents a hydrogen atom or a substituted or unsubstituted alkyl group the alkyl moiety preferably having 1 to 20 carbon atoms; said $R^{33}$ and $R^{34}$ may form a ring; L represents a divalent linkage group; X' represents an acid anion; m represents 0 or 1, and n represents 0, 1 or 2.

The alkyl group, alkenyl group, aralkyl group and aryl group represented by $R^{33}$ and $R^{35}$ are the same as those for $R^{23}$ disclosed at pages 115 to 116.

Specific examples of the compound shown by general formula [XVIa] described above are illustrated below.

[XVIa-1]

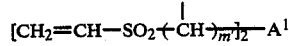
[XVIa-2]

Also, in still other embodiment of this invention, silver halide color photographic materials having improved storage stability or shelf life and giving color images having improved color purity can be obtained by using vinylsulfone type hardening agent represented by general formula [XVII] described below together with the magenta coupler shown by general formula [XI] described above (wherein, it is particularly preferred that at least one of $R^1$ and $R^2$ is a sulfoamidoalkyl group or a sulfamoylalkyl group);

$$(CH_2=CH-SO_2)_{\overline{n}}Y^2 \qquad [XVII]$$

wherein, $Y^2$ represents a n-valent group and n represents 2 or an integer larger than 2.

The vinylsulfone type hardening agent shown by general formula [XII] described above may exists in the silver halide emulsion layer containing the magenta coupler shown be general formula [XI] described above or may exist in any other layer. Furthermore, the above-described hardening agent may exist in two or more layers of the silver halide color photographic material of this invention.

It is preferred that the addition amount of the hardening agent shown by general formula [XVII] is about 0.01 to 10% by weight, in particular, about 0.1 to 4% based on the total coated gelatin amount.

Particularly preferred compounds in the hardening agents shown by general formula [XVII] are represented by following general formula [XVIIa], [XVIIb], or [XVIIc].

$$(CH_2=CH-SO_2)_{\overline{2}}Y^3 \qquad [XVIIa]$$

wherein, $Y^3$ represents an alkyl group having 1 to 12 carbon atoms.

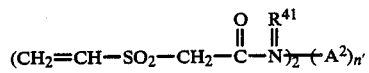
[XVIIb]

wherein, $R^{40}$ represents a hydrogen atom or an alkyl group having at most 3 carbon atoms (plural $R^{40}$s may be the same or different); $A^1$ represents a heterocyclic group; and m' represents an integer of 1 to 4.

$$(CH_2=CH-SO_2-CH_2-\overset{O}{\overset{\|}{C}}-N)_{\overline{2}}(A^2)_{n'} \qquad [XVIIc]$$

wherein, $R^{41}$ presents a hydrogen atom or an alkyl group having 1 to 4 carbon atoms (plural $R^{41}$s may be the same or different); $A^2$ represents a di-valent group; and n' represents 0 or 1.

Then, specific examples of the vinylsulfone compounds shown by general formula [XVIIa], [XVIIb], and [XVIIc] described above are illustrated below.

$$CH_2=CH-SO_2-CH_2-CH_2-SO_2-CH=CH_2 \qquad [XVII-1]$$

$$CH_2=CH-SO_2-CH_2-CH_2-CH_2-SO_2-CH=CH_2 \qquad [XVII-2]$$

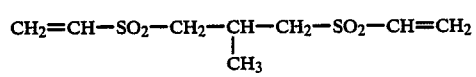
[XVII-3]

$$CH_2=CH-SO_2-CH_2-O-CH_2-SO_2-CH=CH_2 \qquad [XVII-4]$$

$$CH_2=CH-SO_2-CH_2-S-CH_2-SO_2-CH=CH_2 \qquad [XVII-5]$$

$$(CH_2=CH-SO_2-CH_2-CONH)_{\overline{2}} \qquad [XVII-6]$$

$$(CH_2=CH-SO_2-CH-CONH-CH_2)_{\overline{2}} \qquad [XVII-7]$$

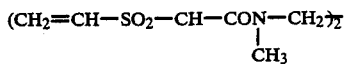 [XVII-8]

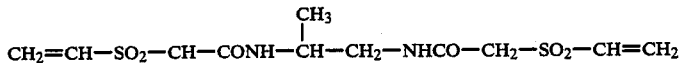 [XVII-9]

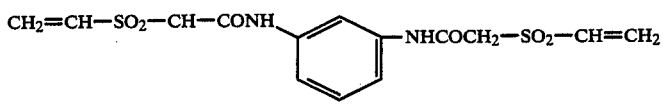 [XVII-10]

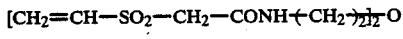 [XVII-11]

Also, in other preferred embodiment of this invention, there is provided a silver halide color photographic material comprising support having thereon at least a green-sensitive silver halide emulsion layer containing a magenta coupler and at least a blue-sensitive silver halide emulsion layer containing a yellow coupler between the green-sensitive emulsion layer and the support, wherein (a) the green-sensitive silver halide emulsion layer contains the pyrazoloazole series magenta coupler represented by general formula [XI] described above, (b) the mean grain size of the silver halide grains (excluding the silver halide fine grains in the silver halide fine grain emulsion described in (c)) of the above-described blue-sensitive emulsion layer is at least 1.2 times the average grain size of the silver halide grains in the above-described green-sensitive emulsion layer, and (c) at least one of the above-described blue-sensitive silver halide emulsion layer and a light-insensitive layer existing between the above-described blue-sensitive silver halide emulsion layer and the green-sensitive silver halide emulsion layer contains a silver halide fine grain emulsion.

Such a silver halide color photographic material of this invention described above forms magenta images having excellent light-absorption characteristics and hence giving color photographic images excellent in color reproducibility.

Also, in the silver halide color photographic materials of this invention, the formation of fogs in the blue-sensitive silver halide emulsion layers, which is a trouble in the case of using a conventional pyrazoloazole series magenta coupler, can be inhibited. Accordingly, in this invention, color photographic images having low density at high-light portions particularly having low minimum density of yellow and being excellent in excellent whiteness of background are obtained. Furthermore, the silver halide color photographic materials of this invention give excellent effects that they show stable photographic performance to various deviations of development conditions.

It has not yet been clarified in this invention that the formation of fogs in the blue-sensitive silver halide emulsion containing the yellow coupler is inhibited by what kind of mechanism. However, it would be considered that fog is formed by the co-action between the magenta coupler for use in this invention and the silver halide in the blue-sensitive silver halide emulsion layer containing a yellow coupler at development and the formation of fog is inhibited by the fine grain silver halide emulsion for use in this invention.

The formation of fog of the blue-sensitive emulsion layer containing such a yellow coupler is liable to occur in a developer having a particularly high pH, less KBr amount, or containing large amount of sodium sulfite. However, by the addition of the fine grain emulsion for use in this invention, the formation of fog in the emulsion can be greatly reduced and hence a light-sensitive material giving less fog for the variation of the developer composition can be proposed.

The grain size of silver halide in the silver halide fine grain emulsion added to the above-described blue-sensitive silver halide emulsion layer or a light-insensitive layer in this invention is properly 0.01 to 0.20 μm and smaller grain size is more preferred.

Also, for the emulsions, silver chloride, silver chlorobromide, or silver bromide can be used but a silver halide emulsion containing at least 50 mol % silver bromide is preferred. Also, for the purpose of quick processing, a silver chlorobromide emulsion having a silver chloride content of at least 80 mol % may be used. The fine grain emulsion may be light sensitive or light insensitive but low sensitive silver halide grains which are substantially not developed can be advantageously used for the objects of this invention. The addition amount of the fine grain emulsion is suitably 0.005 to 0.1 g/m², preferably 0.01 to 0.05 g/m² as silver.

In addition, such low-sensitive fine silver halide grains can be prepared according to the case of preparing ordinary insensitive silver halide emulsions. In this case, the surface of the silver halide grains may not be chemically sensitized or may not be spectrally sensitized.

The silver halide fine grain emulsion is incorporated in a blue-sensitive silver halide emulsion containing yellow coupler or in an insensitive layer existing between the blue-sensitive emulsion layer containing yellow coupler and a green-sensitive silver halide emulsion layer containing the magenta coupler shown by general formula [XI] described above. Also, the fine grain emulsion may be incorporated in two or more layers.

The mean grain size of the silver halide grains (excluding the above-described silver halide fine grains) in the blue-sensitive silver halide emulsion for use in this invention is at least 1.2 times, preferably 1.3 times to 5 times, more preferably 1.5 times to 2 times the mean grain size of the silver halide grains in the green-sensitive silver halide emulsion layer. If the mean grain size is less than 1.2 times, the portion of images to be colored in yellow causes severe color mixing with magenta, while if the mean grain size is over 5 times, an unnecessarily large sensitivity difference occurs between the blue-sensitive emulsion layer and the green-sensitive emulsion layer, which results in causing improper sensitivity balance of layers.

The silver halide grains (excluding the above-described silver halide fine grain emulsion) of the blue-sensitive emulsion layer for use in this invention are particularly preferably silver chlorobromide grains containing 2 mol % or less of iodine ion and at least 70 mol % bromine ion and having a mean grain size of 0.4 to 1.5 $\mu$m, in particular 0.6 to 1.0 $\mu$m as the diameter when the silver halide grains are spherical or as the sphere-corresponding diameter determined by a projected area method when the silver halide grains are not spherical.

The silver halide which is preferably used in this invention does not contain silver iodide or, if contain, at most 10% of silver chloro(iodo)bromide or silver(iodo)bromide containing.

The silver halide grains for use in this invention may have different phase between the inside thereof and the surface layer thereof, may have a junction structure or a multiphase structure, or may have wholly uniform phase throughout the grains except the surface layer thereof. Also, the silver halide grains may be composed of a mixture of different kinds of silver halide grains. For example, in regard to silver chlorobromide grains having different phases, the silver halide grains may have a nucleus or a single layer or plural layers more enriched with silver bromide than the average silver halide composition thereof. Also, the silver halide grains may have a nucleus or single or plural layers more enriched with silver chloride than the average silver halide composition thereof. Furthermore, the mean grain size of the silver halide grains (shown by grain diameter when the grain is sphere or a grain similar to sphere, or by the average value based on the projected area of the grains using the long side length as the grain size when the grain is a cubic grain) for use in this invention is preferably 0.1 to 2$\mu$m, more preferably 0.15 to 1 $\mu$m.

Also, so-called mono-dispersed silver halide emulsion can be preferably used in this invention. It is preferred that the extent of the mono-dispersion is at most 0.15, particularly at most 0.10 by the fluctuation (the value of the standard deviation in the grain size distribution curve of silver halide divided by the mean grain size thereof).

Furthermore, for meeting the gradation required by the color photographic material, two or more kinds of mono-dispersed silver halide emulsions each containing silver halide grains having different grain size may be incorporated in the same silver halide emulsion layer or in multilayers each substantially having the same color sensitivity. Moreover, two or more kinds of poly-dispersed silver halide emulsions or a combination of a mono-dispersed silver halide emulsion and a poly-dispersed silver halide emulsion may be used in mixing or for multilayers.

It is preferred that the silver halide grains for use in this invention have a regular crystal form such as cube, octahedron, dodecahedron, tetradecahedron, etc., but may have an irregular crystal form such as sphere, etc. Also, the silver halide grains may have a composite form by these crystal forms. Furthermore, a tabular grain silver halide emulsion may be used in this invention and in particular, a tabular grain silver halide emulsion in which tabular grains having the aspect ratio of length/thickness is at least 5 account, in particular at least 8 account for at least 50% of the total projected area of the silver halide grains may be used in this invention. Also, the silver halide emulsion for use in this invention may be composed of a mixture of these silver halide emulsions each containing silver halide grains having different crystal form.

The silver halide emulsion for use in this invention may be of a surface latent image type of mainly forming the latent images on the surface thereof or of an inside latent image type of mainly forming the latent images in the inside thereof.

The silver halide photographic emulsions for use in this invention can be prepared using the methods described, for example, in P. Glafkides, *Chimie et Physique Photographique*, published by Paul Montel, 1967, G.F. Duffin, *Photographic Emulsion Chemistry*, published by Focal Press, 1966, V. L. Zelikman et al, *Making and Coating Photographic Emulsion*, Focal Press, 1964, etc.

That is, the silver halide emulsion may be prepared by an acid method, a neutralization method, an ammonia method, etc., or as a method for reacting a soluble silver salt and a soluble halide, a single jet method, a double jet method, or a combination thereof may be used. Also, a so-called reverse mixing method of forming silver halide grains in the existence of excessive silver ions can be used. As one method of the double jet method, a so-called controlled double jet method of keeping a constant pAg of the liquid phase forming the silver halide can be used. By the method, a silver halide emulsion containing silver halide grains having regular crystal form and uniform grain size distribution can be obtained.

Then, additives which are used in the case of producing silver halide emulsions for use in this invention are explained.

At the formation of silver halide grains for use in this invention, a silver halide solvent such as ammonia, potassium rhodanate, ammonium rhodanate, thioether compounds (e.g., those described in U.S. Pat. Nos. 3,271,157, 3,574,628, 3,704,130, 4,297,439, 4,276,374, etc.,), thion compounds (e.g., those described in Japanese Patent Application (OPI) Nos. 144,319/78, 82,408/78, 77,737/80, etc.,), amine compounds (e.g., those described in Japanese Patent Application (OPI) No. 100,717/79, etc.,), etc.

The silver halide photographic materials of this invention can contain color couplers such as cyan couplers, magenta couplers, yellow couplers, etc., and also compounds dispersing couplers.

That is, the silver halide photographic materials of this invention may contain compounds capable of coloring by the oxidative coupling with an aromatic primary amine developing agent (e.g., a phenylenediamine derivative, an aminophenol derivative, etc.,) in color development process. That is, there are acylacetamide couplers (e.g., benzoylacetanilides, pivaloylacetanilides, etc.,), etc., as yellow couplers, and naphthol couplers, phenol couplers, etc., as cyan couplers. As these couplers, it is preferred to use non-diffusible couplers having a hydrophobic group called as ballast group in the molecule. The couplers may be of four equivalent or two equivalent for silver ion. Also, colored couplers having a color correction effect or so-called DIR couplers.releasing a development inhibitor with development may be used in this invention.

Furthermore, in place of DIR couplers, non-coloring DIR coupling compounds which form a colorless product by coupling reaction and release a development inhibitor.

The silver halide photographic emulsions for use in this invention may contain, for example, polyalkylene oxide or the derivatives thereof (e.g., the ethers, esters, amines, etc., thereof), thioether compounds, thiomorpholines, quaternary ammonium salts, urethane derivatives, urea derivatives, imidazole derivatives, 3-pyrrazolidones, etc., for the purposes of sensitivity increase, contrast increase, and development acceleration.

The silver halide photographic emulsions for use in this invention may contain water-soluble dyes (e.g., oxonol dyes, hemioxonol dyes, and merocyanine dyes) as filter dyes or irradiation prevention or other various purposes.

Moreover, the silver halide photographic emulsions may contain cyanine dyes, merocyanine dyes, hemicyanine dyes, etc., before, during or after chemical sensitization as spectral sensitizers or for the purpose of controlling the crystal form or size of silver halide grains.

Also, the silver halide photographic materials for use in this invention may further contain various surface active agents for coating aid, static prevention, the improvement of sliding property, the improvement of dispersibility, sticking prevention, and the improvement of photographic properties (e.g., development acceleration, increase of contrast, increase of sensitivity, etc.,).

The proctive colloids and various additives which are used for the silver halide photographic materials of this invention are described practically in *Research Disclosure*, Vol. 176, RD-17643 (XII, 1978), etc.

The finished silver halide emulsions for use in this invention are coated on a proper support such as a baryta-coated paper, a resin-coated paper, a synthetic paper, triacetate film, a polyethyleneterephthaalte film, a plastic base, and a glass sheet.

This invention can be applied to color photographic positive films, color photographic papers, color photographic negative films, color photographic reversal films, heat-developable light-sensitive materials, light-sensitive materials for color diffusion transfer process, etc.

The light exposure for obtaining photographic images using the photographic light-sensitive materials of this invention can be performed using an ordinary manner. That is, various kinds of light sources such as natural light (sun light), a tungsten, a fluorescent lamp, a mercury lamp, a xenon arc lamp, a carbon arc lamp, a xenon flash lamp, a cathode ray tube, a flying spot, etc. For exposure time, not only an exposure time of from 1/1000 sec. to 1 sec for ordinary camera but also an exposure time shorter than 1/1000 sec., for example $1/10^4$ to $1/10^6$ sec. in the case of using a xenon flash lamp or a cathode ray tube can be used in this invention. Also, an exposure time longer than 1 sec. may be used.

If necessary, the spectral composition of light for use of the light exposure can be controlled using color filter(s). Furthermore, laser light can be used for the light exposure. Also, light emitted from phosphor excited by electron beam, X-rays, $\gamma$-rays, $\alpha$-rays, etc., may be used as the light source for exposing the photographic light-sensitive materials of this invention.

For the color photographic processing of the photographic light-sensitive materials of this invention, the processes and processing liquids described, for example, in *Research Disclosure*, Vol. 176, pages 28-30(RD-17643) can be employed. Also, so-called washless processing or stabilization processing can be employed. The photographic process for processing the photographic light-sensitive materials of this invention includes the case of applying color photographic processing, i.e., photographic processing of forming dye images with a combination of black and white photographic processing, i.e., photographic processing of forming silver images, according to purposes.

The processing temperature is selected in the range of 18° C. to 50° C. but may be lower than 18° C. or over 50° C.

Then, the invention is explained more practically by the examples but the invention is not limited to these examples.

p Example 1

In 18.5 g of tri)2-ethylhexyl) phosphate and 25 ml of ethyl acetate was dissolved 8.9 g of Coupler (M - 1) shown above under heating and the solution obtained was added to 100 ml of an aqueous solution containing 10 g of gelatin and 1.0 g of sodium dodecylbenzenesulfonate followed by stirring at high speed to provide a finely emulsified dispersion of the above-described coupler. The whole amount of the emulsified dispersion was added to 100 g (containing 8.8 g of silver) of silver chlorobromide emulsion containing 50 mol % bromine, after adding thereto 10 ml of 2% solution of dihydroxy-6-chlor-s-triazine sodium salt as a hardening agent, the mixture was coated on a paper support having polyethylene coated layer on both surfaces thereof at a silver coverage of 200 mg/m², and then a gelatin layer was formed on the coated layer to provide Sample A.

Then, Samples B, C, D, E, F, G, and H were produced by the following the same procedure as the case of producing Sample A by using Couplers (M - 2), (M - 5), (M - 7), (M - 9), (M - 11), (M - 13), and (M - 14), respectively in place of Coupler (M - 1).

Moreover, Samples I and J were also produced by following same manner as above using an equimolar amount of Coupler a and Coupler b shown below, respectively, as comparison couplers in place of Coupler (M - 1)

Comparison Coupler a

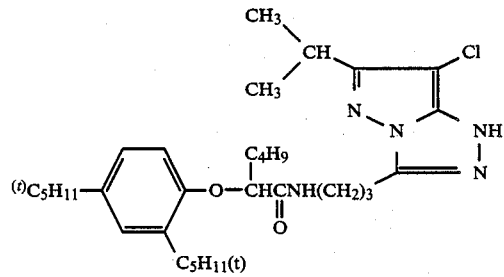

Comparison Coupler b

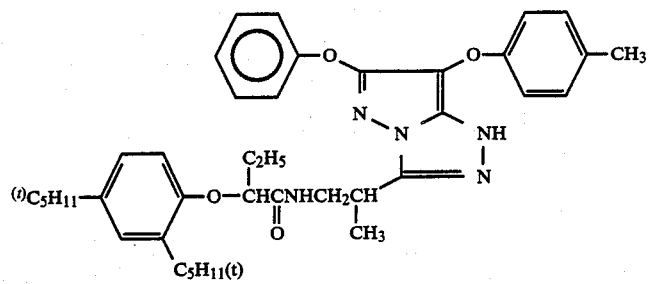

Each of these ten kinds of samples was wedge-exposed at 1,000 CMS and then processed by following processing liquids to obtain magenta colored images.

| Developer | |
|---|---|
| Nitorilotriacetic Acid 3Na | 2.0 g |
| Benzyl Alcohol | 15 ml |
| Diethylene Glycohol | 10 ml |
| Sodium Sulfite | 2.0 g |
| Potassium Bromide | 0.5 g |
| Hydroxylamine Sulfate | 3.0 g |
| 4-Amino-3-methyl-N—ethyl-N—[β-(methanesulfonamido)ethyl]-p-phenylenediamine Sulfate | 5.0 g |
| Sodium Carbonate (monohydrate) | 30 g |
| Water to make | 1 liter (pH 10.1) |
| Blix Solution | |
| Ammonium Thiosulfate (70 wt. %) | 150 ml |
| Sodium Nitrate | 15 g |
| $NH_4[Fe(EDTA*)]$ | 55 g |
| EDTA · 2Na | 4 g |
| Water to make | 1 liter (pH 6.9) |

| Processing Step | Temperature | Time |
|---|---|---|
| Color Development | 33° C. | 3 min. 30 sec. |
| Blix | 33° C. | 1 min. 30 sec |
| Wash | 28 to 35° C. | 3 min. |

EDTA: Ethylenediamine tetraacetic acid

The magenta images of each sample thus obtained were sharp and had high saturation. The photographic properties of these color images were measured and the results obtained are shown in Table 1.

TABLE 1

| | (Photographic Characteristics) | | |
|---|---|---|---|
| Sample | Sensitivity* | Gradation | Maximum Sensitivity |
| A | 100 | 3.06 | 3.07 |
| B | 104 | 3.08 | 3.08 |
| C | 102 | 3.05 | 3.06 |
| D | 99 | 3.06 | 3.09 |
| E | 105 | 3.11 | 3.13 |
| F | 103 | 3.10 | 3.12 |
| G | 98 | 3.09 | 3.11 |
| H | 101 | 3.12 | 3.06 |
| I | 93 | 2.96 | 2.98 |
| J | 92 | 2.93 | 2.95 |

Samples A to H: Samples of this invention
Samples I and J: Comparison samples
(*): The relative value of the reciprocal of the exposure amount giving the density of (fog + 0.5). The sensitivity of Sample A in this invention was used as standard (100).

From the results shown above, it can be seen that Samples A, B, C, D, E, G, and H of this invention prepared using the couplers of this invention having —$NHSO_2$- group in the molecule are excellent in sensitivity, gradation, and maximum density as compared with Comparison Sample I. Furthermore, in Sample F of this invention produced using the coupler having introduced in the molecule thereof —$NHSO_2$—, the same improvements as above are obtained as compared to Comparison Sample J.

Example 2

Color photographic light-sensitive material samples K to P each having Layer 1 (the lowermost layer) to Layer 7 (the uppermost layer) described below formed, in succession, on a paper support having polyethylene layer on both surfaces thereof were prepared.

Layer 1: A blue-sensitive silver halide emulsion layer containing a silver chlorobromide emulsion (Br 80 mol %, silver coverage 350 mg/m$^2$), 1,500 mg/m$^2$ of gelatin, 500 mg/m$^2$ of a yellow coupler (*1) and 400 mg/m$^2$ of a solvent (*2).

Layer 2: A layer containing 1,100 mg/m$^2$ of gelatin, 200 mg/m$^2$ of a color mixing preventing agent (*3), and 100 mg/m$^2$ of a solvent (*4).

Layer 3: A green-sensitive emulsion layer containing a silver chlorobromide emulsion (Br 50 mol %, silver coverage 180 mg/m$^2$), 3.4×10$^{-4}$ mol/m$^2$ of a magenta coupler (*5), and a solvent (*6) in an amount of 370 mg/m$^2$ for Sample K, 560 mg/m$^2$ Sample L, 380 mg/m$^2$ Sample M, 600 mg/m$^2$ Sample N, 0.340 mg/m$^2$ Sample O and 360 mg/m$^2$ Sample P.

Layer 4: A layer containing 1,600 mg/m$^2$ of gelatin, 700 mg/m$^2$ of a ultraviolet absorbent (*7), 200 mg/m$^2$ of a color mixing preventing agent (*3), and 300 mg/m$^2$ of a solvent (*4).

Layer 5: A red-sensitive emulsion layer containing a silver chlorobromide emulsion (Br 50 mol %, silver coverage 300 mg/m$^2$, 1,200 mg/m$^2$ of gelatin, 400 mg/m$^2$ of a cyan coupler (*8), and 250 mg/m$^2$ of a solvent (*4).

Layer 6: A layer containing 1,000 mg/m$^2$ of gelatin, 360 mg/m$^2$ of a ultraviolet absorbent (*7), and 120 mg/m$^2$ of a sovlent (*4).

Layer 7 (the uppermost layer): A layer containing 1,600 mg/m$^2$ of gelatin.

Support: Paper support coated on both surfaces thereof with polyethylene.

The composition of coating solution used for the layer 3 containing emulsified dispersion or emulsion of magenta coupler was prepared according to the procedure of Example 1.

Each of the Samples K to P thus prepared was light-exposed as in Example 1 using blue, green, and red three separation filters and then subjected to color development processings. The color images obtained were exposed to a fluorescent lamp fade-o-meter (15,000 lux) for 4 weeks for testing the fastness of the magenta dye images. The results thus obtained are shown in Table 2 below.

TABLE 2

| Sample | Density after irradiation by fluorescent lamp for 4 weeks of an initial density of 1.0 |
| --- | --- |
| K | 0.73 (0.12) |
| L | 0.78 (0.12) |
| M | 0.81 (0.12) |
| N | 0.80 (0.12) |
| O | 0.31 (0.13) |
| P | 0.63 (0.13) |

In this above table:
Samples K to N: Samples of this invention.
Samples O and P: Comparison samples.
The numeral in the parentheses is a density value (stain) obtained by measuring the non-colored portion using blue filter.
The compounds used in the example are as follows.
*1: Yellow Coupler α-Pivaloyl-α-(2,4-dioxo-5,5'-dimethyloxazolidin-3-yl)-2-chloro-5-[α-(2,4-di-tert-pentylphenoxy)-butanamido]acetanilide.
*2: Solvent Dioctylbutyl phosphate.
*3: Color Mixing Preventing Agent 2,5-Dioctylhydroquinone.
*4: Solvent Dibutyl phthalate.
*5: Magenta coupler Coupler (M - 1) of this invention for Sample K, Coupler (M - 2) of this invention for Sample L, Coupler (M - 7) of this invention for Sample M, Coupler (M - 14) of this invention for Sample N, Comparison Coupler C described below for Sample O

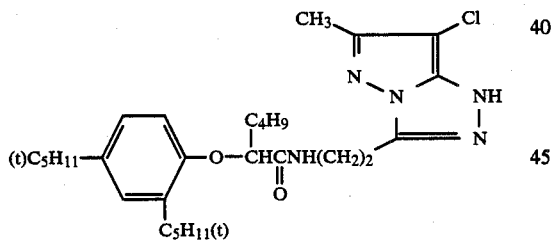

Comparison Coupler a in Examples 1 for Sample P.
*6: Solvent Tri-(2-ethylhexyl) phosphate.
*7: Ultraviolet Absorbent 2-(2-Hydroxy-3-sec-butyl-5-tert-butylphenyl)benzotriazole. *8: Cyan Coupler 2-[α-2,4-Di-tert-pentylphenoxy)butanamido]-4,6-dichloro-5-ethylphenol.

From the results shown in Table 2, it can be seen that in the comparison samples, Sample P using the coupler having a branched alkyl group shows a high light fastness of color images as compared with Sample O using the coupler having no branched alkyl group and further the samples of this invention each using the coupler in which a branched alkyl group is directly bonded to a pyrazolotriazole ring and also group -NHSO$_2$- is connected to the alkylene group bonded to the pyrazolotriazole ring show higher light fastness of color images. Also, it can be seen that in the samples of this invention, remaining couplers do not show a behavior giving bad actions to colored dyes by light.

Example 3

To 6.15 g of Coupler (M - 12) as a magenta coupler were added 12.3 g of Compound (P - 5) and 30 ml of ethyl acetate, the mixture was heated to about 60° C. to dissolve the coupler, and after adding the solution to 100 g of an aqueous solution containing 10 g of gelatin and 1 g of sodium dodecylbenzenesulfonate, the resultant mixture was dispersed by mechanical means to provide a finely emulsified dispersion. The whole amount of the emulsified dispersion was added to 100 g of a silver chlorobromide emulsion (containing 6.55 g of silver) containing 80 mol % bromine. Directly before coating, 11.7 ml of 2% 1,3-divinylsulfonylpropane was added to the mixture as a hardening agent and the mixture was coated on a paper support having polyethylene coating on both surfaces thereof so that the silver coverage became 180 mg/m$^2$ and then a gelatin layer was formed on the coated layer to provide Sample 1.

Then, Samples 2, 3, and 4 were also prepared by following the same procedure as above using Compounds (P - 24), (P - 38), and (P - 43), respectively in place of Compound (P - 5) described above.

Furthermore, as comparison samples, Samples 5 and 6 were prepared, respectively, using Comparison Compound A shown below as an example of a low-dielectric constant compound and Comparison Compound B as an example of a low dielectric constant low-viscosity compound.

Furthermore, as other comparison examples, Samples 7 and 8 were prepared by following the same procedure as above using Comparison Coupler (1) shown below and Compound (P - 5) and Comparison Compound B shown below, respectively.

Comparison Compound A:

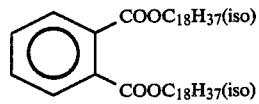

(Dielectric constant 3.61, Viscosity 117)

Comparison Compound B:

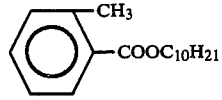

(Dielectric constant 3.61, Viscosity 7.9)

Comparison Coupler 1:

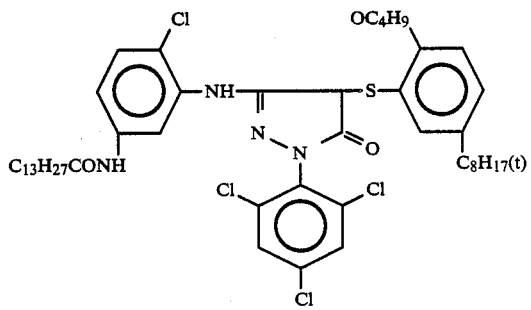

Each of the samples 1 to 8 thus prepared was wedge-exposed At 1,000 CMS and then processed by the following processing steps.

| Processing step | Temperature | Time |
|---|---|---|
| Development | 33° C. | 3 min. 30 sec. |
| Blix | 33° C. | 1 min. 30 sec. |
| Wash | 28 to 35° C. | 3 min. |

The composition of the processing liquids used in the above steps were as follows.

| Developer | |
|---|---|
| Benzyl Alcohol | 15 ml |
| Diethylenetriamine Pataacetic Acid | 5 g |
| Potassium Bromide | 0.4 g |
| Sodium Sulfite | 5 g |
| Sodium Carbonate | 30 g |
| Hydroxylamine Sulfate | 2 g |
| 4-Amino-3-methyl-N—β-(methanesulfon-amido)ethylaniline.3/2H$_2$SO$_4$·H$_2$O | 4.5 g |
| Water to make | 1 liter |
| (pH 10.1) | |
| Blix liquid | |
| Ammonium Thiosulfate (70 wt. %) | 150 ml |
| Sodium Sulfite | 5 g |
| Na[Fe(EDTA)] | 40 g |
| Ethylenediamine Tetraacetic Acid (EDTA) | 4 g |
| Water to make | 1 liter |
| (pH 6.8) | |

The photographic properties of each sample thus processed were measured and the results are shown in Table 3 below.

TABLE 3

| Sample | Coupler | High-Boiling point-Organic Compound | Photographic Property | | |
|---|---|---|---|---|---|
| | | | Fog | R.S.*1 | Density*2 |
| 1 | M - 12 | P - 5 | 0.09 | 126 | 2.45 |
| 2 | " | P - 24 | 0.08 | 131 | 2.48 |
| 3 | " | P - 38 | 0.09 | 122 | 2.42 |
| 4 | " | P - 43 | 0.08 | 124 | 2.44 |
| 5 | " | A*3 | 0.10 | 110 | 2.35 |
| 6 | " | B*4 | 0.09 | 103 | 2.30 |
| 7 | C.C. A*5 | P - 5 | 0.11 | 100 | 2.33 |
| 8 | " | A*3 | 0.12 | 93 | 2.15 |

*1Relative Sensitivity: Relative value of the value of log E giving the density of fog + 0.5 with Sample 7 [Comparison Coupler A, Compound (P - 3)] as the standard.
*2Density of Shoulder Portion showing density (D$_G$) corresponding to the exposure amount higher than log E (sensitive point) giving density of fog + 0.5 by the exposure amount of log E = 0.5
*3Comparison Compound A.
*4Compasison Compound B.
*5Comparison Coupler A.

From the results shown in the above table, it can be seen that the use of the coupler for use in this invention as a combination thereof with a high-boiling point-organic solvent having a dielectric constant of at least 4.00 and a viscosity of at least 20 c.p. gives high sensitivity and high density at a portion near the maximum density (density at shoulder portion), that is, the coupler which has hitherto been considered to be inferior in photographic properties to conventional pyrazolone couplers and reluctant to practically use is greatly improved in the photographic properties and for practical use thereof, and further the coupler gives less fog in the case of using together with the above-described high-boiling point-organic solvent.

Also, the color images obtained by the photographic processing describe above using the coupler of this invention gives less secondary absorption at a short wavelength region as compared with the case of using a conventional 5-pyrazolone coupler (Comparison Coupler (A)) because of the properties of the coupler of this invention and shows clear magenta hue owing to the low density at the long wavelength region.

Then, the samples processed as above were subjected to a fading test for 20 days at high-temperature high-humidity conditions of 60° C. and 70% RH and the results shown in Table 4 below were obtained.

TABLE 4

| Sample | Coupler | High-Boiling Point-Organic Coupler | Change of Magenta Density*1 | Stain D$_B$ |
|---|---|---|---|---|
| 1 | M - 12 | P - 5 | 0.99 | 0.10 |
| 2 | " | P - 24 | 0.99 | 0.10 |
| 3 | " | P - 38 | 0.98 | 0.10 |
| 4 | " | P - 43 | 0.99 | 0.09 |
| 5 | " | Comparison Compound A | 0.97 | 0.12 |
| 6 | " | Comparison Compound B | 0.94 | 0.12 |
| 7 | Comparison Coupler A | P - 5 | 0.93 | 0.36 |
| 8 | " | Comparison Compound B | 0.90 | 0.41 |

*1Initial density D$_G$ = 1.0

From the results shown in the above table, it can be seen that the color images obtained by using the combination of the coupler for use in this invention and the high-boiling point-organic solvent for use in this invention are excellent in wet- and heat-fastnesses as well as have less stain which is said to be formed by the decomposition of coupler.

Example 4

To 10.42 g of Coupler (M - 14) were added 20.8 g of Compound (P - 41) as a high-boiling point-organic solvent and 30 ml of ethyl acetate and then a coating composition was prepared using the mixture thus formed according to the method described in Example 1. Then, other coating composition was prepared using 6.62 g of Coupler (M - 1), 13.2 g of Compound (P - 1) as a high-boiling organic solvent, and 30 ml of ethyl acetate by the same manner as above. Furthermore, a still other coating composition was prepared using Comparison Coupler (1) and Comparison Compound A shown in Example 3 by the same manner as above.

Now, by using the three kinds of the coupler emulsions (coating compositions) prepared above which are used for layer 3, samples 11, 12, and 13 of color photographic light-sensitive materials were prepared by forming Layer 1 (the lowermost layer) to Layer 7 (the uppermost layer) as shown below on a paper support having polyethylene coating on both surfaces thereof according to the manner as in Example 3.

In addition, the coating compositions for each layer were prepared according to the manners as shown in Example 3.

Support: Paper support laminated on both surfaces thereof with polyethylene

| Layer 1: Blue-Sensitive Emulsion Layer | |
|---|---|
| Silver Chlorobromide Emulsion (silver bromide 90 mol %) | 290 mg/m$^2$ as silver |
| Yellow Coupler (*l) | 600 mg/m$^2$ |
| Fading Preventing Agent (*g) | 280 mg/m$^2$ |
| Solvent (*c) | 30 mg/m$^2$ |

-continued

| | |
|---|---|
| Solvent (*d) | 15 mg/m² |
| Gelatin | 1800 mg/m² |
| Layer 2: Color Mixing Preventing Layer | |
| Silver Bromide Emulsion | 10 mg/m² as silver |
| Color Mixing Preventing Agent | 55 mg/m² |
| Solvent (*c) | 30 mg/m² |
| Solvent (*d) | 15 mg/m² |
| Gelatin | 800 mg/m² |
| Layer 3: Green-Sensitive Emulsion Layer | |
| Silver Chlorobromide Emulsion (silver bromide 74 mol %) | 305 mg/m² as silver |
| Magenta Coupler (*i) | 670 mg/m² |
| Fading Preventing Agent (*j) | 150 mg/m² |
| Fading Preventing Agent (*k) | 10 mg/m² |
| Solvent (*l) | 200 mg/m² |
| Gelatin | 1400 mg/m² |
| Layer 4: Color Mixing Preventing Layer | |
| Color Mixing Preventing Agent (*h) | 65 mg/m² |
| Ultraviolet Absorbent (*a) | 450 mg/m² |
| Ultraviolet Absorbent (*b) | 230 mg/m² |
| Solvent (*c) | 50 mg/m² |
| Solvent (*d) | 50 mg/m² |
| Gelatin | 1700 mg/m² |
| Layer 5: Red-Sensitive Emulsion Layer | |
| Silver Chlorobromide Emulsion (silver chloride 74 mol %) | 210 mg/m² as silver |
| Cyan Coupler (*e) | 260 mg/m² |
| Cyan Coupler (*f) | 120 mg/m² |
| Fading Preventing Agent (*g) | 250 mg/m² |
| Solvent (*c) | 160 mg/m² |
| Solvent (*d) | 100 mg/m² |
| Gelatin | 1800 mg/m² |
| Layer 6: Ultraviolet Absorption Layer | |
| Ultraviolet Absorbent (*a) | 260 mg/m² |
| Ultraviolet Absorbent (*b) | 70 mg/m² |
| Solvent (*c) | 300 mg/m² |
| Solvent (*d) | 100 mg/m² |
| Gelatin | 700 mg/m² |
| Layer 7: Protective Layer | |
| Gelatin | 600 mg/m² |

The compounds used in these samples were as follows:
(*a) 2-(2-Hydroxy-3,5-di-tert-amylphenyl)benzotriazole.
(*b) 2-(2-Hydroxy-3,5-di-tert-butylphenyl)benzotriazole.
(*c) Di(2-ethylhexyl)phthalate
(*d) Dibutyl phthalate
(*e) 2-Pentafluorobenzamido-4-chloro-5[2-α-(2,4-di-tert-amylphenoxy)]-3-methyl-butylamidophenol.
(*f) 2,4-Dichloro-3-methyl-6-[α-(2,4-di-tert-amyl-phenoxy)butylamido]phenol.
(*g) 2,5-Di-tert-amylphenyl-3,5-di-tert-butyl-hydroxybenzoate.
(*h) 2,5-Di-tert-octylhydroquinone.
(*i) The coating composition of Coupler (M - 14) and Compound (P - 41), Coupler (M - 1) and Compound (P - 1), or Comparison Coupler (I) and Comparison Compound (A) prepared as described above.
(*j) 1,4-Di-tert-amyl-2,5-dioctyloxybenzene.
(*k) 2,2'-Methylenebis(4-methyl-6-tert-butylphenol).
(*l) α-Pivaloyl-α-(3-benzyl-1-hydantoinyl-2-chloro-5-[α-(2,4-di-tert-amylphenoxy)-butylamidoacet-anilide.

Also, the following sensitizing dye was used for each emulsion layer described above.

Blue-Sensitive Emulsion Layer:
Anhydro-5-methoxy-5'-methyl-3,3'-disulfopropyl-selenacyanine hydroxide ($2.5 \times 10^{-4}$ mol per mol of the silver halide).

Green-Sensitive Emulsion Layer:
Anhydro-9-ethyl-5,5'-diphenyl-3,3'-disulfoethylox-acarbocyanine hydroxide ($2 \times 10^{-4}$ mol per mol of the silver halide).

Red-Sensitive Emulsion Layer:
3,3'-Diethyl-5-methoxy-9,9'-(2,2'-dimethyl-1,3-propano)thiadicarbocyanine iodide ($2 \times 10^{-4}$ mol per mol of the silver halide).

Each of the three kinds of color photographic light-sensitive materials (Samples 11 to 13) was light-exposed using three color separation filters of blue(B), green(G), and red(R) and processed as Example 3.

The results showed that Samples 11 and 12 using the combination of Coupler (M - 14) and Compound (P - 41) and the combination of Coupler (M - 1) and Compound (P - 1), respectively had high sensitivity as compared with Comparison Sample 13 and the magenta color images formed using the samples of this invention had high density at shoulder portion of a high density region, low density at fog portions, and showed clear color tone having high saturation in hue.

Example 5

In 12.3 g of Compound (P - 23) and 25 ml of ethyl acetate was dissolved 6.17 g of Coupler (M - 12) at 60° C., the solution was added to 100 g of an aqueous solution containing 10 g of gelatin and 1.0 g of sodium dodecylbenzensulfonate, and the mixture was dispersed by a mechanical method to provide a finely emulsified dispersion. The whole amount of the emulsified dispersion was added 100 g of a silver chlorobromide emulsion (containing 6.55 g of silver) containing 90 mol % bromine and after adding thereto 10 ml of a 2% solution of 2,4-dihydroxy-6-chloro-s-triazine sodium salt as a hardening agent, the mixture was coated on a clear triacetate base at a silver coverage of 600 mg/m². Then, a gelatin layer was coated on the coated layer as a protective layer to provide Sample 21.

Then, Sample 22 was prepared by following the same manner as above using Compound (P - 7-) in place of Compound (P - 23).

Also, Samples 23 and 24 were prepared by following the same procedure as above using Coupler (M - 1) in place of Coupler (M - 12) and adding 13.3 g of Compound (P - 23) or Compound (P - 7), respectively to 6.64 g of the coupler together with 25 ml of ethyl acetate.

Furthermore, Sample 25 was prepared by following the same procedure as above using Comparison Coupler (I) shown in Example 3 above as a magenta coupler and Compound (P - 7) as a high-boiling point-organic solvent.

Still further, Sample 26 was prepared by following the same procedure as above using Coupler (M - 12) and Comparison Compound A shown in Example 1 in an amount of 12.3 g as a high-boiling organic solvent.

Each of the samples 21 to 16 thus prepared was wedge-exposed at 200 CMS and processed as follows.

| Processing step | Temperature | Time |
|---|---|---|
| 1. Color Development | 36.7° C. | 3 min. 00 sec. |
| 2. Stop | 27° C. | 40 sec. |
| 3. Wash | 27° C. | 40 sec. |
| 4. First Fix | 27° C. | 40 sec. |
| 5. Wash | 27° C. | 40 sec. |
| 6. Acceleration | 27° C. | 40 sec. |
| 7. Bleach | 27° C. | 40 sec. |
| 8. Wash | 27° C. | 40 sec. |
| 9. Second Fix | 27° C. | 40 sec. |
| 10. Wash | 27° C. | 1 min. 00 sec. |
| 11. Stabilization | 27° C. | 10 sec. |

The compositions of the processing liquids used in the above processing were as follows.

| Color Developer | |
|---|---|
| Sodium Sulfite | 4.35 g |
| 4-Amino-3-methyl-N,N—diethylaniline | 2.95 g |
| Sodium Carbonate | 17.10 g |
| Potassium Bromide | 1.72 g |
| Water to make | 1 liter |
| (pH 10.5) | |

-continued

| Stop Liquid | |
|---|---|
| Sulfuric Acid (6N) | 50 ml |
| Water to make | 1 liter |
| (pH 1.0) | |
| First and Second Fix Liquid | |
| Ammonium Thiosulfate | 60 g |
| Sodium Sulfite | 2.5 g |
| Sodium Hydrogensulfite | 10.3 g |
| Potassium Iodide | 0.5 g |
| Water to make | 1 liter |
| (pH 5.8) | |
| Acceleration Liquid | |
| Sodium Pyrosulfite | 3.3 g |
| Glacial Acetic Acid | 5.0 ml |
| PBA-1 (persulfuric acid bleach accelerator, made by Eastman Kodak) | 3.3 g |
| Ethylenediamine Tetraacetic Acid Tetrasodium Salt | 0.5 g |
| Water to make | 1 liter |
| (pH 4.0) | |
| Bleach Liquid | |
| Sodium Persulfate | 33.0 g |
| Sodium Chloride | 15.0 g |
| Sodium Dihydrogenphosphate | 7.0 g |
| Phosphoric Acid (85%) | 2.5 ml |
| Water to make | 1 liter |
| (pH 2.3) | |
| Stabilization Liquid | |
| Formalin (37%) | 15.0 ml |
| Water to make | 1 liter. |

The photographic properties were measured on each sample thus processed and the results obtained are shown in Table 5 below.

TABLE 5

| | | | Photographic Property | | |
|---|---|---|---|---|---|
| Sample | Coupler | High-Boiling Point-Organic Solvent | Fog | Relative Sensitivity* | Maximum Reached Density |
| 21 | M - 12 | P - 23 | 0.04 | 125 | 3.79 |
| 22 | " | P - 7 | 0.05 | 123 | 3.76 |
| 23 | M - 1 | P - 23 | 0.04 | 131 | 3.83 |
| 24 | " | P - 7 | 0.05 | 127 | 3.77 |
| 25 | Comparison Coupler (I) | P - 7 | 0.09 | 100 | 3.55 |
| 26 | M - 12 | Comparison Compound (A) | 0.06 | 111 | 3.66 |

*Relative Sensitivity: The relative value of the value of logE giving the density of fog + 1.0 with the sensitivity of Sample 25 containing Comparison Coupler (I) as standard (100).

The results of Table 5 above clearly show that by using the pyrazolotriazole series magenta coupler of this invention together with the high-boiling point-organic solvent of this invention having a dielectric constant of at least 4.00 and a viscosity of at least 20 c.p., the improved effects of photographic properties (high sensitivity, high coloring density, low fog, etc.,) can be obtained. Also, the color images formed using the magenta coupler of this invention show high saturation as compared with color images formed using Comparison Coupler (I).

Example 6

A color photographic light-sensitive material was prepared by coating Layer 1 to Layer 11 shown below on a paper support having polyethylene coating on both surfaces thereof. In addition, the polyethylene coating layer on the paper support at the emulsion layer-carrying side contained titanium white as a white pigment and a slight amount of ultramarine blue as a blue dye.

| Layer 1: Antihalation Layer | |
|---|---|
| Black Colloid Silver | 0.01 g/m² |
| Gelatin | 0.2 " |
| Layer 2: Low-Speed Red-Sensitive Emulsion Layer | |
| Silver Iodobromide Emulsion (silver iodide 3.5 mol %, mean grain size 0.7 μm) spectrally sensitized by red sensitizing dyes (*5 and *4) | 0.15 g/m² as silver |
| Gelatin | 1.0 g/m² |
| Cyan Coupler (*3) | 0.30 " |
| Fading Preventing Agent (*2) | 0.15 " |
| Coupler Solvent (*18 and *1) | 0.06 " |
| Layer 3: High-Speed Red-Sensitive Emulsion Layer | |
| Silver Iodobromide Emulsion (silver iodide 8.0 mol %, mean grain size 0.7 μm) spectrally sensitized red sensitizing dyes (*5 and *4) | 0.10 g/m² as silver |
| Gelatin | 0.50 g/m² |
| Cyan Coupler (*3) | 0.10 g/m² |
| Fading Preventing agent (*2) | 0.05 " |
| Coupler Solvent (*18 and *1) | 0.02 " |
| Layer 4: Interlayer | |
| Yellow Colloid Silver | 0.02 g/m² |
| Gelatin | 1.00 g/m² |
| Color mixing Preventing Agent (*14) | 0.08 " |
| Color mixing Preventing Agent Solvent (*6) | 0.16 " |
| Polymer Latex (*6) | 0.40 " |
| Layer 5: Low-Speed Green-Sensitive Emulsion Layer | |
| Silver Iodobromide Emulsion (silver iodide 2.5 mol %, mean grain size 0.4 μm) spectrally sensitized by green sensitizing dyes (*12) | 0.20 g/m² as silver |
| Gelatin | 0.70 g/m² |
| Magenta Coupler (*11) | 0.40 " |
| Fading Preventing Agent A (*10) | 0.05 " |
| Fading Preventing Agent B (*9) | 0.05 " |
| Fading Preventing Agent C (*8) | 0.02 " |
| Coupler Solvent (*7) | 0.40 " |
| Layer 6: High-Speed Green-Sensitive Emulsion Layer | |
| Silver Iodobromide Emulsion (silver iodide 3.5 mol %, mean grain size 0.9 μm) spectrally sensitized by green sensitizing dye (*12) | 0.20 g/m² as silver |
| Gelatin | 0.70 g/m² |
| Magenta Coupler (*11) | 0.40 " |
| Fading Preventing Agent A (*10) | 0.05 " |
| Fading Preventing Agent B (*9) | 0.05 g/m² |
| Fading Preventing Agent C (*8) | 0.02 " |
| Coupler Solvent (*7) | 0.40 " |
| Layer 7: Yellow Filter Layer | |
| Yellow Colloid Silver | 0.20 g/m² |
| Gelatin | 1.00 " |
| Color Mixing Preventing Agent (*14) | 0.06 " |
| Color Mixing Preventing Agent Solvent (*13) | 0.24 " |
| Layer 8: Low-Speed Blue-Sensitive Emulsion Layer | |
| Silver Iodobromide Emulsion (silver iodide 25 mol %, mean grain size 0.5 μm) spectrally sensitized with blue sensitizing dyes (*16) | 0.15 g/m² as silver |
| Gelatin | 0.50 " |
| Yellow Coupler (*15) | 0.20 " |
| Coupler Solvent (*18) | 0.05 " |
| Layer 9: High-Speed Blue-Sensitive Emulsion Layer | |
| Silver Iodobromide Emulsion (silver iodide 2.5 mol %, mean grain size 1.4 μm) spectrally sensitized with blue sensitizing dye (*16) | 0.20 g/m² as silver |
| Gelatin | 0.50 g/m² |
| Yellow Coupler (*15) | 0.20 " |
| Coupler Solvent (*18) | 0.05 " |
| Layer 10: Ultraviolet Absorption Layer | |
| Gelatin | 1.50 g/m² |
| Ultraviolet Absorbent (*19) | 1.0 " |
| Ultraviolet Absorbent Solvent (*18) | 0.30 " |
| Color Mixing Preventing Agent (*17) | 0.08 g/m² |
| Layer 11: Protective Layer | |

| | |
|---|---|
| Gelatin | 1.0 g/m² |

The compounds used for the light-sensitive material were as follows.
*1: Dioctyl Phthalate.
*2: 2-(2-Hydroxy-3-sec-butyl-5-t-butylphenyl)-benzotriazole.
*3: 2-[α-(2,4-Di-t-amylphenoxy)butylamido]-4,6-dichloro-5-ethylphenol.
*4: 5,5'-Dichloro-3,3'-di(3-sulfobutyl)-9-ethyl-thia-carbonylcaynine Na Salt.
*5: Triethylammonium-3[2-{2-[3-(3-sulfopropyl)-naphtho(1,2-d)thiazolin-2-iridenemethyl]-1-butenyl}-3-naphtho(1,2-d)thiazolino]propane Sulfonate.
*6: Polyethylacrylate
*7: Phosphoric Acid Trioctyl Ester.
*8: 2,4-Di-t-hexylhydroquinone.
*9: Di-(2-hdyroxy-3-t-butyl-5-methylphenyl)methane.
*10: 3,3,3',3'-Tetramethyl-5,6,5',6'-tetraporpoxy-1,1'-bis-spiroindane.
*11: 1-(2,4,6-Trichlorophenyl)-3-(2-chloro-5-tetra-decanamido)anilino-2-pyrazolino-5-one.
*12: 5,5'-Diphenyl-9-ethyl-3,3'-disulfopropyloxa-carbocyanine Na Salt.
*13: Phosphoric Acid o-Cresyl Ester.
*14: 2,4-Di-t-octylhydroquinone.
*15: α-Pivaloyl-α-[(2,4-dioxo-1-benzyl-5-ethoxy-hydantoin-3-yl)-2-chloro-5-[(α-2,4-dioxo-t-amylphenoxy)butanamino]acetanilide.
*16: Triethylammonium 3-[2-(3-benzylrhodanin-5-iridene)-3-benzoxazolinyl]propanesulfonate.
*17: 2,4-Di-sec-octylhydroquinone.
*18: Comparison Compound B shown in Example 3.
*19: 5-Chloro-2-(2-hydroxy-3-t-butyl-5-t-octyl)-phenylbenztriazole.

Each layer further contained 1,4-bis(vinylsulfonylacetamide)ethane as a gelatin hardening agent and a surface active agent.

Thus, Sample 31 was prepared as a comparison sample in this example.

Then, Sample 32 was prepared by following the same procedure as Sample 31 except that Magenta Coupler (M - 10) of this invention was used for Layer 5 (low-speed green-sensitive layer) and Layer 6 (high-speed green-sensitive layer) as follows.

| Layer 5: Low-Speed Green-Sensitive Emulsion Layer | |
|---|---|
| Silver Iodobromide Emulsion (silver iodide 2.5 mol %, mean grain size 0.4 μm) spectrally sensitized with green sensitizing dye (*12) | 0.10 g/m² as silver |
| Gelatin | 0.70 g/m² |
| Magenta Coupler (M - 10) | 0.59 " |
| Fading Preventing Agent A (*10) | 0.07 " |
| Fading Preventing Agent B (*9) | 0.02 " |
| Coupler Solvent (*18) | 0.59 g/m² |
| Layer 6: High-Speed Green-Sensitive Emulsion Layer | |
| Silver Iodobromide Emulsion (silver iodide 3.5 mol %, mean grain size 0.9 μm) spectrally sensitized with green sensitizing dye (*12) | 0.10 g/m² as silver |
| Gelatin | 0.70 g/m² |
| Magenta Coupler (M - 10) | 0.59 " |
| Fading Preventing Agent (*10) | 0.07 " |
| Fading Preventing Agent (*9) | 0.02 " |
| Coupler Solvent (*18) | 0.59 " |

Furthermore, Sample 33 was prepared by following the same procedure as the case of preparing Sample 31 except that Magenta Coupler (M - 10) of this invention and High-boiling point-organic solvent (P - 7) of this invention were used for Layer 5 (low-speed green-sensitive layer) and Layer 6 (high-speed green-sensitive layer) as follows.

| Layer 5: Low-Speed Green-Sensitive Emulsion Layer | |
|---|---|
| Silver Iodobromide Emulsion (silver iodide 2.5 mol %, mean grain size 0.4 μm) spectrally sensitized with green sensitizing dye (*12) | 0.10 g/m² as silver |
| Gelatin | 0.70 g/m² |
| Magenta Coupler (M - 10) | 0.59 " |
| Fading Preventing Agent (*10) | 0.07 " |
| Fading Preventing Agent (*9) | 0.02 " |
| Coupler Solvent (P - 7) | 0.59 " |
| Layer 6: High-Speed Green-Sensitive Emulsion Layer | |
| Silver Iodobromide Emulsion (silver iodide 3.5 mol %, mean grain size 0.9 μm) spectrally sensitized with green sensitizing dye (*12) | 0.10 g/m² as silver |
| Gelatin | 0.70 g/m² |
| Magenta Coupler (M - 10) | 0.59 " |
| Fading Preventing Agent A (*10) | 0.07 " |
| Fading Preventing Agent B (*9) | 0.02 " |
| Coupler Solvent (P - 7) | 0.59 " |

Each of Samples 31 to 33 thus prepared was wedge-exposed by an ordinary manner and processed by the following photographic processing steps. Then, the photographic properties were measured on each sample thus processed. In this case, the density measurement was performed using Fuji FSD-103 made by Fuji Film Co. Ltd.

| Processing Step | | |
|---|---|---|
| First Development (black and white development) | 38° C. | 1 min. 15 sec. |
| Wash | 38° C. | 1 min. 30 sec. |
| Reversal Exposure above 100 lux | | above 1 min. |
| Color Development | 38° C. | 2 min. 15 sec. |
| Wash | 38° C. | 45 sec. |
| Blix | 38° C. | 2 min. 00 sec. |
| Wash | 38° C. | 2 min. 15 sec. |

The compositions of the processing liquids used in the above processing steps were as follows.

| First Developer | |
|---|---|
| Nitrilo-N,N,N—trimethylenephosphonic Acid Pentasodium Salt | 0.6 g |
| Diethylenetriaminepentaacetic Acid Pentasodium Salt | 4.0 g |
| Potassium Sulfite | 30.0 g |
| Potassium Thiocyanate | 1.2 g |
| Potassium Carbonate | 35.0 g |
| Hydroquinone Monosulfonate Potassium Salt | 25.0 g |
| Diethylene Glycol | 15.0 ml |
| 1-Phenyl-4-hydroxymethyl-4-methyl-3-pyrazolidone | 2.0 g |
| Potassium Bromide | 0.5 g |
| Potassium Iodide | 5.0 mg |
| Water to make | 1 liter |
| (pH 9.70) | |
| Color Developer | |
| Benzyl Alcohol | 15.0 ml |
| Diethylene Glycol | 12.0 ml |
| 3,6-Dithia-1,8-octanediol | 0.2 g |
| Nitrilo-N,N,N—trimethylenephosphonic Acid Pentasodium Salt | 0.5 g |
| DiethylenetriaminePentaacetic Acid Pentasodium Salt | 2.0 g |
| Sodium Sulfite | 2.0 g |
| Potassium Carbonate | 25.0 g |
| Hydroxylamine Sulfate | 3.0 g |
| N—Ethyl-N—(β-methanesulfonamidoethyl)-3-methyl-4-aminoaniline Sulfate | 5.0 g |
| Potassium Bromide | 0.5 g |
| Potassium Iodide | 1.0 mg |
| Water to make | 1 liter |
| (pH 10.40) | |
| Blix Liquid | |
| 2-Mercapto-1,3,4-triazole | 1.0 g |
| Ethylenediaminetetraacetic Acid Disodium Dihydrate | 5.0 g |
| Ethylenediaminetetraacetic Acid Fe(III) Ammonium Monohydrate | 80.0 g |
| Sodium Sulfite | 15.0 g |
| Ammonium Thiosulfate (700 g/liter | |

-continued

| | |
|---|---|
| solution) | 160.0 ml |
| Glacial Acetic Acid | 5.0 ml |
| Water to make | 1 liter |
| (pH 6.50) | |

The results obtained are shown in Table 6 below.

TABLE 6

| Sample | Coated Amount of Silver (g/m$^2$) | Maximum Coloring Density | Color Image Stabilization | |
|---|---|---|---|---|
| | | | Color Image Residue (%) | Stain** |
| 31 | 1.18 | 2.45 | 89 | 0.30 |
| 32 | 1.17 | 2.55 | 93 | 0.13 |
| 33 | 1.17 | 2.69 | 97 | 0.08 |

*: Residual ratio of magenta density after the xenon lamp (100,000 lux) irradiation of 12 days.
**: [Yellow stain density after placing under 60° C. and 70% RH for 6 weeks] − [Yellow stain density of fresh sample]
Samples 31 and 32: Comparison samples.
Sample 33: Sample of this invention.

From the results shown in the above table, it can be seen that Sample 33 using the coupler of this invention together with the high-boiling point-organic solvent of this invention shows excellent coloring density, is excellent in color image stability, and gives less stain which deteriorates the image quality. Furthermore, the color images obtained had clear magenta color having high saturation.

EXAMPLE 7

Sample 41 was prepared by coating Layer 1 to Layer 12 shown below, in succession, on a triacetate film base.

Layer 1: Antihalation Layer

After mixing 15 g of 5-chloro-2-(2-hydroxy-3,5-di-t-butylphenyl)-2H-benzotriazole, 30 g of 2-(2-hydroxy-5-t-butylphenyl)-2H-benzotriazole, 35 g of 2-(2-hydroxy-3-sec-butyl-5-t-butylphenyl)-2H-benzotriazole, and 100 g of dodecyl-5-(N,N-diethylamino)-2-benzenesulfonyl-2,4-pentdienoate as ultraviolet absorbents with 200 ml of tricresyl phosphate, 200 ml of ethyl acetate, 20 g of sodium dodecylbenzenesulfonate, and an aqueous 10% gelatin solution with stirring at high speed, the emulsion (hereinafter, is referred to as Emulsion (a)) thus obtained was mixed with 10 g of an aqueous 10% gelatin solution, a gelatin emulsion of black colloid silver, water and coating aid and the resultant mixture was coated on the support at a dry thickness of 2 μm.

Layer 2: Gelatin Interlayer

In a mixture of 100 ml of dibutyl phthalate and 100 ml of ethyl acetate was dissolved 2,5-di-t-octylhydroquinone, the solution was mixed with 1 kg of an aqueous 10% gelatin solution with stirring at high speed, 2 kg of the emulsion (hereinafter, is referred to as Emulsion (b)) thus obtained was mixed with 1.5 kg of an aqueous 10% gelatin solution, and the mixture was coated on the antihalation layer at a dry thickness of 1 μm. The above hydroquinone compound was used in an amount of 40 mg/m$^2$.

Layer 3: Low-Speed Red-Sensitive Emulsion Layer

In a mixture of 100 ml of tricresyl phosphate and 100 ml of ethyl acetate was dissolved 100 g of a cyan coupler, 2-(heptafluorobutylamido)-5-{2′-(2″,4″-di-t-aminophenoxy)butylamido}-phenol, the solution was mixed with 1 kg of an aqueous 10% gelatin solution with stirring at high speed, 500 g of the emulsion (hereinafter, is referred to as Emulsion (c)) thus obtained was mixed with 1 kg of a red-sensitive silver iodobromide emulsion (containing 70 g of silver and 60 g of gelatin and having an iodine content of 4 mol %), and the resultant mixture was coated on the interlayer at a dry thickness of 1 μm (silver coverage of 0.5 g/m$^2$).

Layer 4: High-Speed Red-Sensitive Emulsion Layer

Emulsion (c) described above was mixed with 1 kg of a red-sensitive silver iodobromide emulsion (containing 70 g of silver and 60 g of gelatin and having an iodine content of 2.5 mol %) and the mixture was coated on the emulsion layer at a dry thickness of 2.5 μm (silver coverage of 0.8 g/m$^2$).

Layer 5: Interlayer

A mixture of 1 kg of Emulsion (b) described above and kg of an aqueous 10% gelatin solution was coated on the emulsion layer at a dry thickness of 1 μm.

Layer 6: Low-Speed Green-Sensitive Emulsion Layer

By following the same procedure as the case of preparing the emulsion for Layer 3 described above except that a magenta coupler, 1-(2,4,6-trichlorophenyl)-3-{3-(2,4-di-t-amylphenoxyacetamido)benzamido}-5-pyrazolone in place of the cyan coupler and also Comparison Compound B shown in Example 1 was used, an emulsion (hereinafter, is referred to as Emulsion (d)), 300 g of the emulsion thus obtained was mixed with 1 kg of a green-sensitive silver iodobromide emulsion (containing 70 g of silver and 60 g of gelatin and having an iodine content of 3 mol %), and the mixture was coated on the interlayer at a dry thickness of 2.0 μm (silver coverage of 0.7 g/m$^2$).

Layer 7: High-Speed Green-Sensitive Emulsion Layer

A mixture of 1,000 g of Emulsion (d) described above and 1 kg of a green-sensitive silver iodobromide emulsion (containing 70 g of silver and 60 g of gelatin and having an iodine content of 2.5 mol %) was coated on the emulsion layer at a dry thickness of 2.0 μm (silver coverage of 0.7 g/m$^2$).

Layer 8: Gelatin Interlayer

A mixture of 1 kg of Emulsion (b) described above and 1 kg of an aqueous 10% gelatin solution was coated on the above-described emulsion layer at a dry thickness of 0.5 μm.

Layer 9: Yellow Filter Layer

An emulsion containing yellow colloid silver was coated on the interlayer at a dry thickness of 1 μm.

Layer 10: Low-Speed Blue-Sensitive Emulsion Layer

By following the same procedure as the case of preparing the emulsion for Layer 3 except that a yellow coupler, α-(pivaloyl)-α-(1-benzyl-5-ethoxy-3-hydantoinyl)-2-chloro-5-dodecyloxycarbonylacetanilide was used in place of the cyan coupler, an emulsion (hereinafter, is referred to as Emulsion (e)) was prepared, 1,000 g of the emulsion thus prepared was mixed with 1 kg of a blue-sensitive silver iodobromide emulsion (containing 70 g of silver and 60 g of gelatin and having an iodine content of 2.5 mol %), and the resultant mixture was coated on the yellow filter layer at a dry thickness of 1.5 μm (silver coverage of 0.6 g/m$^2$).

11 High-Speed Blue-Sensitive Emulsion Layer

A mixture of 1,000 g of Emulsion (e) described above and 1 kg of a blue-sensitive silver iodobromide emulsion (containing 70 g of silver and 60 g of gelatin and having an iodine content of 2.5 mol %) was coated on the emulsion layer at a dry thickness of 3 μm (silver coverage of 1.1 g/m²).

Layer 12: Second Protective Layer

A mixture of Emulsion (a) described above, an aqueous 10% solution, water, and a coating aid was coated on the above-described emulsion layer at a dry thickness of 2 μm.

Layer 13: First Protective Layer

An aqueous 10% solution containing a surface-fogged fine grain silver halide emulsion (grain size of 0.06 μm, silver iodobromide emulsion containing 1 mol % silver iodide) was coated on the 2nd protective layer at a silver coverage of 0.1 g/m² and a dry thickness of 0.8 μm.

Also, each layer further contained 1,4-bis(vinylsulfonylacetamido)ethane as a gelatin hardening agent and a surface active agent.

Then, Sample 42 was prepared by following the same procedure as the case of preparing Sample 41 except that Magenta coupler (M - 1) for use in this invention was used for Layer 6 (low-speed green-sensitive layer) and Layer 7 (high-speed green-sensitive layer) as follows.

Layer 6: Low-Speed Green-Sensitive Emulsion Layer

By following the same procedure as the case of preparing the emulsion for Layer 3 except that Magenta Coupler (M - 1) in this invention was used, an emulsion (hereinafter, is referred to as Emulsion (f)), used in an equimolar amount to Emulsion (d) was mixed with 500 g of a green-sensitive silver iodobromide emulsion (containing 35 g of silver and 30 g of gelatin and having an iodine content of 3 mol %) and the mixture was coated at a dry thickness of 20 μm (silver coverage of 0.35 g/m²).

Layer 7: High-Speed Green-Sensitive Emulsion Layer

A mixture of Emulsion (f) used in an equimolar amount to Emulsion (d) and 500 g of a green-sensitive silver iodobromide emulsion (containing 35 g of silver and 30 g of gelatin and having an iodine content of 2.5 mol %) was coated at a dry thickness of 20 μm (silver coverage of 0.35 g/m²).

Moreover, by following the same procedure as the case of preparing the emulsion for Layer 3 except that Magenta Coupler (M - 1) in this invention and High-Boiling Point-Organic Solvent (P - 25) in this invention were used, an emulsion (hereinafter, is referred to as Emulsion (g)) and Sample 43 was prepared by following the same procedure as above using Emulsion (g) in place of Emulsion (f).

Each of Samples 41 to 43 thus prepared was wedge-exposed and processed by the following processing steps. Then, the photographic properties of each sample processed were measured and the results obtained are shown in Table 7 below. In addition, the density measurement was performed using Fuji FSD-103.

| Processing Step | | |
|---|---|---|
| First Development | 38° C. | 6 min. |
| Wash | " | 2 min. |
| Reversal | " | 2 min. |
| Color Development | " | 6 min. |
| Control | " | 2 min. |
| Bleach | " | 6 min. |
| Fix | " | 4 min. |
| Wash | " | 4 min. |
| Stabilization | room-temp. | 1 min. |
| Drying | | |

The compositions of the processing liquids used in the above processing steps are as follows.

| First Developer | |
|---|---|
| Water | 700 ml |
| Nitrilo-N,N,N—trimethylenephosphonic Acid.Pentasodium Salt | 2 g |
| Sodium Sulfite | 20 g |
| Hydroquinone Monosulfonate | 30 g |
| Sodium Carbonate (Monohydrate) | 30 g |
| 1-Phenyl-4-methyl-4-hydroxymethyl-3-pyrazolidone | 2 g |
| Potassium Bromide | 2.5 g |
| Potassium Thiocyanate | 1.2 g |
| Potassium iodide (0.1% soln.) | 2 ml |
| Water to make | 1 liter |
| Reversal Liquid | |
| Water | 700 ml |
| Nitrilo-N,N,N—trimethylenephosphoric Acid Pentasodium Salt | 3 g |
| Stannous Chloride (Dihydrate) | 1 g |
| p-Aminophenol | 0.1 g |
| Sodium Hydroxide | 8 g |
| Glacial Acetic Acid | 15 ml |
| Water to make | 1 liter. |
| Color Developer | |
| Water | 700 ml |
| Nitrilo-N,N,N—trimethylenephosphonic Acid Pentasodium Salt | 3 g |
| Sodium Sulfite | 7 g |
| Sodium Tertiary Phosphate (12-Hydrate) | 36 g |
| Potassium Bromide | 1 g |
| Potassium Iodide (0.1% soln.) | 90 ml |
| Sodium Hydroxide | 3 g |
| Citrazinic Acid | 1.5 g |
| N—Ethyl-N—(β-methanesulfonamidethyl)-3-methyl-4-aminoaniline Sulfate | 11 g |
| 3,6-Dithiaoctane-1,8-diol | 1 g |
| Water to make | 1 liter |
| Control Liquid | |
| Water | 700 ml |
| Sodium sulfite | 12 g |
| Ethylenediaminetetraacetic Acid Sodium (Dihydrate) | 8 g |
| Thioglycerol | 0.4 ml |
| Glacial Acetic Acid | 3 ml |
| Water to make | 1 liter. |
| Bleach Liquid | |
| Water | 800 ml |
| Ethylenediaminetetraacetic Acid Sodium (Dihydrate) | 2 g |
| Ethylenediaminetetraacetic Acid Iron(III) Ammonium (Dihydrate) | 120 g |
| Potassium Bromide | 100 g |
| Water to make | 1 liter |
| Fix Liquid | |
| Water | 800 ml |
| Ammonium Thiosulfate (70 wt. %) | 115 g |
| Sodium Sulfite | 5.0 g |
| Sodium Hydrogensulfite | 5.0 g |
| Water to make | 1 liter |
| Stabilization Liquid | |
| Water | 800 ml |
| Formalin (37 wt. %) | 5.0 ml |
| Fuji Dry Well (Surface active agent, | |

| | -continued | |
|---|---|---|
| trade name, made by Fuji Photo Film Co., Ltd) | | 5.0 ml |
| Water to make | | 1 liter |

TABLE 7

| Sample No. | Amount of Silver (g/m²) | Maximum Coloring Density | Color Image Stability | |
|---|---|---|---|---|
| | | | Color Image Residue* (%) | Stain** |
| 41 | 4.9 | 3.01 | 88 | 0.18 |
| 42 | 4.5 | 3.20 | 93 | 0.10 |
| 43 | 4.5 | 3.38 | 98 | 0.05 |

*Residual ratio of the magenta density after xenon lamp (100,000 lux) irradiation of 4 days.
**[Yellow stain density after 4 weeks at 60° C., 70% RH]—[Yellow stain density of fresh sample]
Samples 41 and 42: Comparison samples.
Sample 43: Sample of this invention.

From the results shown in Table 7 above, it can be seen that Samples 43 using the magenta coupler in this invention and the high-boiling point-organic solvent in this invention shows good coloring density. This suggests that there is a possibility of reducing the amount of silver for obtaining a definite maximum coloring density. Also, the color photographic light-sensitive material of this invention containing the above-described magenta coupler and the high-boiling organic solvent is excellent in color image stability, gives less stain, and hence is very advantageous as printing materials. Furthermore, the magenta color images obtained using the samples of this invention showed clear hue having high saturation.

EXAMPLE 8

In 13.2 g of Compound (P -45) and 20 ml of ethyl acetate was dissolved 6.62 g of Coupler (M - 1) as a magenta coupler at 60° C. and the solution was mixed with 100 ml of an aqueous solution containing 10 g of gelatin and 1.0 g of sodium dodecylbenzenesulfonate by a mechanical method to provide a finely emulsified dispersion. The whole amount of the emulsified dispersion was added to 100 g of a silver chlorobromide emulsion (containing 6.55 g of silver) containing 80 mol % bromine and after adding thereto 10 ml of a 2% aqueous solution of 2,4-dihydroxy-6-chloro-s-triazine sodium salt as a hardening agent, the mixture was coated on a paper support having polyethylene coating at both surfaces thereof at a silver coverage of 180mg/m². Then, a gelatin layer was coated on the layer to provide Sample 1.

Then, Samples 2, 3, 4, 5, 6, and 7 were also prepared by following the same procedure as above using Compounds (P - 48), (P - 52), (P - 64), (P - 69, n=1), (P - 76), and (P - 78), respectively, in place of Compound (P - 45).

Furthermore, Sample 8 was prepared by following the same procedure as above using di-iso-octadecyl phthalate as a comparison high-boiling organic solvent in place of Compound (P - 45).

Still further, Sample 9 was prepared by following the same procedure as above using a comparison coupler shown below as a magenta coupler in place of Coupler (M - 1) using illustrative compound (p - 45) as a solvent.

Comparison Coupler

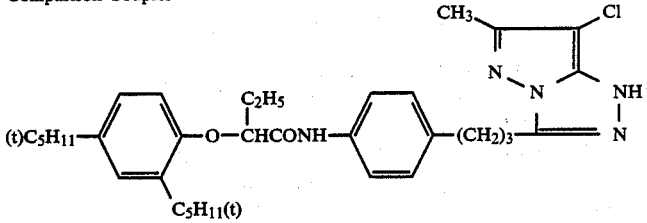

Each of Samples 1 to 9 was wedge-exposed at 1,000 CMS and then processed by the processing steps and the processing liquids described in Example 3. The photographic properties of each sample thus processed were measured and the results obtained are shown in Table 8 below.

TABLE 8

| Sample No. | Coupler | High-Boiling Point-Organic Solvent | Photographic Property | | |
|---|---|---|---|---|---|
| | | | Fog | Relative Sens.*1 | Density of Shoulder*2 |
| 1 | M-1 | P-45 | 0.09 | 134 | 2.52 |
| 2 | " | P-48 | 0.09 | 133 | 2.55 |
| 3 | " | P-52 | 0.09 | 133 | 2.53 |
| 4 | " | P-64 | 0.10 | 137 | 2.58 |
| 5 | " | P-69 | 0.09 | 131 | 2.47 |
| 6 | " | P-76 | 0.08 | 116 | 2.43 |
| 7 | " | P-78 | 0.08 | 113 | 2.41 |
| 8 | " | (a)*3 | 0.11 | 105 | 2.26 |
| 9 | Comparison Coupler (A) | P-45 | 0.10 | 100 | 2.27 |

*1Relative Sensitivity: Relative value of the value of logE giving the density of fog + 0.5 with Sample 9 using Comparison Coupler (A) as standard (100).
*2Showing density (D_G) corresponding to the exposure amount higher than log E (sensitive point) giving density of fog + 0.5 by the exposure amount of log E = 0.5.
*3Di-iso-octadecyl phthalate.

From the results shown in the above table, it can be seen that the use of the magenta coupler of this invention, which is inferior in photographic properties in conventional technique and is reluctant to practically use, together with the high-boiling point-organic solvent as defined in this invention gives very improved photographic properties such as high sensitivity and high density at shoulder portion, i.e., the portion near the maximum density. Also, it can be seen that the coupler of this invention gives excellent performance such as less formation of fog, etc., in the case of a combinated use with the high-boiling point-organic solvent in this invention.

Also, it can be seen that the color images obtained by the above-described photographic processing show clear magenta hue with a lowered absorption density at long wavelength side by the properties of the magenta coupler of this invention and the use of the high-boiling point-organic solvent of this invention.

Then, these samples thus processed were subjected to a fading test for 20 days using a fluorescent lamp fade meter (15,000 lux) and the results obtained are shown in Table 9 below.

TABLE 9

| Sample No. | Coupler | High-Boiling Point-Organic Solvent | Change of Magenta Density[*1] | Stain $D_B$[*2] |
|---|---|---|---|---|
| 1 | M-1 | P-45 | 0.95 | 0.08 |
| 2 | " | P-48 | 0.95 | 0.08 |
| 3 | " | P-52 | 0.96 | 0.08 |
| 4 | " | P-64 | 0.94 | 0.09 |
| 5 | " | P-69 | 0.96 | 0.08 |
| 6 | " | P-76 | 0.98 | 0.07 |
| 7 | " | P-78 | 0.97 | 0.07 |
| 8 | " | (a)[*3] | 0.86 | 0.11 |
| 9 | Comparison Coupler (A) | P-45 | 0.93 | 0.11 |

[*1]Initial density $D_G = 1.0$
[*2]Density passing through blue filter after performing the fading test for 20 days.
[*3]Di-iso-octadecyl phthalate.

EXAMPLE 9

By following the same procedure as described in Example 1 using 6.62 g of Coupler (M - 1), 13.2 g of Compound (p - 46) as a high boiling point-organic solvent, and 25 ml of ethyl acetate, a coating composition was prepared. Also, by following the same procedure as Example 8 using 9.56 g of Coupler (M - 2), 19.1 g of Compound (P - 72), and 30 ml of ethyl acetate, a coating composition was prepared. Still further, by following the same manner as Example 8 using 6.45 g of Comparison Coupler (A) shown in Example 1 and 12.9 g of di-iso-octadecyl phthalate as a high-boiling organic solvent, a coating composition was prepared.

Then, by forming Layer 1 (the lowermost layer) to Layer 7 (the uppermost layer) as in Example 4 on a paper support having polyethylene coating on both surfaces thereof using each of the coating compositions prepared above Samples 11, 12 and 13 of color photographic light-sensitive materials were prepared.

In this case, the additives and the amounts thereof for each layer were same as those in Example 4 except that the combination of [(M - 1) and (P - 46)], [(M - 2) and (P - 72)], or [(Comparison Coupler A) and [di-iso-octadecyl phthalate)] was used for Layer 3 as [magenta coupler and solvent] (*i).

The coating composition for each emulsion layer was prepared according to the method described in Example 8.

Each of the three kinds of color photographic material samples (11 to 13) was exposed using separation filters of blue, green, and red and processed as in Example 8.

The results of the measurement of the photographic properties of these samples thus processed show that Samples 11 and 12 using the combinations of (P - 46) and (M - 1) and (P - 72) and (M - 2) have high sensitivity as compared with Comparison Sample 13 and give color images having high density at the shoulder portion in the high density region, having high gradation, giving low density at fog portions, and having clear hue of high saturation.

EXAMPLE 10

In 15.2 . of Compound (P - 48) and 20 ml of ethyl acetate was dissolved 9.71 g of Coupler (M - 2) as a magenta coupler at 60° C. and the solution was mixed with 100 ml of an aqueous solution containing 10 g of gelatin and 1.0 g of sodium dodecylbenzenesulfonate by a mechanical method to provide a finely emulsified dispersion. The whole amount of the emulsified dispersion was added to 100 g of a silver chlorobromide emulsion (containing 6.55 g of silver) containing 90 mol % bromine and after adding thereto an aqueous solution of 2% 2,4-dihydroxy-6-chloro-s-triazine sodium salt, the mixture was coated on a triacetate base at a silver coverage of 600 mg/m². Then, a gelatin layer was formed on the layer as a protective layer to provide Sample 21.

Then, by following the same manner as above using Compound (P - 75) in place of Compound (P - 48). Also, by following the same procedure as above except that Coupler (M - 9) was used in place of Coupler (M - 2) and 9.71 g of the coupler was dissolved in 19.4 g of Compound (P - 48) or (P - 75) and 20 ml of ethyl acetate, Samples 23 and 24 were prepared.

Furthermore, by following the same procedure as above using Comparison Coupler (A) described in Example 3 as the magenta coupler and Compound (P - 48) as the high-boiling point-organic solvent, Sample 25 was prepared.

Each of Samples 21 to 25 thus prepared was wedge exposed at 200 CMS and processed by the same process as described in Example 5. The photographic properties of the samples thus processed were measured and the results obtained are shown in Table 10.

TABLE 10

| Sample No. | Coupler | High-Boiling Point-Organic Solvent | Photographic Property | | | |
|---|---|---|---|---|---|---|
| | | | Fog | Relative Sens.[*1] | Gradation[*2] | Maximum Reached Density |
| 21 | M-2 | P-48 | 0.04 | 124 | 2.94 | 3.70 |
| 22 | " | P-75 | 0.05 | 130 | 3.01 | 3.73 |
| 23 | M-9 | P-48 | 0.04 | 125 | 2.95 | 3.71 |
| 24 | " | P-75 | 0.05 | 131 | 3.03 | 3.76 |
| 25 | Comparison Coupler (A) | P-48 | 0.05 | 100 | 2.73 | 3.47 |

[*1]Relative Sensitivity: The relative value of the value of logE giving the density of fog + 1.0 with Sample 25 (Comparison Coupler A) as the standard.
[*2]The inclination of the density range of 0.5 to 1.5 in a characteristic curve.

From the results shown in the above table, the improvement effect of the photographic properties by using the pyrazolotriazole magenta coupler of this invention and the high-boiling point-organic solvent defined in this invention is clearly shown.

EXAMPLE 11

A color photographic light-sensitive material was prepared by forming Layer 1 to Layer 11 shown below on a paper support having polyethylene coating on both surfaces thereof. The polyethylene coating layer on the support at the emulsion layer-carrying side contained titanium white as a white pigment and a slight amount of ultramarine blue as a bluish dye.

Layer 1: Antihalation Layer

-continued

| | |
|---|---|
| Black Colloid Silver | 0.10 g/m² |
| Gelatin | 2.0 g/m² |
| Layer 2: Low-Speed Red-Sensitive Emulsion Layer | |
| Silver Iodobromide Emulsion (silver iodide 3.5 mol %, mean grain size 0.7 μm) spectrally sensitized by red sensitizing dyes (*5 and *4) | 0.15 g/m² as silver |
| Gelatin | 1.0 g/m² |
| Cyan Coupler (*3) | 0.30 g/m² |
| Fading Preventing Agent (*2) | 0.15 g/m² |
| Coupler Solvents (*18 and *1) | 0.06 g/m² |
| Layer 3: High-Speed Red-Sensitive Emulsion Layer | |
| Silver Iodobromide Emulsion (silver iodide 8.0 mol %, mean grain size 0.7 μm) spectrally sensitized by red sensitizing dyes (*5 and *4) | 0.10 g/m² as silver |
| Gelatin | 0.50 g/m² |
| Cyan Coupler (*3) | 0.10 g/m² |
| Fading Preventing Agent (*2) | 0.05 g/m² |
| Coupler Solvents (*18 and *1) | 0.02 g/m² |
| Layer 4: Interlayer | |
| Yellow Colloid silver | 0.02 g/m² |
| Gelatin | 1.00 g/m² |
| Fading Preventing Agent (*14) | 0.08 g/m² |
| Fading Preventing Agent Solvent (*13) | 0.16 g/m² |
| Polymer Latex (*6) | 0.10 g/m² |
| Layer 5: Low-Speed Green-Sensitive Emulsion Layer | |
| Silver iodobromide emulsion (silver iodide 2.5 mol %, mean grain size 0.4 μm) spectrally sensitized by green sensitizing dye (*12) | 0.20 g/m² as silver |
| Gelatin | 0.70 g/m² |
| Magenta coupler (*11) | 0.40 g/m² |
| Fading Preventing Agent A (*10) | 0.05 g/m² |
| Fading Preventing Agent B (*9) | 0.05 g/m² |
| Fading Preventing Agent C (*8) | 0.02 g/m² |
| Coupler Solvent (*7) | 0.40 g/m² |
| Layer 6: High-Speed Green-Sensitive Emulsion Layer | |
| Silver Iodobromide Emulsion (silver iodide 3.5 mol %, mean grain size 0.9 μm) spectrally sensitized by green sensitizing dye (*12) | 0.20 g/m² as silver |
| Gelatin | 0.70 g/m² |
| Magenta Coupler (*11) | 0.40 g/m² |
| Fading Preventing Agent A (*10) | 0.05 g/m² |
| Fading Preventing Agent B (*9) | 0.05 g/m² |
| Fading Preventing Agent C (*8) | 0.02 g/m² |
| Coupler Solvent (*7) | 0.40 g/m² |
| Layer 7: Yellow Filter Layer | |
| Yellow Colloid Silver | 0.20 g/m² |
| Gelatin | 1.00 g/m² |
| Fading Preventing Agent (*14) | 0.06 g/m² |
| Fading Preventing Agent Solvent (*13) | 0.24 g/m² |
| Layer 8: Low-Speed Blue-Sensitive Emulsion Layer | |
| Silver Iodobromide Emulsion (silver iodide 2.5 mol %, mean grain size 0.5 μm) spectrally sensitized by blue sensitizing dye (*16) | 0.15 g/m² as silver |
| Gelatin | 0.50 g/m² |
| Yellow coupler (*15) | 0.20 g/m² |
| Coupler Solvent (*18) | 0.05 g/m² |
| Layer 9: High-Speed Blue-Sensitive Emulsion Layer | |
| Silver Iodobromide Emulsion (silver iodide 2.5 mol %, mean grain size 1.4 μm) spectrally sensitized by blue sensitizing dye (*16) | 0.20 g/m² as silver |
| Gelatin | 0.50 g/m² |
| Yellow Coupler (*15) | 0.20 g/m² |
| Coupler Solvent (*18) | 0.05 g/m² |
| Layer 10: Ultraviolet Absorption Layer | |
| Gelatin | 1.50 g/m² |
| Ultraviolet Absorbent (*19) | 1.0 g/m² |
| Ultraviolet Absorbent solvent (*18) | 0.30 g/m² |
| Color Mixing Preventing Agent (*17) | 0.08 g/m² |
| Layer 11: Protective Layer | |
| Gelatin | 1.0 g.m² |

The compounds used in this case were as follows.
(*1) Dioctyl phthalate.
(*2) 2-(2-Hydroxy-3-sec-butyl-5-t-butylphenyl)-benzotriazole.
(*3) 2-[α-2,4-di-t-amylphenoxy)butylamido]-4,6-dichloro-5-ethylphenol.
(*4) 5,5'-Dichloro-3,3'-di(3-sulfobutyl)-9-ethyl-thio-carbonylcyanine Sodium Salt.
(*5) Triethylammonium 3-[2-{2-[3-(3-sulfopropyl)-naphtho(1,2-d)thiazolin-2-iridenemethyl]-1-butenyl}-3-naphtho(1,2-d)thiazolino]propane-sulfonate.
(*6) Polyethyl Acrylate,
(*7) Di-iso-octadecyl phthalate.
(*8) 2,4-Di-t-hexylhydroquinone.
(*9) Di-(2-hydroxy-3-t-butyl-5-methylphenyl)methane.
(*10) 3,3,3',3'-Tetramethyl-5,6,5',6'-tetrapropoxy-1,1'-bisspiroindane.
(*11) Comparison Coupler (A) shown in Example 8.
(*12) 5,5'-Diphenyl-9-ethyl-3,3'-disulfopropyl-oxacarbocyanine Sodium Salt.
(*13) Phosphoric acid o-Cresyl Ester.
(*14) 2,4-Di-t-octylhdyroquinone.
(*15) α-Pivaloyl-α-[(2,4,-dioxo-1-benzyl-5-ethoxy-hydantoin-3-yl)-2-chloro-5-[α-(2,4-di-t-amyl-phenoxy)butanamino]acetanilide.
(*16) Triethylammonium 3-[2-(3-benzylrhodanin-5-iridene)-3-benzoxazolinyl]propanesulfonate.
(*17) 2,4-Di-sec-octylhydroquinone.
(*18) Trinonyl phosphate.
(*19) 5-Chloro-2-(2-hydroxy-3-t-butyl-5-t-octyl)-phenylbenzotriazole.

Each layer further contained 1,4-bis(vinylsulfonylacetamido)ethane as a hardening agent and also a surface active agent.

Thus Sample 31 was prepared and was used as Comparison sample.

Then, Sample 32 was prepared by following the same procedure as above except that Magenta Coupler (M - 13) of this invention was used for Layer 5 (low-speed green-sensitive layer) and Layer 6 (high-speed green-sensitive layer as follows.

| Layer 5: Low-Speed Light-Sensitive Emulsion Layer | |
|---|---|
| Silver Iodobromide Emulsion (silver iodide 2.5 mol %, mean grain size 0.4 μm) spectrally sensitized by green sensitizing dye (*12) | 0.10 g/m² as silver |
| Gelatin | 0.70 g/m² |
| Magenta Coupler (M-13) | 0.40 g/m² |
| Fading Preventing Agent A (*10) | 0.07 g/m² |
| Fading Preventing Agent B (*9) | 0.02 g/m² |
| Coupler Solvent (*7) | 0.59 g/m² |
| Layer 6: High-Speed Green-Sensitive Emulsion Layer | |
| Silver Iodobromide Emulsion (silver iodide 3.5 mol %, mean grain size 0.9 μm) spectrally sensitized by green sensitizing dye | 0.10 g/m² as silver |
| Gelatin | 0.70 g/m² |
| Magenta Coupler (M-13) | 0.40 g/m² |
| Fading Preventing Agent A (*10) | 0.07 g/m² |
| Fading Preventing Agent B (*9) | 0.02 g/m² |
| Coupler Solvent (*7) | 0.59 |

Then, Sample 33 was prepared by following the same procedure as the case of preparing Sample 31 except that Magenta Coupler (M - 13) of this invention was used for Layer 5 (low-speed green-sensitive emulsion) and Layer 6 (high speed green-sensitive emulsion) as follows.

| Layer 5: Low-Speed Green-Sensitive Emulsion Layer | |
|---|---|
| Silver Iodobromide Emulsion (silver iodide 2.5 mol %, mean grain size 0.4 μm) spectrally sensitized by green sensitizing dye | 0.10 g/m² as silver |
| Gelatin | 0.70 g/m² |
| Magenta Coupler (M-13) | 0.40 g/m² |
| Fading Preventing Agent A (*10) | 0.07 g/m² |
| Fading Preventing Agent B (*9) | 0.02 g/m² |
| Coupler Solvent (P-80) | 0.59 g/m² |
| Layer 6: High-Speed Green-Sensitive Emulsion Layer | |
| Silver Iodobromide Emulsion (silver | |

| | |
|---|---|
| iodide 3.5 mol %, mean grain size 0.9 m) spectrally sensitized by green sensitizing dye (*12) | 0.10 g/m² as silver |
| Gelatin | 0.70 g/m² |
| Magenta Coupler (M-13) | 0.40 g/m² |
| Fading Preventing Agent A (*10) | 0.07 g/m² |
| Fading Preventing Agent B (*9) | 0.02 g/m² |
| Coupler Solvent (P-80) | 0.59 g/m² |

Each of Samples 31 to 33 thus prepared was wedge-exposed according an ordinary manner and then processed by the same conditions and processing liquids as in Example 6. The photographic properties of these samples thus processed were measured. The results thus obtained are shown in Table 11 below. In this case, the density measurement was performed by using Fuji FSD 103, made by Fuji Photo Film Co., Ltd.

TABLE 13

| Sample No. | Amount of Silver (g/m²) | Maximum Coloring Density | Color Image Stability | |
|---|---|---|---|---|
| | | | Residue (%)* | Stain** |
| 31 | 1.18 | 2.43 | 85 | 0.12 |
| 32 | 1.18 | 2.69 | 90 | 0.09 |
| 33 | 1.17 | 2.78 | 96 | 0.07 |

*Residual ratio of magenta density after xenon light (100,000 lux) irradiation of 12 days.
**[Yellow stain density after placing for 6 weeks at 60° C., 70% RH] − [Yellow stain density of fresh sample]
Samples 31 and 32: Comparison samples.
Sample 33: Sample of this invention.

From the results shown in the above table, it can be seen that Sample 33 using the magenta coupler of this invention and the high-boiling organic solvent defined in this invention shows excellent coloring density, is excellent color image stability, and is low in the formation of stain lowering the image quality. Also, the color images obtained show clear magenta color having high saturation.

EXAMPLE 12

Sample 41 was prepared by forming, in succession, Layer 1 to Layer 12 shown below on a triacetate film base.

Layer 1: Antihalation Layer

An emulsion (hereinafter, is referred to as Emulsion (a)) obtained by stirring 15 g of ultraviolet absorbents, 5-chloro-2-(2-hdyroxy-3,5-di-t-butylphenyl)-2H-benzotriazole, 30 g of 2,(2-hydroxy-5-t-butylphenyl)-2H-benzotriazole, 35 g of 2-(2-hydroxy-3-sec-butyl-5-t-butylphenyl)-2H-benzotriazole, and 100 g of dodecyl-5-(N,N-diethylamino)-2-benzenesulfonyl-2,4-pentadienoate and 200 ml of tricresyl phosphate, 200 ml of ethyl acetate, 20 g of sodium dodecylbenzenesulfonate, and an aqueous 10% gelatin solution at high speed was mixed with an aqueous 10% gelatin solution, black colloid silver, water, and a coating aid and the resultant mixture was coated on the support at a dry thickness of 2 μm.

Layer 2: Gelatin Interlayer

In 100 ml of dibutyl phthalate and 100 ml of ethyl acetate was dissolved 2,5-di-t-octylhydroquinone and the solution was mixed with 1 kg of an aqueous 10% gelatin solution at high speed to provide an emulsion (hereinafter, is referred to as Emulsion (b)). Then, 2 kg of Emulsion (b) was mixed with 1.5 kg of an aqueous 10% gelatin solution and the mixture was coated on the above layer at a dry thickness of 1 μm. The above hydroquinone compound was used in an amount of 40 mg/m².

Layer 3: Low-Speed Red-Sensitive Emulsion Layer

In 100 ml of tricresyl phosphate and 100 ml of ethyl acetate was dissolved 100 g of a cyan coupler, 2-(heptafluorobutylamido)-5-{2'-(2",4"-di-t-aminophenoxy)-butylamido}-phenol and the solution was mixed with 1 kg of an aqueous 10% gelatin solution at high speed to provide Emulsion (c). Then, 500 g of Emulsion (c) was mixed with 1 kg of a red-sensitive silver iodobromide emulsion (containing 70 g of silver and 60 g of gelatin and having an iodine content of 4 mol %) and the mixture obtained was coated on the above layer at a dry thickness of 1 μm (silver coverage of 0.5 g/m²).

Layer 4: High-Speed Red-Sensitive Emulsion Layer

A mixture of 50 g of Emulsion (c) prepared as above and 1 kg of a red-sensitive silver chlorobromide emulsion (containing 70 g of silver and 60 g of gelatin and having an iodine content of 2.5 mol %) was coated on the above layer at a dry thickness of 2.5 μm (silver coverage of 0.8 g/m²).

Layer 5: Interlayer

A mixture of 1 kg of Emulsion (b) prepared as above and 1 kg of an aqueous 10% gelatin solution was coated on the above layer at a dry thickness of 1 μm.

Layer 6: Low-Sensitive Green-Sensitive Emulsion Layer

By following the same procedure as the case of preparing emulsion for Layer 3 above using the magenta coupler shown below in place of the cyan coupler and using di-iso-octadecyl phthalate, Emulsion (d) was prepared.

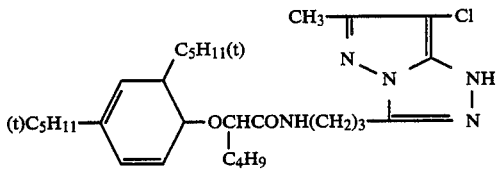

Then, 300 g of Emulsion (d) was mixed with 1 kg of a green-sensitive silver iodobromide emulsion (containing 70 g of silver and 60 g of gelatin and an iodine content of 3 mol %) and the mixture obtained was coated on the above layer at a dry thickness of 2.0 μm (silver coverage of 0.7 g/m²).

Layer 7: High-Speed Green-Sensitive Emulsion Layer

A mixture of 1,000 g of Emulsion (d) prepared as above and 1 kg of a green-sensitive silver iodobromide emulsion (containing 70 g of silver and 60 g of gelatin and having an iodine content of 2.5 mol %) was coated on the above layer at a dry thickness of 2.0 μm (silver coverage of 0.7 g/m²).

Layer 8: Gelatin Interlayer

A mixture of 1 kg of Emulsion (b) prepared as above and 1 kg of an aqueous 10% gelatin solution was coated on the above layer at a dry thickness of 0.5 μm.

Layer 9: Yellow Filter Layer

An emulsion containing yellow colloid silver was coated on the above layer at a dry thickness of 1 μm.

Layer 10: Low-Speed Blue-Sensitive Emulsion Layer

By following the same procedure as the case of preparing the emulsion for Layer 3 using a yellow coupler, α-(pivaloul)-α-(1-benzyl-5-ethoxy-3-hydantoinyl)-2-chloro-5-dodecyloxycarbonylacetanilide in place of the cyan coupler, Emulsion (e) was prepared. Then, 1000 g of Emulsion (e) was mixed with 1 kg of a blue-sensitive silver iodobromide emulsion (containing 70 g of silver and 60 g of gelatin and having an iodine content of 2.5 mol %) and the mixture obtained was coated on the above layer at a dry thickness of 1.5 μm (silver coverage of 0.6 g/m$^2$).

Layer 11: High-Speed Blue-Sensitive Emulsion Layer

A mixture of 1000 g of Emulsion (e) prepared as above and 1 kg of a blue-sensitive silver iodobromide emulsion (containing 70 g of silver and 60 g of gelatin and having an iodine content of 2.5 mol %) was coated on the above layer at a dry thickness of 3 μm (silver coverage of 1.1 g/m$^2$).

Layer 12: Second Protective Layer

A mixture of Emulsion (a) prepared as above, an aqueous 10% gelatin solution, water, and a coating aid was coated on the above layer at a dry thickness of 2 μm.

Layer 13: First Protective Layer

An aqueous 10% gelatin solution containing a surface fogged fine silver halide grain emulsion (grain size 0.06 μm, silver iodobromide emulsion containing 1 mol % iodine) was coated on the layer at a dry thickness of 0.8 μm and a silver coverage of 0.1 g/m$^2$.

Each layer further contained 1,4-bis(vinylsulfonylacetamido)ethane as a gelatin hardening agent and a surface active agent.

Then, Sample 42 was prepared by the same procedure as the case of preparing Sample 41 except that Magenta Coupler (M - 8) of this invention was used for Layer 6 (low-speed green-sensitive emulsion layer) and Layer 7 (high-speed green-sensitive emulsion layer) as follows.

Layer 6: Low-Speed Green-Sensitive Emulsion Layer

By following the same procedure as the case of preparing the emulsion for Layer 3 using Magenta Coupler (M - 8) of this invention, Emulsion (f) was prepared. Equimolar amounts of Emulsion (f) and Emulsion (d) prepared as above were mixed with 500 g of a green-sensitive silver iodobromide emulsion (containing 35 g of silver and 30 g of gelatin and having an iodine content of 3 mol %) and the mixture was coated at a dry thickness of 2.0 μm (silver coverage 0.35 g/m$^2$).

Layer 7: High-Speed Green-Sensitive Emulsion Layer

Equimolar amounts of Emulsion (d) and Emulsion (f) prepared as above were mixed with 500 g of a green-sensitive silver iodobromide emulsion (containing 35 g of silver and 30 g of gelatin and having an iodine content of 2.5 mol %) and the mixture was coated at a dry thickness of 2.0 μm (silver coverage of 0.35 g/m$^2$).

Then, Sample 43 was prepared by following the same procedure as above except that Magenta Coupler (M - 8) of this invention and High-Boiling Organic Solvent (P - 48) of this invention were used and also Emulsion (g) prepared by the same manner as preparing the emulsion for Layer 3.

Each of Samples 41 to 43 thus prepared was wedge-exposed according to an ordinary method and then processed by the same condition and processing liquids as used in Example 7. The photographic properties of these sample thus processed were measured and the results obtained are shown in Table 12 below. The density measurement was performed using Fuji FSD-103.

TABLE 12

| Sample No. | Amount of Ag (g/m$^2$) | Maximum Coloring Density | Image Stability Residue (%)* | Stain** |
|---|---|---|---|---|
| 41 | 4.8 | 3.15 | 87 | 0.08 |
| 42 | 4.8 | 3.34 | 92 | 0.06 |
| 43 | 4.8 | 3.52 | 96 | 0.04 |

*Residual ratio of magenta density after xenon irradiation (100,000 lux) of 4 days.
**[Yellow stained density after placing 4 weeks at 60° C. and 70% RH] − [Yellow stained density of fresh sample]

From the results shown in the above table, it can be seen that Sample 43 using the magenta coupler of this invention and the high-boiling point-organic solvent of this invention gives excellent coloring density and also shows the possibility of reducing silver amount. Also, the sample of this invention is excellent in stability of color images, gives less formation of stain, and is very advantageous as printing materials on considering together the results in the previous example. Furthermore, the magenta images obtained using the sample of this invention show clear hue having high saturation.

EXAMPLE 13

Sample 51 was prepared by forming Layer 1 to Layer 3 having the compositions shown below on a paper support having polyethylene coating on both surfaces thereof. In addition, the polyethylene coating layer on the support at the emulsion layer-carrying side contained titanium white and a slight amount of ultramarine blue.

| Layer 1: Green-Sensitive Emulsion Layer | |
|---|---|
| Silver Iodobromide Emulsion (silver bromide 70 mol %) | 0.13 g/m$^2$ as silver |
| Magenta Coupler (M - 2) | 3.7 × 10$^{-3}$ mol |
| Coupler Solvent (P - 87) | 0.5 g/m$^2$ |
| Fading Preventing Agent (*-3 in Example 1) | 0.19 g/m$^2$ |
| Gelatin | 1.35 g/m$^2$ |
| Layer 2 | |
| Ultraviolet Absorbent (VII - 2) | 8.0 × 10$^{-4}$ mol |
| Ultraviolet Absorbent Solvent (P - 54) | 0.35 g/m$^2$ |
| Gelatin | 2.08 g/m$^2$ |
| Layer 3 | |
| Gelatin | 1.5 g/m$^2$ |

Also, Samples 52 to 55 were prepared by following the above procedure using other ultraviolet absorbent(s) in this invention shown in Table 13 below as the ultraviolet absorbent for Layer 2.

Each of the samples thus prepared was light-exposed through a grey wedge and processed using the processing conditions and processing liquids in Example 1 (in this example, however, so-called washless processing was performed). About the samples thus processed, the light fastness was evaluated as follows. That is, the residual ratio (%) of the density (D$_G$) of initial density of 1.0 after xenon light irradiation (100,000 lux) of 4 days or 12 days was measured and the result was used for the evaluation of the light fastness.

The results thus obtained are shown in Table 13 below.

TABLE 13

| | | | Light Fastness | |
|---|---|---|---|---|
| Sample No. | Ultraviolet Absorbents and Coated Amount Thereof | | Residue* (4 days) (100,000 lux) 4 days | Residue* (12 days) (100,000 lux) 12 days |
| 51 | VII - 2 | $8.0 \times 10^{-4}$ mol/m² | 96 | 92 |
| 52 | VII O 3 | " | 97 | 93 |
| 53 | { VII - 3 | $4.0 \times 10^{-4}$ " | 99 | 97 |
| | VIII- 1 | $4.0 \times 10^{-4}$ | | |
| 54 | { VII - 1 | $2.0 \times 10^{-4}$ " | 98 | 96 |
| | VII - 3 | $4.0 \times 10^{-4}$ " | | |
| | VIII - 1 | $2.0 \times 10^{-4}$ " | | |
| 55 | { VII - 1 | $2.0 \times 10^{-4}$ " | 98 | 96 |
| | VII - 3 | $4.0 \times 10^{-4}$ " | | |
| | IX - 1 | $2.0 \times 10^{-4}$ | | |
| 56 | No Ultraviolet Absorbent Gelatin Only | | 91 | 56 |

*Residual ratio of Density ($D_G$) at 1.0 of initial density after xenon irradiation.

The results of Table 13 show that excellent light fastness is obtained by the combination of the magenta coupler of this invention and the ultraviolet absorbent(s) in this invention.

EXAMPLE 14

In 20 of tricresyl phosphate and 20 ml of ethyl acetate was dissolved 10 g of a magenta coupler, 1-(2,4,6-trichlorophenyl)-3-{(2-chloro-5-tetradecanamido)anilino}-2-pyrazolin-5-one and the solution obtained was dispersed by emulsification in 80 g of an aqueous gelatin solution containing 8 ml of an aqueous solution of 1% sodium dodecylbenzenesulfonate.

Then, the emulsified dispersion was mixed with 145 g of a green-sensitive silver chlorobromide emulsion (containing 7 g of silver, bromine 50 mol %) and after adding thereto sodium dodecylbenzenesulfonate as a coating aid, the mixture was coated on a paper support having polyethylene coating on both surfaces thereof at a coupler coverage of 400 g/m². A gelatin protective layer (1 g/m² of gelatin) was formed on the layer to provide Sample A.

Also, emulsified dispersions were prepared as above by using the combinations shown in Table 14 below. By following the same procedure as above using the emulsified dispersions, Samples B to P were prepared respectively.

Each of the samples thus prepared was exposed at 1,000 lux for one second and processed by the same conditions and processing liquids as in Example 3.

Each of the samples having dye images thus formed was subjected a fading test by a xenon tester (200,000 lux) using a ultraviolet absorption filter absorbing light of 400 nm or less, made by Fuji Photo Film Co., Ltd., for 10 days. The density change of the portion having an initial density of 2.0 was measured by a Macbeth Densitometer, RD-514 Type (status filer AA filter). The results obtained are shown in Table 14 below.

TABLE 14

| Sample No. | Magenta Coupler | Dye Image Stabilizer | Amount of coupler (mol %) | Change of Magenta Density of Initial Density 2.0* |
|---|---|---|---|---|
| A | Comparison Magenta Coupler (a) | — | — | 0.27 |
| B | " | A-1 | 50 | 1.27 |
| C | " | A-4 | 50 | 0.88 |
| D | Comparison Magenta Coupler (b) | — | — | 0.15 |
| E | " | A-7 | 50 | 1.45 |
| F | " | A-43 | 20 | 1.12 |
| G | Comparison Magenta Coupler (c) | — | — | 0.23 |
| H | " | A-5 | 50 | 1.53 |
| I | " | A-21 | 50 | 1.05 |
| J | (M - 7) | — | — | 0.34 |
| K | " | A-1 | 50 | 1.79 |
| L | " | A-7 | 50 | 1.76 |
| M | " | A-10 | 50 | 1.78 |
| N | (M - 10) | A-12 | — | 0.38 |
| O | " | A-12 | 50 | 1.80 |
| P | " | A-36 | 20 | 1.82 |

(*): Value of density ($D_G$) after xenon light irradiation.
Samples A to J and Sample N: Comparison Example.
Samples K to M and Samples O and P: Samples of this invention.

The composition magenta couplers used above were as follows.

Comparison Magenta Coupler (a):

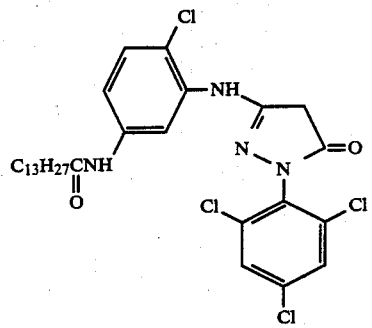

Comparison Magenta Coupler (b)

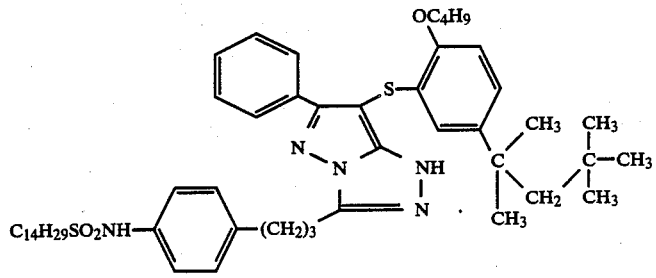

Compound described in Japanese Patent Application (OPI) No. 125,723/84

Comparison Magenta Coupler (c)

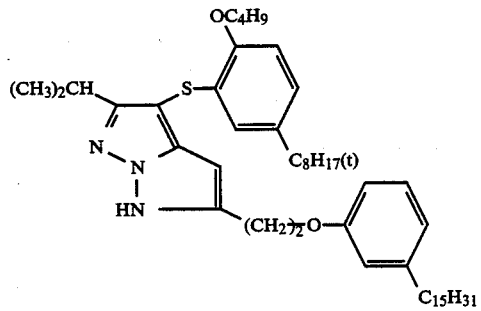

Compound described in Japanese Patent Application (OPI) No. 97353/85

From the results shown in Table 14, it can be seen that the combination of the magenta coupler of this invention and the dye image stabilizer of this invention gives excellent light fastness improving effect.

EXAMPLE 15

A multilayer color photographic light-sensitive material was prepared by forming Layer 1 to Layer 11 shown below on a paper support having polyethylene coating on both surfaces thereof. In addition, the polyethylene coating layer on the support at the emulsion layer-carrying side contained titanium white as a white pigment and a slight amount of ultramarine blue as a bluish dye.

| Layer 1: Antihalation Layer | |
|---|---|
| Black Colloid Silver | 0.10 g/m$^2$ |
| Gelatin | 2.00 g/m$^2$ |
| Layer 2: Low-Speed Red-Sensitive Emulsion Layer | |
| Silver Iodobromide Emulsion (silver iodide 3.5 mol %, mean grain size 0.7 μm) spectrally sensitized by red sensitizing dyes (*5 and *4) | 0.10 g/m$^2$ as silver |
| Gelatin | 1.00 g/m$^2$ |
| Cyan Coupler (*3) | 0.30 g/m$^2$ |
| Fading Preventing Agent (*2) | 0.15 g/m$^2$ |
| Coupler Solvents (*18 and *1) | 0.06 g/m$^2$ |
| Layer 3: High-Speed Red-Sensitive Emulsion Layer | |
| Silver Iodobromide Emulsion (silver iodide 8.0 mol %, mean grain size 0.7 μm) | 0.10 g/m$^2$ as silver |
| Gelatin | 0.50 g/m$^2$ |
| Cyan Couple (*3) | 0.10 g/m$^2$ |
| Fading Preventing Agent (*2) | 0.05 g/m$^2$ |
| Coupler Solvents (*18 and *1) | 0.02 g/m$^2$ |
| Layer 4: Interlayer | |
| Yellow Colloid Silver | 0.02 g/m$^2$ |
| Gelatin | 1.00 g/m$^2$ |
| Color Mixing Preventing Agent (*14) | 0.08 g/m$^2$ |
| Color Mixing Preventing Agnet Solvent (*13) | 0.16 g/m$^2$ |
| Polymer Latex (*6) | 0.10 g/m$^2$ |
| Layer 5: Low-Speed Green-Sensitive Emulsion Layer | |
| Silver Iodobromide Emulsion (silver iodide 2.5 mol %, mean grain size 0.4 μm) spectrally sensitized by | 0.20 g/m$^2$ |

|  |  |
|---|---|
| -continued | |
| green sensitizing dye (*12) | as silver |
| Gelatin | 0.70 g/m² |
| Magenta Coupler (*11) | 0.40 g/m² |
| Fading Preventing Agent A (*10) | 0.05 g/m² |
| Fading Preventing Agent B (*9) | 0.05 g/m² |
| Fading Preventing Agent C (*8) | 0.02 g/m² |
| Coupler Solvent (*7) | 0.15 g/m² |
| Layer 6: High-Speed Green-Sensitive Emulsion Layer | |
| Silver Iodobromide Emulsion (silver iodide | 3.5 mol %, mean grain size |
| 0.9 μm) spectrally sensitized by green sensitizing dye (*12) | 0.20 g/m² as silver |
| Gelatin | 0.70 g/m² |
| Magenta Coupler (*11) | 0.40 g/m² |
| Fading Preventing Agent A (*10) | 0.05 g/m² |
| Fading Preventing Agent B (*9) | 0.05 g/m² |
| Fading Preventing Agent C (*8) | 0.02 g/m² |
| Coupler Solvent (*7) | 0.15 g/m² |
| Layer 7: Yellow Filter Layer | |
| Yellow Colloid Silver | 0.20 g/m² |
| Gelatin | 1.00 g/m² |
| Color Mixing Preventing Agent (14) | 0.06 g/m² |
| Color Mixing Preventing Agent Solvent (*13) | 0.24 g/m² |
| Layer 8: Low-Speed Blue-Sensitive Emulsion Layer | |
| Silver Iodobromide Emulsion (silver iodide 2.5 mol %, mean grain size 0.5 μm) spectrally sensitized by blue sensitizing dye (*16) | 0.15 g/m² as silver |
| Gelatin | 0.50 g/m² |
| Yellow Coupler (*15) | 0.20 g/m² |
| Coupler Solvent (*18) | 0.05 g/m² |
| Layer 9: High-Speed Blue-Sensitive Emulsion Layer | |
| Silver Iodobromide Emulsion (silver iodide | 2.5 mol %, mean grain size |
| 1.4 μm) spectrally sensitized by blue sensitizing dye (*16) | 0.20 g/m² as silver |
| Gelatin | 0.50 g/m² |
| Yellow Coupler (*15) | 0.20 g/m² |
| Coupler Solvent (*18) | 0.05 g/m² |
| Layer 10: Ultraviolet Absorption Layer | |
| Gelatin | 1.50 g/m² |
| Ultraviolet Absorbent (*19) | 1.00 g/m² |
| Ultraviolet Absorbent Solvent (*18) | 0.30 g/m² |
| Color Mixing Preventing Agnet (*17) | 0.08 g/m² |
| Layer 11: Protective Layer | |
| Gelatin | 1.00 g/m² |
| Hardening Agent (*20) | 0.17 g/m² |

The compounds used in this case were as follows.
(*1) Dioctyl Phthalate
(*2) 2-(2-Hydroxy-3-sec-butyl-5-t-butylphenyl)-benzotriazole.
(*3) 2-[α-(2,4-Di-t-amylphenoxy)butanamido]-4,6-dichloro-5-ethylphenol.
(*4) 5,5'-Dichloro-3,3'-di(3-sulfobutyl)-9-ethylthiacarbocyanine Sodium Salt.
(*5) Triethylammonium 3-[2-{2-[3-(3-sulfopropyl)-naphtho(1,2-d)thiazolin-2-iridenemthyl]-1-butenyl{-3-naphtho(1,2-d)thiazolino]propane-sulfonate.
(*6) Polyethyl Acrylate.
(*7) Phosphoric Acid Octyl Ester.
(*8) 2,4-Di-t-hexylhydroquinone.
(*9) Di-(2-hydroxy-3-t-butyl-5-methylphenyl)methane.
(*10) 3,3,3',3'-Tetramethyl-5,6,5',6'-tetrapropoxy-1,1'-bisspiroindane.
(*11) 1-(2,4,6-Trichlorophenyl)-3-(2-chloro-5-tetradecanamido)anilino-2-pyrazolino-5-one.
(*12) 5,5'-Diphenyl-9-ethyl-3,3'-disulfopropyl-oxacarbocyanine Sodium Salt.
(*13) Phosphoric Acid o-Cresyl Ester.
(*14) 2,4-Di-t-octylhydroquinone.
(*15) α-Pivaloyl-α-[(2,4-dioxo-1-benzyl-5-ethoxy-hydantoin-3-yl)-2-chloro-5-(α-2,4-dioxo-t-amylphenoxy)butanamido]acetanilide.
(*16) Triethylammonium 3-[2-(3-benzylrhodanin-5-iridene)-3-benzoxazolinyl-]propanesulfonate.
(*17) 2,4-Di-sec-octylhydroquinone.
(*18) Phosphoric Acid Trinonyl Ester.
(*19) 5-Chloro-2-(2-hydroxy-3-t-butyl-5-t-octyl)-phenylbenztriazole.
(*20) 1,4-Bis(vinylsulfonylacetamido)ethane.

Thus, Sample 101 was prepared and was uses as a comparison sample in this invention.

Then, by following the same procedure as above using the magenta couplers and the additives shown in Table 15 described below in place of Magenta Coupler (*11) and the additive for Layer 5 and Layer 6 of Sample 101, Samples to 119 were prepared respectably.

Each of the samples thus prepared was step-exposed for sensitometry, processed by the following processing steps, and the photographic properties thereof were measured using FAD (automatic measurement device, made by Fuji Photo Film Co., Ltd.). The results obtained are shown in Table 15 below.

| Processing Step | | |
|---|---|---|
| First Development (Black and White Development) | 38° C. | 1 min. 15 sec. |
| Wash | 38° C. | 1 min. 30 sec. |
| Reversal Exposure | above 100 lux | above 1 sec. |
| Color Development | 38° C. | 2 min. 15 sec. |
| Wash | 38° C. | 45 sec. |
| Blix | 38° C. | 2 min. 00 sec. |
| Wash | 38° C. | 2 min. 15 sec. |

The compositions of the processing liquids used in the above processing steps were as follows.

| First Developer | |
|---|---|
| Nitrilo-N,N,N—trimethylene Phosphoric Acid Penta-sodium Salt | 0.6 g |
| Diethylenetriaminepentaacetic Acid Pentasodium Salt | 4.0 g |
| Potassium Sulfite | 30.0 g |
| Potassium Thiocyanate | 1.2 g |
| Potassium Carbonate | 35.0 g |
| Hydroquinone Monosulfonate Potassium Salt | 25.0 g |
| Diethylene Glycol | 15.0 ml |
| 1-Phenyl-4-hydroxy-methyl-4-methyl-3-pyrazolidone | 2.0 g |
| Potassium Bromide | 0.5 g |
| Potassium Iodide | 5.0 mg |
| Water to make | 1 liter |
| | (pH 9.70) |
| Color Developer | |
| Benzyl Alcohol | 15.0 ml |
| Diethylene Glycol | 12.0 ml |
| 3,6-Dithia-1,8-octanediol | 0.2 g |
| Nitrilo-N,N,N—trimethylenephosphonic Acid Penta-sodium Salt | 0.5 g |
| Diethylenetriaminepentaacetic Acid Penta-sodium Salt | 2.0 g |
| Sodium Sulfite | 2.0 g |
| Potassium Carbonate | 25.0 g |
| Hydroxylamine Sulfate | 3.0 g |
| N—Ethyl-N—(β-methanesulfonamido-ethyl)-3-methyl-4-aminoaniline Sulfate | 5.0 g |
| Potassium Bromide | 0.5 g |
| Potassium Iodide | 1.0 mg |
| Water to make | 1 liter |
| | (pH 10.40) |
| Blix Liquid | |
| 2-Mercapto-1,3,4-triazole | 1.0 g |
| Ethylenediaminetetraacetic Acid Disodium Salt.Dihydrate | 5.0 g |
| Ethylenediaminetetraacetic Acid Iron(III) Ammonium Salt Mono-hydrate | 80.0 g |
| Sodium Sulfite | 15.0 g |
| Sodium Thiosulfate (soln. of 700 g/liter) | 160.0 ml |
| Glacial Acetic Acid | 5.0 ml |
| Water to make | 1 liter |
| | (pH 6.50) |

Additives (*21) and (822) shown in Table 15 below were as follows.

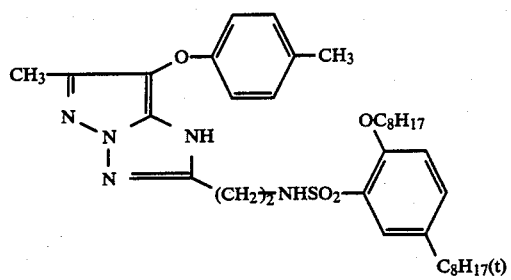

Compound (*21)

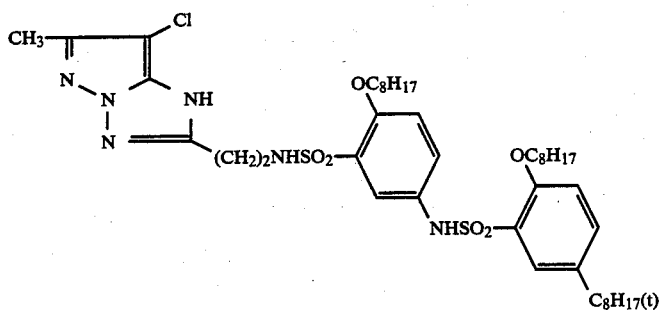

Compound (*22)

TABLE 15

| Samples | Magenta Coupler in Layer 5 and Layer 6 Compound | Magenta Coupler in Layer 5 and Layer 6 Amount | Additive in Layer 5 and Layer 6 | Magenta Color Purity (DR + DB/DG) | Relative Sensiti- vity *1 | Dmin (DG) *2 | Increase of Stain *3 ΔDB |
| --- | --- | --- | --- | --- | --- | --- | --- |
| 101 | *11 | Same as above | — | 0.475 | 100 | 0.00 | 0.18 |
| 102 | *21 | | — | 0.184 | 99 | 0.08 | 0.03 |
| 103 | *21 | | (XV-27) | 0.184 | 90 | 0.05 | 0.04 |
| 104 | *22 | | — | 0.175 | 101 | 0.15 | 0.04 |
| 105 | *22 | | (XV-16) | 0.175 | 89 | 0.10 | 0.04 |
| 106 | XI-10 | | — | 0.168 | 97 | 0.03 | 0.2 |
| 107 | " | | (XV-27) | 0.168 | 93 | 0.00 | 0.01 |
| 108 | XI-23 | | — | 0.178 | 98 | 0.04 | 0.02 |
| 109 | " | 7/10 mol | (XV-16) | 0.178 | 93 | 0.00 | 0.01 |
| 110 | *21 | of | (XIV-1) | 0.184 | 94 | 0.06 | 0.04 |
| 111 | *22 | Sample 101 | (XIV-12) | 0.175 | 90 | 0.11 | 0.04 |
| 112 | XI-10 | | (XIV-1) | 0.168 | 95 | 0.00 | 0.01 |
| 113 | XI-23 | | (XIV-12) | 0.178 | 96 | 0.00 | 0.01 |
| 114 | *21 | | (XIIIa-4) | 0.184 | 95 | 0.07 | 0.04 |
| 115 | *22 | | " | 0.175 | 93 | 0.13 | 0.04 |
| 116 | XI-10 | | " | 0.167 | 96 | 0.01 | 0.01 |
| 117 | XI-23 | | " | 0.178 | 97 | 0.01 | 0.01 |
| 118 | XI-10 | | (XII-1) | 0.168 | 96 | 0.01 | 0.01 |
| 119 | XI-23 | | (XVIa-1) | 0.178 | 96 | 0.02 | 0.01 |

Samples 101 to 106, 108, 110, 111, 114 and 115: Comparison Example
Samples 107, 109, 112, 113 and 116 to 119: Sample of this Invention
*1 Sensitivity of Sample 101 is standardized as 100
*2 Dmin of Sample 101 is standardized as 0.00
*3 Increase of stain is measured using thermal fading testor The color purity in the above table shows the ratio $[(D_R+D_B)/D_G]$ of the sum of a cyan density ($D_R$) and a yellow density ($D_B$) to a magenta density ($D_G$) at the point that the magenta density ($D_G$) measured by Macbeth densitometer status AA filter in the case of step exposing each sample using Magenta Filter CC 200M (made by Fuji Photo Film Co., Ltd.) is 1.0. That is, the color purity is a measure indicating the surplus amounts of cyan and yellow components in magenta color and in generally, as the value is lower, the purity of color is higher, The increase of stain by thermal fading shown in the above table shows the value obtained by measuring the change of yellowish tint of a background portion of each sample after placing in a constant-temperature and constant humidity bath of 80° C. and 70% for 15 days using a blue filter.

From the results shown in Table 15 above, it can be seen that Samples 107, 109, 112, 113, and 116–119 of this invention have high color purity and restrain the formation of unnecessary color stain without substantially lowering the relative sensitivity.

EXAMPLE 16

A color photographic light-sensitive material was prepared by forming Layer 1 to Layer 3 shown below on a paper support having polyethylene coating on both surfaces thereof. In addition, the polyethylene coating layer on the paper support at the emulsion layer-carrying side contained titanium oxide as a white pigment and a slight amount of ultramarine blue as a bluish dye.

| Layer 1: Green-Sensitive Emulsion Layer | |
|---|---|
| Silver Chlorobromide Emulsion (silver bromide 70%) spectrally sensitized by green sensitizing dye (*31) | 0.30 g/m² as silver |
| Magenta Coupler (*32) | 0.25 g/m² |
| Magenta Coupler Solvent (*34) | 0.30 g/m² |
| Fading preventing Agent (*9) | 0.05 g/m² |
| Fading Preventing Agent (*10) | 0.10 g/m² |
| Gelatin | 1.00 g/m² |
| Layer 2: Ultraviolet Absorptive Interlayer | |
| Ultraviolet Absorbent (*33) | 0.50 g/m² |
| Ultraviolet Absorbent Solvent (DBP) | 0.20 |
| Gelatin | 0.15 |
| Layer 3: Protective layer | |
| Gelatin | 1.50 g/m² |

DBP: Dibutyl phthalate.
Compounds (*31) to (*34) used above were as follows.

*31
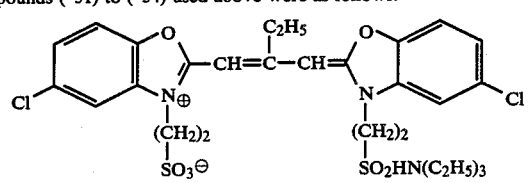

*32
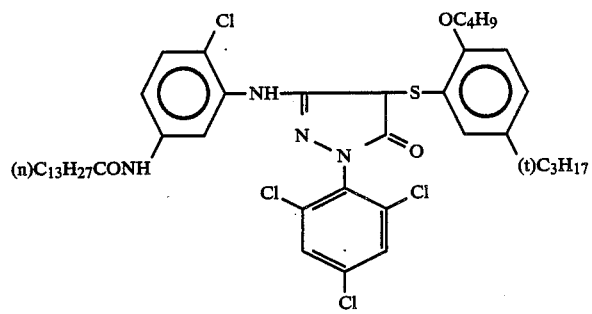

*33
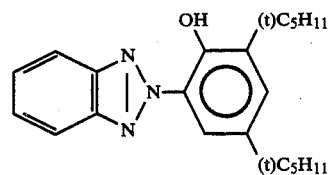

*34
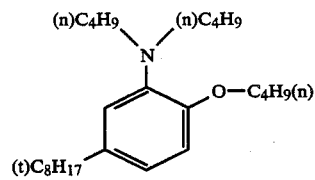

In this case, each Layers 1 and 3 described above contained a gelatin hardening agent, 2,4-dichloro-6-hydroxy-1,3,5-triazine sodium salt.

Thus, Sample 201 was prepared.

Then, by following the same procedure as above except that the components for Layer 1 were changed as shown in Table 16 below, Samples 202 to 208 were prepared.

Each of the samples this prepared was step-exposed for sensitometry using an enlarger (Fuji Color Head 609, trade name, made by Fuji Photo Film Co., Ltd.) and then processed as follows.

| Processing Step | | |
|---|---|---|
| Development | 33° C. | 3.5 min. |
| Blix | 33° C. | 1.5 min. |
| Wash | 28 to 35° C. | 3.0 min. |
| Developer | | |
| Nitrilotriacetic Acid 3Na | | 2.0 g |
| Benzyl Alcohol | | 15 ml |
| Diethylene Glycol | | 10 ml |
| Sodium Sulfite | | 2.0 g |
| Potassium Bromide | | 0.5 g |
| Hydroxylamine Sulfate | | 3.0 g |
| 4-Amino-3-methyl-N—ethyl-N[β-methanesulfonamido)ethyl]-p-phenylenediamine Sulfate | | 5.0 g |
| Sodium Carbonate (monhydrate) | | 30 g |
| Water to make | | 1 liter |
| | | (pH 10.1) |
| Blix Liquid | | |

-continued

| | |
|---|---|
| Ammonium Thiosulfate (70%) | 150.0 ml |
| Sodium Sulfite | 15 g |
| NH$_4$[Fe(EDTA)] | 55 g |
| EDTA 2Na | 4.0 g |
| Water to make | 1 liter |
| | (pH 6.9) |

After processing, the characteristic curve (D-logE curve) was determined on each sample by a self-recording densitometer using blue, green, and yellow filters. The results obtained are shown in Table 17 below.

TABLE 16

| | (Layer 1) | | | | | | | |
|---|---|---|---|---|---|---|---|---|
| Sample No. | 201 | 202 | 203 | 204 | 205 | 206 | 207 | 208 |
| Magenta Coupler | (*32) | " | " | (*21) | " | XI-23 | " | " |
| Coated Amount of Coupler | 0.25 | " | " | " | " | " | " | " |
| Coupler Solvent | (*36) | " | " | (*13) | " | (*7) | " | " |
| Coated Amount of Solvent | 0.30 | " | " | " | " | " | " | " |
| Compound | — | XVIa-2 | XVIa-1 | — | XVIa-2 | — | XVIa-2 | XVIa-1 |
| Amount | — | (0.0012) | (0.0014) | — | (0.0012) | — | (0.0012) | (0.0014) |

Note:
The addition amounts of other components than those shown in the above table in Samples 202 to 208 were same as those in Sample 201.

TABLE 17

| Sample No. | Magenta Color Purity (D$_R$ + D$_B$/D$_G$) | Relative Sensitivity* | Density Change After Placing 7 days at 35° C. Since Exposure** |
|---|---|---|---|
| 201 | 0.453 | 100 | −0.06 |
| 202 | 0.453 | 101 | −0.03 |
| 203 | 0.452 | 99 | −0.04 |
| 204 | 0.142 | 93 | −0.16 |
| 205 | 0.145 | 95 | −0.13 |
| 206 | 0.144 | 98 | −0.12 |
| 207 | 0.145 | 99 | −0.02 |
| 208 | 0.144 | 98 | −0.03 |

(*) The sensitivity of Sample 201 was defined as 100.
(**) At the point of D = 1.0
Samples 201 to 206: Comparison Samples.
Samples 207 and 208: Samples of this invention.

The color purity in Table 17 is the value calculated by the formula [(D$_B$+D$_R$)/D$_G$] from the values of D$_B$ and D$_R$ at D$_G$=1.0 of magenta coloring at white light exposure, the meaning of which is the same as that in Example 1. Also, ΔDmin (D$_G$) shows the increased value of Dmin in the case allowing to stand each sample for 7 days under high-temperature and high-humidity conditions of 50° C. and 80% before exposure.

From the results shown in Table 17 above, it can be seen that pyrazoloazole series couplers are very excellent in color purity as compared with 5-pyrazolone type coupler but give undesirably high Dmin, while by using the combination of the specific pyrazoloazole series coupler and the additive according to this invention, desired photographic properties of lowered Dmin, etc., can be obtained substantially without lowering the sensitivity.

EXAMPLE 17

A silver halide color photographic material was prepared by forming Layer 1 to Layer 7 shown below on a paper support having polyethylene coating on both surfaces thereof. In addition, the polyethylene coating layer on the support at the emulsion layer-carrying side contained titanium dioxide and a slight amount of ultramarine blue.

| | |
|---|---|
| Layer 1: Blue-sensitive Emulsion Layer | |
| Silver Chlorobromide Emulsion (silver bromide 80 mol %) | 0.30 g/m$^2$ as silver |
| Yellow Coupler (*15) | 0.70 gm/m$^2$ |
| Coupler Solvent (TNP) | 0.15 g/m$^2$ |
| Gelatin | 1.20 g/m$^2$ |
| Layer 2: Interlayer | |
| Gelatin | 0.90 g/m$^2$ |
| Di-t-octylhydroquinone | 0.05 g/m$^2$ |
| Solvent (DBP) | 0.10 g/m$^2$ |
| Layer 3: Green-sensitive Emulsion Layer | |
| Silver Chlorobromide Emulsion (silver bromide 70 mol %) | 0.45 g/m$^2$ as silver |
| Magenta Coupler (*11) | 0.35 g/m$^2$ |
| Coupler Solvent (TOP) | 0.44 g/m$^2$ |
| Fading Preventing Agent (*9) | 0.05 g/m$^2$ |
| Fading Preventing Agent (*10) | 0.10 g/m$^2$ |
| Gelatin | 1.00 g/m$^2$ |
| Layer 4: Ultraviolet Absorptive Interlayer | |
| Ultraviolet Absorbent (*41) | 0.06 g/m$^2$ |
| Ultraviolet Absorbent (*42) | 0.25 g/m$^2$ |
| Ultraviolet Absorbent (*2) | 0.25 g/m$^2$ |
| Ultraviolet Absorbent Solvent (TNP) | 0.20 g/m$^2$ |
| Di-t-octylhydroquinone | 0.05 g/m$^2$ |
| Solvent (DBP) | 0.10 g/m$^2$ |
| Gelatin | 1.50 g/m$^2$ |
| LAyer 5: Red-Sensitive Emulsion Layer | |
| Silver Chlorobromide Emulsion (silver bromide 50 mol %) | 0.20 g/m$^2$ as silver |

-continued

| | |
|---|---|
| Cyan Coupler (*43) | 0.20 g/m² |
| Cyan Coupler (*44) | 0.20 g/m² |
| Coupler Solvent (TNP) | 0.10 g/m² |
| Coupler Solvent (DBP) | 0.20 g/m² |
| Gelatin | 0.90 g/m² |
| Layer 6: Ultraviolet Absorptive Interlayer | |
| Ultraviolet Absorbent (*41) | 0.06 g/m² |
| Ultraviolet Absorbent (*42) | 0.25 g/m² |
| Ultraviolet Absorbent (*2) | 0.25 g/m² |
| Ultraviolet Absorbent Solvent (DBP) | 0.20 g/m² |
| Gelatin | 1.50 g/m² |
| Layer 7: Protective Layer | |
| Gelatin | 1.50 g/m² |

DBP: Dibutyl Phthalate
TOP: Tri(n-octyl) Phosphate
TNP: Tri(n-nonyl) Phosphate (*41) 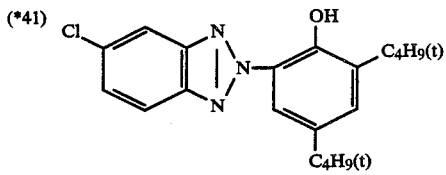

(*42) 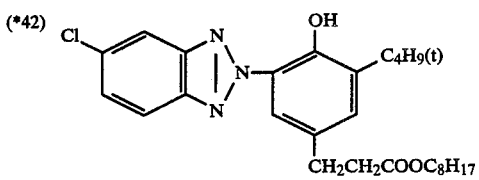

(*43) 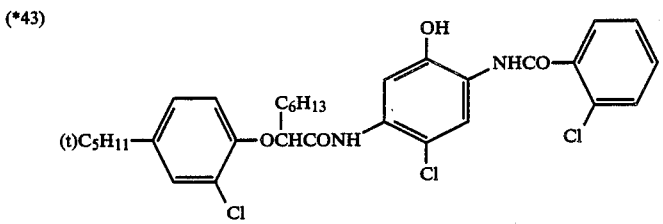

(*44) 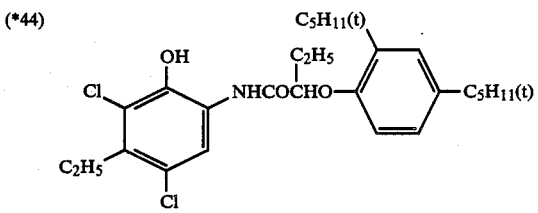

The following dye was used for each emulsion layer as a spectral sensitizer.

For Blue-Sensitive Emulsion Layer:

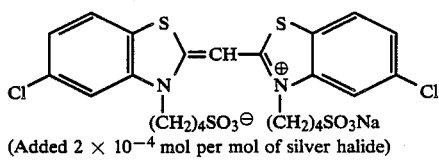

(Added $2 \times 10^{-4}$ mol per mol of silver halide)

For Green-Sensitive Emulsion Layer:

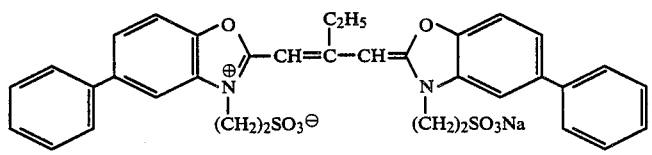

-continued (Added 2.5 × 10⁻⁴ mol per mol of silver halide)

For Red-Sensitive Emulsion Layer:

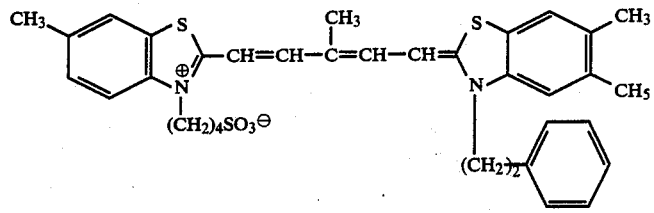

(Added 2.5 × 10⁻⁴ mol per mol of silver halide)

Also, the following dye was used for each emulsion layer as irradiation preventing dye.

For Green-Sensitive Emulsion Layer:

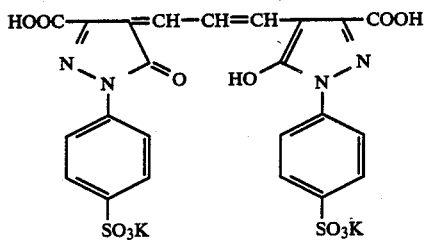

For Red-Sensitive Emulsion Layer:

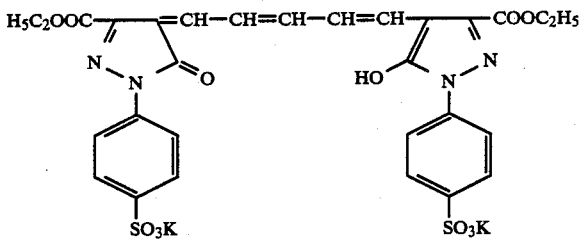

Thus, Sample 301 of silver halide color photographic material was prepared.

Then, by following the same procedure as above except that the couplers and additives for Layer 3 shown in Table 18 below, Samples 302 and 310 were prepared.

Each of the samples was step-exposed for sensitometery using an Enlarger (Fuji Color Head 609, made by Fuji Photo Co., Ltd.) and then processed by the following processing steps. Then, the photographic properties of these samples thus processed were measured and the results obtained are shown in Table 18 below.

| Processing Step | | |
|---|---|---|
| Color Development | 33° C. | 3 min. 30 sec. |
| Blix | 33° C. | 1 min. 30 sec. |
| Wash | 24–34° C. | 3 min. |
| Drying | 80° C. | 1 min. |

The compositions of the processing liquids used were as follows.

| Color Developer: | |
|---|---|
| Water | 800 ml |
| Diethylenetriaminepentaacetic Acid | 3.0 g |
| Benzyl Alcohol | 15 ml |
| Diethylene Glycol | 10 ml |
| Sodium Sulfite | 2.0 g |
| Potassium Bromide | 0.5 g |
| Potassium Carbonate | 30.0 g |
| N—Ethyl-N—(β-methanesulfonamidoethyl)-3-methyl-4-aminoaniline Sulfate | 5.0 g |
| Hydroxylamine Sulfate | 4.0 g |
| Optical Whitening Agent (4,4'-distilbene series) | 1.0 g |
| Water to make | 1 liter |
| | (pH 10.10 at 25° C.) |
| Blix Liquid: | |
| Water | 400 ml |
| Ammonium Thiosulfate (70% soln.) | 150 ml |
| Sodium Sulfite | 18 g |
| Ethylenediaminetetraacetic Acid Iron(III) Ammonium | 55 g |
| Ethylenediaminetetraacetic Acid.2Na | 5 g |
| Water to make | 1 liter |
| | (pH 6.70 at 25° C.) |

TABLE 18

| Sample No. | Coupler of Layer 3 | Amount of Coupler | Ag amount of Layer 3 | Additive of Layer 3 | Magenta Color Purity*¹ | Relative Sensitivity Sample 401 as 100) | Fog ($D_g$) | ΔFog($D_G$) (35° C.-80%-2W) | ΔDmin ($D_B$)*² |
|---|---|---|---|---|---|---|---|---|---|
| 301 | *11 | 0.35 | 0.45 | — | 0.527 | 100 | 0.18 | +0.03 | +0.16 |
| 302 | *22 | 0.27 | 0.23 | — | 0.262 | 98 | 0.21 | +0.13 | +0.08 |
| 303 | XI-10 | 0.30 | 0.22 | — | 0.252 | 98 | 0.19 | +0.08 | +0.04 |

TABLE 18-continued

| Sample No. | Coupler of Layer 3 | Amount of Coupler | Ag amount of Layer 3 | Additive of Layer 3 | Magenta Color Purity[*1] | Relative Sensitivity Sample 401 as 100 | Fog ($D_g$) | $\Delta Fog(D_G)$ (35° C.-80%-2W) | $\Delta Dmin (D_B)$[*2] |
|---|---|---|---|---|---|---|---|---|---|
| 304 | XI-10 | " | 0.22 | XV-27 | 0.253 | 101 | 0.20 | +0.04 | +0.04 |
| 305 | XI-23 | 0.30 | 0.21 | XV-27 | 0.251 | 100 | 0.18 | +0.03 | +0.05 |
| 306 | XI-10 | 0.30 | 0.22 | XV-16 | 0.253 | 100 | 0.20 | +0.04 | +0.04 |
| 307 | XI-10 | 0.30 | 0.22 | XIV-1 | 0.253 | 100 | 0.20 | +0.04 | +0.04 |
| 308 | XI-10 | 0.30 | 0.22 | XIIIa-4 | 0.253 | 101 | 0.20 | +0.04 | +0.04 |
| 309 | XI-10 | 0.30 | 0.22 | XII-2 | 0.252 | 97 | 0.18 | +0.02 | +0.04 |
| 310 | XI-23 | 0.30 | 0.21 | XVIa-2 | 0.251 | 100 | 0.18 | +0.03 | +0.05 |

[*1] $(D_R + D_B)/D_G$
[*2] Yellowish tone of print by humidity and heat.
Samples 301 to 303: Comparison Samples
Samples 304 to 310: Samples of this invention The magenta color purity in Table 18 above is same as that in Example 15. Also, in the above table, the yellowish tone of print by humidity and heat, i.e., $\Delta Dmin(D_B)$ is the increased value of yellow stain at the background portion of each print after processing occurred after allowing to stand for 6 weeks at 60° C. and 70% R.H.

From the results shown in Table 18 above, it can be seen that the samples of this invention (Samples 304 to 310) give preferred photographic properties (clearness of color, less increase of fog with the passage of time, less formation of yellowish tone of print, etc.,) without causing the reduction of sensitivity as compared with the comparison samples (Samples 301 to 303).

EXAMPLE 18

By following the same procedure as the case of preparing Sample 101 in Example 15, Sample 401 was prepared and uses a contrast sample.

Then, by following the same procedure as above by using magenta couplers and hardening agents as shown in Table 19 below in place of Magenta Coupler (*11) for Layers 5 and 6 and Hardening Agent (*20) for Layer 11 of Sample 401, Samples 402 to 411 were prepared.

These samples were step-exposed for sensitometery and processed by the processing steps as in Example 15. The photographic properties thereof measured are shown in Table 19 below.

TABLE 19

| Sample No. | Magenta Coupler for Layers 5 and 6[*1] | Hardening Agent of Layer 11 | Magenta Color Purity $[(D_R + D_B)/D_G]$ | Relative Sensitivity After 3 Months[*2] | Relative Sensitivity After 7 days Since Photographing |
|---|---|---|---|---|---|
| 401 | *11 | *20 | 0.475 | 87 | 90 |
| 402 | " | *23 | 0.477 | 82 | 91 |
| 403 | " | XVII-7 | 0.476 | 89 | 93 |
| 404 | *21 | *20 | 0.185 | 75 | 73 |
| 405 | *22 | *20 | 0.175 | 77 | 74 |
| 406 | *22 | XVII-7 | 0.178 | 83 | 82 |
| 407 | XI-23 | *20 | 0.177 | 81 | 78 |
| 408 | XI-10 | XVII-2 | 0.167 | 92 | 95 |
| 409 | " | XVII-4 | 0.168 | 94 | 95 |
| 410 | " | XVII-7 | 0.167 | 95 | 97 |
| 411 | XI-23 | " | 0.173 | 93 | 94 |

[*1] Amount of the magenta coupler is same in Samples 401 to 403. In other samples, the gradation of each layer was adjusted by reducing the amount of the silver halide of the layer to ½.
[*2] The intitial sensitivity was defined as 100.
Samples 401 to 407: Comparison Samples
Samples 408 to 411: Samples of this Invention In the above table, Samples 401 to 407 were comparison samples and Samples 408 to 411 were the samples of this invention.

*21

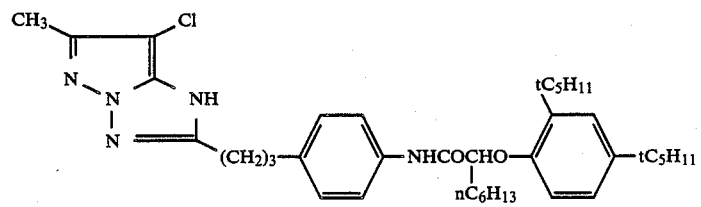

-continued

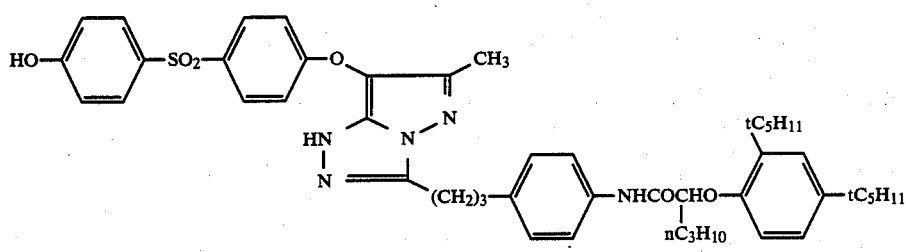
*22

HCHO  *23

The color purity in the above table was shown by the ratio $[(D_R+D_B)/D_G]$ of the sum of the cyan and yellow densities ($D_R$ and $D_B$) to the magenta density ($D_G$) at the portion of each sample that the magenta density measured by a Macbeth densitometer Status AA filter in the case of step-exposing the sample using two magenta filters CC100M (Fuji Photo Film Co., Ltd.). That is, the color purity is a measure for showing the amounts of surplus cyan and yellow components in magenta color and it can be generally said that as the value is smaller, the purity of the color is higher.

The storage condition for measuring the change of

Then, by following the same procedure as above except that the silver halide emulsions for Layers 2,3,5,6,8, and 9 and Magenta Coupler (*21) for Layer 5 and 6 were changed as shown in Table 20 below, Samples 502 to 508 were prepared.

Each of the samples thus prepared was step-exposed for sensitometery and processed by the developing processing as in Example 1. The photographic properties of the samples thus processed were measured by Fuji-Type self-recording density measurement device, made by Fuji Photo Film Co., Ltd. and the results obtained are shown in Table 20 below.

TABLE 20

| Sample No. | Magenta Coupler for Layers 5 and 6 | | | Dispersing Oil for Layers 5 and 6 | | | Ir-Content in Each Emulsion Layer (mol ratio to Ag) × $10^{-7}$ | | | | | |
|---|---|---|---|---|---|---|---|---|---|---|---|---|
| | | Amount (g/m²) | | | Amount (g/m²) | | | | | | | |
| | Kind | Layer 5 | Layer 6 | Kind | Layer 5 | Layer 6 | Layer 2 | Layer 3 | Layer 5 | Layer 6 | Layer 8 | Layer 9 |
| 501 | *21 | 0.40 | 0.40 | *17 | 0.25 | 0.25 | — | — | — | — | — | — |
| 502 | " | " | " | " | " | " | — | — | 1.2 | 2.0 | — | — |
| 503 | " | " | " | " | " | " | 0.2 | 0.2 | 0.6 | 0.8 | 0.4 | 0.5 |
| 504 | *31 | 0.25 | 0.25 | " | 0.156 | 0.156 | — | — | — | — | — | — |
| 505 | " | " | " | " | " | " | — | — | 1.2 | 2.0 | — | — |
| 506 | XI-10 | " | " | " | " | " | — | — | — | — | — | — |
| 507 | " | " | " | " | " | " | — | — | 1.2 | 2.0 | — | — |
| 508 | " | " | " | " | " | " | 0.2 | 0.2 | 0.6 | 0.8 | 0.4 | 0.5 |

(Note)
(1) In Samples 504 to 508, the coating amounts of not only the magenta coupler but also the silver halide emulsion, gelatin, fading preventing agent, etc., were the values multiplied by 0.625.
(2) Iridium was added to each silver halide emulsion at the formation of silver haldie grains.

densities with the passage of time were 35° C. and 55% RH.

From the results shown in Table 19 above, it can be seen that Samples 408 to 411 of this invention show high color purity and less change of densities with the passage of time.

EXAMPLE 19

By following the same procedure as the case of preparing Sample 401 in Example 18, Sample 501 was prepared and was used as a contrast sample.

In addition, Magenta Coupler (*21) shown in Table 20 is the same as in Example 18 shown above and Dispersion Oil (*17) is trioctylphosphate.

Also, Magenta Coupler (*31) is as follows.

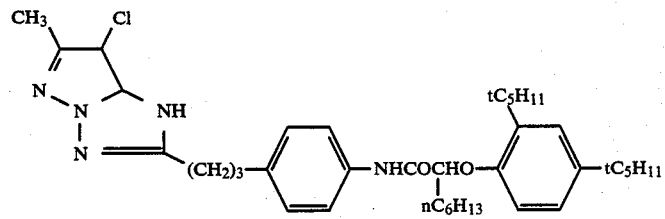

As described above, the photographic properties of the samples processed are shown in the following table.

TABLE 21

| Sample No. | Relative Sensitivity* | Change of Sensitivity (from 35° C. to 5° C.) | | | Change of Color Balance (D = 1.0) (from 35° C. to 5° C.) (1) | Color Purity |
| --- | --- | --- | --- | --- | --- | --- |
| | | Blue | Green | Red | | |
| 501 | 100 | 0.08 | 0.09 | 0.08 | 1G | 0.475 |
| 502 | 98 | 0.08 | 0.05 | 0.08 | 3M | 0.476 |
| 503 | 99 | 0.01 | 0.00 | 0.00 | 1Y | 0.475 |
| 504 | 76 | 0.08 | 0.18 | 0.08 | 10M | 0.174 |
| 505 | 75 | 0.08 | 0.16 | 0.08 | 8M | 0.174 |
| 506 | 89 | 0.08 | 0.14 | 0.08 | 6M | 0.173 |
| 507 | 96 | 0.08 | 0.05 | 0.08 | 3G | 0.169 |
| 508 | 95 | 0.00 | 0.00 | 0.00 | 0 | 0.170 |

(Note)
(1) The color balance is shown by the deviation of color balance in the case of performing light exposure under the same exposure conditions as those of giving gray density of 1.0 of print at 35° C. except for performing at 5° C., "3M" of change of color balance means 0.03 magenta hue. Less value of change of color balance means that color hue of print is hardly influenced by exposing temperature, which is perferable result.
(2) The color purity has the same meaning as in Example 15 and was obtained by the ratio at the portion that the magenta density $D_G$ was 1.0.
Also, the magenta color was obtained by wedge exposure using two Fuji Gelatin Filters CC100M.
*Green sensitive layer From the results shown in Table 21, it can be seen that a pyrazoloazole series coupler giving good color purity is has low sensitivity, has large temperature dependence at printing, and largely changes color balance by temperature as compared to 5-pyrazolone couplers and hence such a coupler is generally considered to be undesirable but by combining the specific pyrazoloazole series coupler in this invention and the silver halide emulsion using iridium as defined in this invention, the above-described disadvantages can be eliminated.

EXAMPLE 20

A multilayer color photographic paper was prepared by forming Layer 1 to Layer 7 shown below on a paper support having polyethylene coating on both surfaces thereof. In addition, the polyethylene coating layer on the support at the emulsion layer-carrying surface contained titanium dioxide as a white pigment and ultramarine blue as a bluish dye.

The coating liquids for the layers were prepared as follows.

Preparation of Coating Liquid for Layer 1:

In 10 ml of ethyl acetate and 3.1 ml of Solvent (c) were dissolved 10 g of Yellow Coupler (a) and 2.3 g of Dye Image Stabilizer (b) and the solution obtained was dispersed by emulsification in 90 ml of an aqueous 10% gelatin solution containing 10 ml of 1% sodium dodecylbenzensulfonate solution. On the other hand, 95 g of a blue-sensitive silver halide emulsion was prepared by adding the blue-sensitizing dye shown below to a silver chlorobromide emulsion (containing 80 mol % silver bromide and 70 g/kg of silver) in an amount of $2.25 \times 10^{-4}$ mol per mol of silver chlorobromide. The emulsified dispersion obtained above was mixed with the silver halide emulsion and then an aqueous gelatin solution was added to the mixture so that the composition of the mixture became that shown in Table 22 below to provide coating liquid for Layer 1.

Coating liquids for Layers 2 to 7 were also prepared by almost same manner as above. In addition, each layer further contained 1-oxy-3,5-dichloro-s-triazine sodium salt as a gelatin hardening agent.

Also, the spectral sensitizers used for the emulsion layers were the same as those used in Example 17. Furthermore, the irradiation preventing dye used for the green-sensitive emulsion layer was the same as the dye used in Example 17.

Also, the irradiation preventing dye used for the red-sensitive emulsion layer was as follows.

Irradiation Preventing Dye:

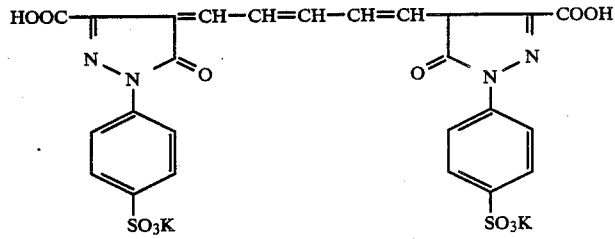

The compositions of the layers were as follows.

| Layer 1: Blue-Sensitive Emulsion Layer | |
| --- | --- |
| Silver Chlorobromide Emulsion (silver bromide 80 mol, grain size 0.76 μm) | 0.27 g/m² as silver |
| Gelatin | 1.10 g/m² |
| Yellow Coupler (a) | $1.08 \times 10^{-3}$ mol/m² |
| Dye Image Stabilizer (b) | 0.19 g/m² |
| Solvent (c) | 0.31 g/m² |
| Layer 2: Color Mixing Preventing Layer | |
| Gelatin | 0.90 g/m² |
| Color Mixing Preventing Agent (d) | $2.33 \times 10^{-4}$ mol/m² |
| Layer 3: Green-Sensitive Emulsion Layer | |
| Silver Chlorobromide Emulsion (silver bromide 85 mol %, grain size 0.50 μm) | 0.11 g/m² as silver |
| Gelatin | 1.56 g/m² |
| Magenta Coupler (e) | $3.38 \times 10^{-4}$ mol/m² |
| Color Image Stabilizer (f) | 0.19 g/m² |
| Solvent (g) | 0.59 g/m² |
| Layer 4: Ultraviolet Absorptive Layer | |
| Gelatin | 1.60 g/m² |
| Ultraviolet Absorbent (h) | $1.70 \times 10^{-4}$ mol/m² |

-continued

| | |
|---|---|
| Color Mixing Preventing Agent (i) | $1.60 \times 10^{-4}$ mol/m$^2$ |
| Solvent (j) | 0.24 g/m$^2$ |
| Layer 5: Red-Sensitive Emulsion Layer | |
| Silver Chlorobromide Emulsion (silver bromide 50 mol %) | 0.22 g/m$^2$ as silver |
| Gelatin | 0.90 g/m$^2$ |
| Cyan Coupler (k) | $7.05 \times 10^{-4}$ mol/m$^2$ |
| Dye Image Stabilizer (l) | $5.20 \times 10^{-4}$ mol/m$^2$ |
| Solvent (m) | 0.22 g/m$^2$ |
| Layer 6: Ultraviolet Absorptive Layer | |

-continued

| | |
|---|---|
| Gelatin | 0.54 g/m$^2$ |
| Ultraviolet Absorbent (h) | $5.10 \times 10^{-4}$ mol/m$^2$ |
| Solvent (j) | 0.08 g/m$^2$ |
| Layer 7: Protective Layer | |
| Gelatin | 1.33 g/m$^2$ |
| Acryl-Modified Copolymer of Polyvinyl Alcohol (modified degree of 17%) | 0.17 g/m$^2$ |

The compounds used for forming the layers were as follows.

Yellow Coupler (a):

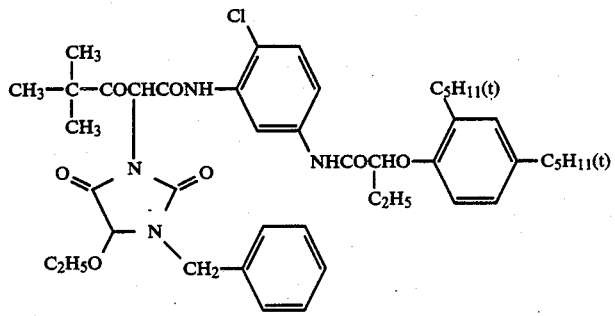

Dye Image Stabilizer (b):

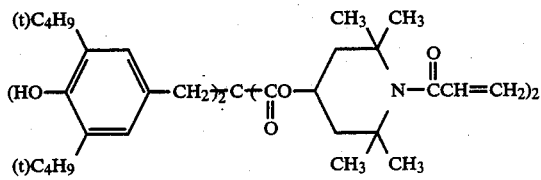

Solvent (c):

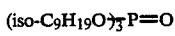

(d)

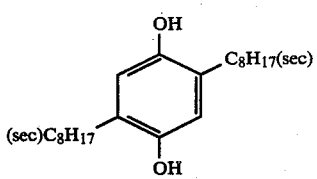

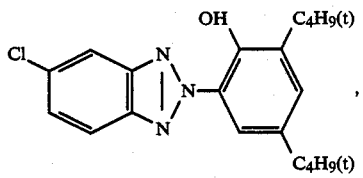

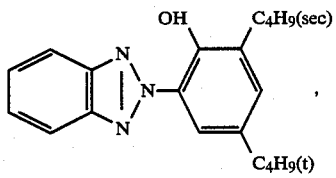

-continued
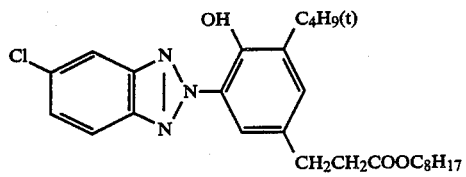
Magenta Coupler (e): (Compound XI-10)
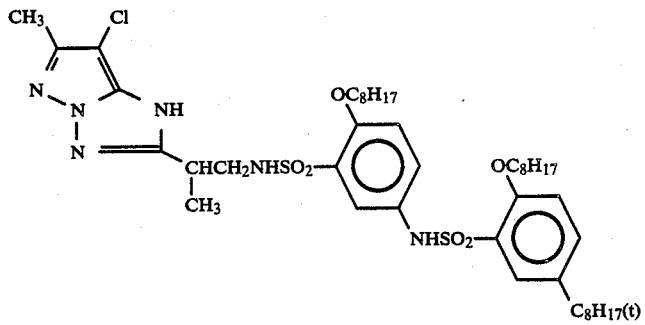
Dye Image Stabilizer (f):
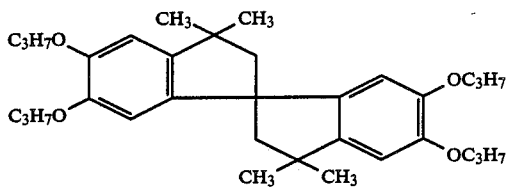
Solvent (g):
A 2:1 (by weight) mixture of $(n\text{-}C_8H_{17}O)_3P=O$ and 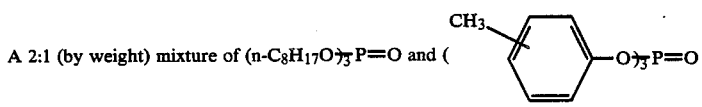
Ultraviolet Absorbent (h):
A 1:5:3 (by mol) mixture of
Color Mixing Preventing Agent (i):
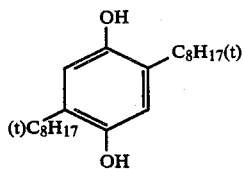
Solvent (j):
$(iso\ C_9H_{19}O)_3P=O$
Cyan Coupler (k):
A 1:1 mixture of
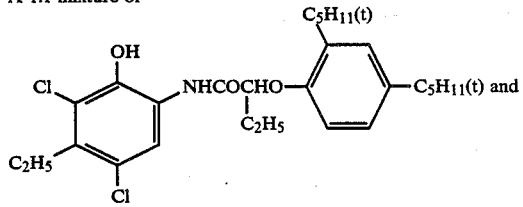 and

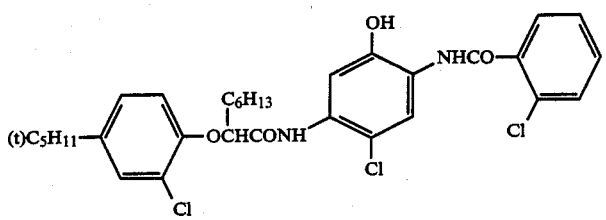

Color Image Stabilizer (l):

A 1:3:3 mixture of

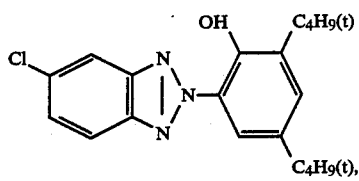

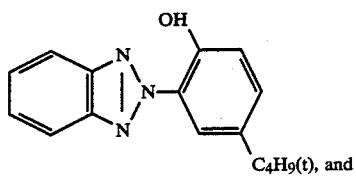

C₄H₉(t), and

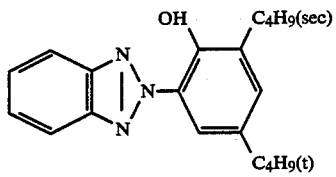

Solvent (m):

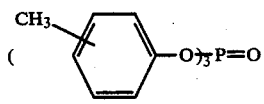

After controlling the balance of the surface tension and viscosity of the coating liquids for Layer 1 to Layer 7 described above, the coating composition were simultaneously coated on the support to provide a multilayer silver halide color photographic material as Sample 601.

Then, by following the same procedure as above except that the silver halide fine grains or the antifoggant as shown in Table 22 below, Samples 602 to 607 were prepared.

Each of the samples was step-exposed for sensitometery using an enlarge (Fuji Color Head 609, made by Fuji Photo Film Co., Ltd.) and processed by the following processing steps. The developer used in the processing is defined as Developer (a).

| Processing Step | | |
|---|---|---|
| Color Development | 33° C. | 3 min. 30 sec. or 7 min. |
| Blix | 33° C. | 1 min. 30 sec. |
| Wash | 25 to 35° C. | |
| Drying | 80° C. | 3 min. |

The compositions of the processing liquids used above were as follows.

| Color Developer: | |
|---|---|
| Nitrilotriacetic Acid.3Na | 2.0 g |
| Benzyl Alcohol | 15 ml |
| Diethylene Glycol | 10 ml |
| Sodium Sulfite | 2.0 g |
| Potassium Bromide | 0.5 g |
| Hydroxylamine Sulfate | 3.0 g |
| 4-Amino-3-methyl-N—ethyl-N—[β-(methane-sulfonamido)ethyl]-p=phenylene diamine Sulfate | 5.0 g |
| Sodium Carbonate (monohydrate) | 30 g |
| Water to make | 1 liter |
| | (pH 10.1) |
| Blix Liquid | |
| Ammonium Thiosulfate (70%) | 150 ml |
| Sodium Sulfite | 15 g |
| Ethylenediaminetetraacetic Acid Iron Ammonium | 55 g |
| Ethylenediaminetetraacetic Acid Di-sodium Salt | 4 g |
| Water to make | 1 liter |
| | (pH 6.9) |

Also, by changing the amounts of the components and

TABLE 22

| Samples No. | | 601 | 602 | 603 | 604 | 605 | 606 | 607 |
|---|---|---|---|---|---|---|---|---|
| Layer 2 | Gelatin g/m² | 0.90 | " | " | " | " | " | " |
| | Color Mixing Preventing Agent (d) mol/m² | 2.33 × 10⁻⁴ | " | " | " | " | " | " |
| | Ag in Fine Grains Silver Halide Emulsion *3 (g/m² as silver) | — | 0.015 | 0.020 | 0.030 | 0.040 | — | — |
| Layer 1 | | Same as Layer in Example 20 | | | | | *1 | *2 |

Samples 601, 606, and 607: Comparion Samples
Samples 602–605: Samples of this Invention
*1: Antifoggant (A) Content: 0.40 mg/m²
*2: Antifoggant (B) Content: 0.50 mg/m²
*3: Particle size of silver bromide: 0.1 μm

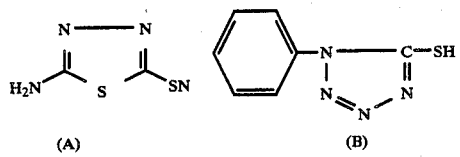

(A)    (B)

TABLE 23

| Samples No. | Developer | Relative Sensitivity | | Fog | | Maximum Color Density | | |
|---|---|---|---|---|---|---|---|---|
| | | 3.5 min. | 7 min. | 3.5 min. | 7 min. | 3.5 min. | 7 min. | |
| 601 | (a) | 100 | 126 | 0.15 | 0.26 | 2.20 | 2.20 | Comparison |
| 602 | " | 97 | 120 | 0.14 | 0.24 | 2.28 | 2.34 | Present Invention |
| 603 | " | 97 | 122 | 0.14 | 0.21 | 2.24 | 2.26 | " |
| 604 | " | 100 | 120 | 0.14 | 0.20 | 2.24 | 2.26 | " |
| 605 | " | 100 | 120 | 0.14 | 0.20 | 2.20 | 2.26 | " |
| 606 | " | 56 | 70 | 0.14 | 0.20 | 2.10 | 2.12 | Comparison |
| 607 | " | 44 | 55 | 0.14 | 0.20 | 2.05 | 2.08 | " |
| 601 | (b) | 93 | 118 | 0.16 | 0.28 | 2.10 | 2.11 | Comparison |
| 602 | " | 90 | 111 | 0.15 | 0.26 | 2.17 | 2.24 | Present Invention |
| 603 | " | 91 | 113 | 0.14 | 0.22 | 2.15 | 2.13 | " |
| 604 | " | 94 | 115 | 0.14 | 0.21 | 2.18 | 2.15 | " |
| 605 | " | 95 | 115 | 0.14 | 0.21 | 2.00 | 2.05 | " |
| 606 | " | 52 | 66 | 0.14 | 0.21 | 2.85 | 1.92 | Comparison |
| 607 | " | 41 | 52 | 0.14 | 0.21 | 1.91 | 1.95 | " |

Relative sensitivity is defined by a relative value with the blue sensitivity of Sample 601 obtained by 3.5 minutes of color development as standard (100).
Fog and Maximum color density are shown on yellow density the pH in Developer as shown below, Developer (b) was prepared.

| Potassium Bromide | 0.4 g |
|---|---|
| Sodium Sulfite | 3.3 g |
| pH (adjusted by the addition of sodium hydroxide) | 10.3 |

The samples were also processed by the above-described processing steps using Developer (b) as the color developer.

The reflection density of each sample thus processed to blue light was measured and the results obtained are shown in Table 23 below.

From the results shown in Table 23 above, it can be seen that by incorporating the silver halide fine grain emulsion in the color mixing preventing agent layer (Layer 2) existing between the green-sensitive emulsion layer (Layer 3) containing the magenta coupler and the blue-sensitive emulsion layer (Layer 1) containing a yellow coupler, the fog density can be reduced. The reduction of fog density was observed in the case of performing the color development for 7 minutes corresponding to the case of performing the development using Developer (a) and in the case of performing the color development for 3 min. 30 sec. and 7 min. corresponding to the case of developing using Developer (b).

Furthermore, in the case of using antifoggant (A) or (B) as Comparison Sample 606 or 607, the sensitivity is reduced at the addition amount thereof for reducing the formation of fog. From this matter, it can be seen that the use of the silver halide fine grain emulsion in this invention is very effective for the reduction of fog of the blue-sensitive emulsion layer.

Also, as an experiment of showing the relation between the silver halide grain size of the blue-sensitive emulsion layer and the silver halide grain size of the green-sensitive emulsion layer, Sample 608 was prepared by following the same procedure as above except that a silver halide emulsion (Cl content 20 mol %, grain size 0.50 μm) was used in place of the silver halide emulsion (Cl content 20 mol %, grain size 0.76 μm) for the blue-sensitive emulsion layer of Sample 601. In addition, the grain size of the silver halide emulsion of the green-sensitive emulsion layer was 0.50 μm. When the sample was exposed in the same way as above and color-developed for 3 min. 30 sec. or 7 min. using Developer (a) or Developer (b), respectively, mixing of magenta was observed at the portions to be colored into yellow.

Thus, it can be seen that when the grain size of the silver halide emulsion of the blue-sensitive emulsion layer is small and and the sensitivity level thereof becomes relatively near the sensitivity level of the silver halide emulsion of the green-sensitive emulsion layer, the color mixing of magenta forms at the portions to be colored into yellow.

While the invention has been described in detail and with reference to specific embodiment thereof, it will be apparent to one skilled in the art that various changes and modifications can be made therein without departing from the spirit and scope thereof.

What is claimed is:

1. A silver halide color photographic material comprising a support having thereon at least one silver halide emulsion layer, said silver halide emulsion layer containing a pyrazoloazole series magenta coupler represented by general formula (I)

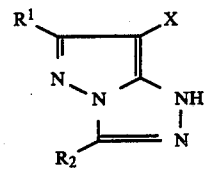

wherein, $R^1$ and $R^2$ each represents a hydrogen atom or a substituent; and X represents a hydrogen atom or a releasing group which is released at the reaction with the oxidation product of an aromatic primary amine developing agent; at least one of said $R^1$ and $R^2$ is an alkyl group having a secondary or tertiary carbon atom directly bonded to the skeleton, at least one of said $R_1$ and $R_2$ is a sulfonamidoalkyl group or a sulfamoylalkyl group; and the magenta coupler may form a dimer or more polymer at the position of said $R^1$, $R^2$ or X, wherein said silver halide emulsion layer contains at least one of the magenta couplers represented by general formula (I) incorporated in the layer as a dispersion in at least one high-boiling point organic solvents represented by following general formula (II), (III), (IV), or (V) and having a dielectric constant of higher than 4.00 (at 25° C. and 10 KHz) and a viscosity of higher than 20 c.p. (at 25° C.):

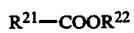    (II)

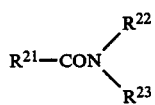    (III)

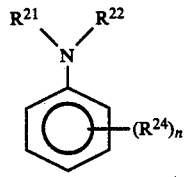    (IV)

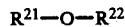    (V)

wherein, $R^{21}$, $R^{22}$ and $R^{23}$ each represents a substituted or unsubstituted alkyl group, a substituted or unsubstituted cycloalkyl group, a substituted or unsubstituted alkenyl group, a substituted or unsubstituted aryl group, or a substituted or unsubstituted heterocyclic group; said $R^{21}$ and $R^{22}$ in general formula (v) may form a condensed ring; $R^{24}$ represents $R^{21}$, $-OR^{21}$ or $-SR^{21}$; and n represents an integer of 1 to 5; when n is 2 or more, $R^{24}$ may be the same or different.

2. The silver halide color photographic material as claimed in claim 1, wherein the ultraviolet absorbent is a compound represented by general formula (VII)

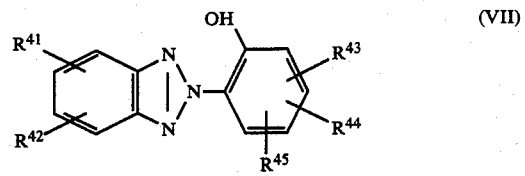

wherein, $R^{41}$, $R^{42}$, $R^{43}$, $R^{44}$, and $R^{45}$ each represents a hydrogen atom, a halogen atom, an alkyl group, a cycloalkyl group, an alkoxy group, an aryl group, an aryloxy group, an alkenyl group, a nitro group or a hydroxy group.

3. The silver halide color photographic material as claimed in claim 1, wherein the ultraviolet absorbent is a compound represented by general formula (VIII)

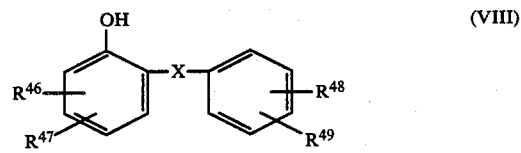

wherein, $R^{46}$, $R^{47}$, $R^{48}$, and $R^{49}$ each represents a hydrogen atom, a halogen atom, a nitro group, a hydroxy group, an alkyl group, an alkoxy group, an aryloxy group, an aryl group or an aryloxy group and X represents $-CO-$ or $-COO-$.

4. The silver halide, color photographic material as claimed in claim 1, wherein the ultraviolet absorbent is a compound represented by general formula (IX)

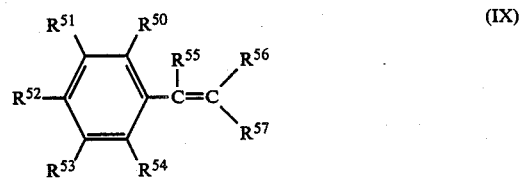

wherein, , $R^{51}$, $R^{52}$, $R^{53}$, and $R^{54}$ each represents a hydrogen atom, a halogen atom, an alkyl group, an aryl group, an alkoxy group, an aryloxy group, an alkylthio group, an arylthio group, an amino group, a hydroxy group, a cyano group, a nitro group, a carbamoyl group, a sulfonyl group, a sulfamoyl group, a sulfonamido group, an acyloxy group, or an oxycarbonyl group; $R^{55}$ represents a hydrogen atom or an alkyl group; $R^{56}$ and $R^{57}$ represent a cyano group, $-COOR^{58}$, $-CONHR^{58}$, $-COR^{58}$ or $-SO_2R^{58}$; and $R^{58}$ represents an alkyl group or an aryl group.

5. A silver halide color photographic material comprising a support having thereon at least one silver halide emulsion layer, said silver halide emulsion layer contains a pyrazoloazole series magenta coupler represented by following general formula (XI) and a water-soluble iridium salt in an amount of $10^{-9}$ to $10^{-3}$ per mole of the silver halide in the emulsion layer;

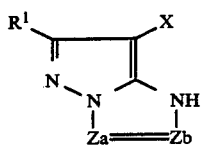

wherein, Za and Zb represent

or =N—; $R^1$ and $R^2$ each represents a hydrogen atom or a substituent; and X represents a hydrogen atom or a group capable of releasing by a coupling reaction with the oxidation product of an aromatic primary amine developing agent; when Za=Zb is a carbon-carbon double bond, it may be a part of an aromatic ring; said coupler may form a dimer or more polymer at the position of said $R^1$, $R^2$ or X; at least one of said $R^1$ and $R^2$ represents a group bonding to the pyrazoloazole nucleus through a secondary or tertiary carbon atom, and $R^1$ or $R^2$ contains at least one —NHSO$_2$—.

6. The silver halide color photographic material as claimed in claim 5, wherein the silver halide emulsion layer further contains a compound represented by general formula (XVII)

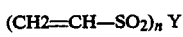

wherein, Y represents a n-valent group and n represents an integer of at least 2.

7. The silver halide color photographic material as claimed in claim 6, wherein the silver halide emulsion layer contains the magenta coupler represented by general formula (XI) and the nitrogen-containing heterocyclic compound represented by general formula (XIV) or (XV).

8. The silver halide color photographic material comprising a support having at least a green-sensitive silver halide emulsion layer containing a pyrazoloazole series magenta coupler represented by following general formula (XI) and at least a blue-sensitive silver halide emulsion layer containing a yellow coupler between the blue-sensitive silver halide emulsion layer and the support, the mean grain size of the silver halide grains (excluding silver halide fine grains shown below) of the blue-sensitive silver halide emulsion layer is at least 1.2 times the mean grain size of the silver halide grains (excluding the silver haldie fine grains) of the green-sensitive silver halide emulsion layer, and further at least one of the blue-sensitive silver halide emulsion, a green-sensitive silver halide emulsion, and a light-insensitive layer existing between the blue-sensitive silver halide emulsion layer and the green-sensitive silver halide emulsion layer contains a silver halide fine grain emulsion,

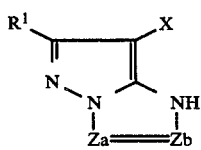

wherein, Za and Zb represent

or =N—; $R^1$ and $R^2$ represent a hydrogen atom or a substituent; and X represents a hydrogen atom or a group capable of releasing by a coupling reaction with the oxidation product of an aromatic primary amine developing agent; when Za=Zb is a carbon-carbon double bond, it may be a part of an aromatic ring; the coupler may form dimer or more polymer at the position of said $R^1$, $R^3$, or X; at least one of said $R^1$ and $R^2$ represents a group bonding to the pyrazoloazole nucleus through a secondary or tertiary carbon and $R^1$ or $R^2$ contains at least one —NHSO$_2$—.

9. A silver halide color photographic material comprising a support having thereon at least one silver halide emulsion layer, said silver halide emulsion layer containing a pyrazoloazole series magenta coupler represented by general formula (I)

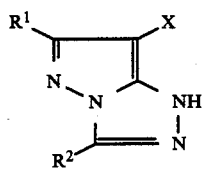

wherein, $R^1$ and $R^2$ each represents a hydrogen atom or a substituent; and X represents a hydrogen atom or a releasing group which is released at the reaction with the oxidation product of an aromatic primary amine developing agent; at least one of said $R^1$ and $R^2$ is an alkyl group having a secondary or tertiary carbon atom directly bonded to the skeleton, at least one of said $R_1$ and $R_2$ is a sulfonamidoalkyl group or a sulfamoylalkyl group; and the magenta coupler may form a dimer or more polymer at the position of said $R^1$, $R^2$ or X, wherein said color photographic material further has a layer containing an ultraviolet absorbent disposed at the opposite side of the support to the silver halide emulsion layer containing the magenta coupler.

10. A silver halide color photographic material comprising a support having thereon at least one silver halide emulsion layer, said silver halide emulsion layer containing a pyrazoloazole series magenta coupler represented by general formula (I)

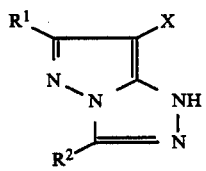

wherein, $R^1$ and $R^2$ each represents a hydrogen atom or a substituent; and X represents a hydrogen atom or a releasing group which is released at the reaction with the oxidation product of an aromatic primary amine developing agent; at least one of said $R^1$ and $R^2$ is an alkyl group having a secondary or tertiary carbon atom directly bonded to the skeleton, at least one of said $R_1$ and $R_2$ is a sulfonamidoalkyl group or a sulfamoylalkyl group; and the magenta coupler may form a dimer or more polymer at the position of said $R^1$, $R^2$ or X, wherein the silver halide emulsion layer contains at least one of (i) an aromatic compound represented by general formula (Xa) below, (ii) an amine compound represented by general formula (Xb) below, and (iii) a metal complex having copper, cobalt, nickel, palladium, or platinum as the center metal and also having at least one organic ligand having two or more conformations;

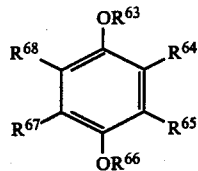
(Xa)

wherein $R^{63}$ represents a hydrogen atom, an alkyl group, an alkenyl group, an aryl group, a heterocyclic group, or

(wherein, $R^{69}$, $R^{70}$, and $R^{71}$, which may be the same or different, each represents an alkyl group, an alkenyl group, an aryl group, an alkoxy group, an alkenoxy group or an aryloxy group); $R^{64}$, $R^{65}$, $R^{66}$, $R^{67}$, and $R^{68}$, which may be the same or different, each represents a hydrogen atom, an alkyl group, an alkenyl group, an aryl group, an acylamino group, an alkylamino group, an alkylthio group, an arylthio group, an alkoxycarbonyl group, an aryloxycarbonyl, a halogen atom, or —O—$R^{63'}$ (wherein, $R^{63'}$ represents the group shown by $R^{63}$); said $R^{63}$ and $R^{64}$ may combine with each other to form a 5-membered ring or a 6-membered ring or a spiro ring; and said $R^{64}$ and $R^{65}$ or said $R^{65}$ and $R^{66}$ amy combine with each other to form a 5-membered ring, a 6-membered ring, or a spiro ring;

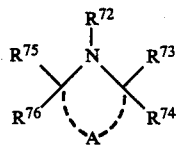
(Xb)

wherein, $R^{72}$ represents a hydrogen atom, an alkyl group, an alkenyl group, an alkinyl group, an acyl group, a sulfonyl group, a sufinyl group, an oxy radical group, or a hydroxy group; $R^{73}$, $R^{74}$, $R^{75}$, and $R^{76}$, which may be the same or different, each represents a hydrogen atom or an alkyl group; and A represents a non-metallic atomic group necessary for forming a 5-membered, 6-membered or 7-membered ring; wherein each of the groups in general formulae (Xa) and (Xb) described above can contain an alkyl group, an aryl group, or a heterocyclic ring as a moiety and can further have a substituent.

11. A silver halide color photographic material comprising a support having thereon at least one silver halide emulsion layer, said emulsion layer contains a pyrazoloazole series magenta coupler represented by following general formula (XI) and at least one of nitrogen-containing heterocyclic compounds represented by following general formula (XII), (XIIIa), (XIIIb), (XIV), (XV), (XVIa) or (XVIb)

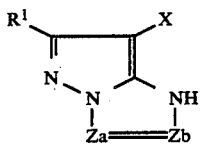
(XI)

wherein, Za and Zb represent

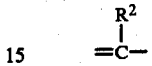

or =N—; $R^1$ and $R^2$ each represents a hydrogen atom or a substituent; and X represents a hydrogen atom or a group capable of releasing by a coupling reaction with the oxidation product of an aromatic primary amine developing agent; when Za=Zb is a carbon-carbon double bond, it may be a part of an aromatic ring; said coupler may form a dimer or more polymer at the position of said $R^1$, $R^2$ or X; at least one of said $R^1$ and $R^2$ represents a group bonding to the pyrazoloazole nucleus through a secondary or tertiary carbon atom; and said $R^1$ or $R^2$ contains at least one —$NHSO_2$—.

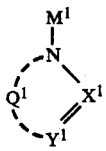
(XII)

wherein, $X^1$ and $Y^1$ represent a carbon atom or a nitrogen atom; $Q^1$ represents an atomic group necessary for forming a 5-membered or 6-membered heterocyclic ring, which may be condensed; and $M^1$ represents a cation;

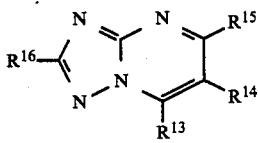
(XIIIa)

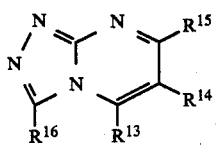
(XIIIb)

wherein $R^{13}$, $R^{14}$, $R^{15}$, and $R^{16}$, which may be the same or different, each represents a hydrogen atom; a substituted or unsubstituted alkyl group, a substituted or unsubstituted aryl group, an amino group; a hydroxyl group; an alkoxy group, an alkylthio group, a substituted or unsubstituted carbamoyl group; a halogen atom; a cyano group; a carboxy group, an alkoxycarbonyl group; or a heterocyclic residue; said $R^{13}$ and $R^{14}$ or said $R^{14}$ and $R^{15}$ may combine with each other to form a 5-membered or 6-membered ring, at least one of said $R^{13}$ and $R^{15}$, however, represents a hydroxy group,

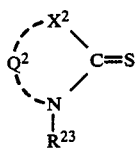
(XIV)

wherein, $R^{23}$ represents a substituted or unsubstituted alkyl group, a substituted or unsubstituted aralkyl group, substituted or unsubstituted alkenyl group, a substituted or unsubstituted aryl group or a substituted or unsubstituted heterocyclic residue; $X^2$ represents O, S, Se or $NR^{24}$ (wherein $R^{24}$, which may be same as or different from $R^{23}$, represents a substituted or unsubstituted alkyl group, a substituted or unsubstituted aralkyl group, a substituted or unsubstituted alkenyl group, a substituted or unsubstituted aryl group, or a substituted or unsubstituted heterocyclic residue); and $Q^2$ represents an atomic group necessary for forming a 5-membered or 6-membered heterocyclic ring, $$Z^1-S-M^2 \quad (XV)$$

wherein, $M^2$ represents a hydrogen atom, a cation, or $-S-Z^1$; and $Z^1$ represents a heterocyclic residue containing at least one nitrogen atom,

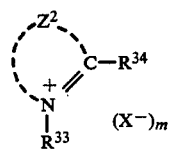
(XVIa)

and

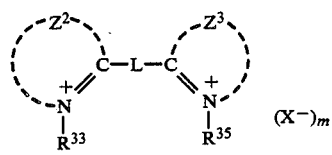
(XVIb)

wherein, $Z^2$ and $Z^3$ each represents an atomic group necessary for forming an imidazole ring, a pyridine ring, a thiazole ring, a selenazole ring, or a combination thereof; $R^{33}$ and $R^{35}$ each represents a substituted or unsubstituted alkyl group, a substituted or unsubstituted alkenyl group, a substituted or unsubstituted aralkyl group, or a substituted or unsubstituted aryl group; $R^{34}$ represents a hydrogen atom or a substituted or unsubstituted alkyl group; said $R^{33}$ and $R^{34}$ may form a ring; L represents a di-valent linkage group; $X'^-$ represents an acid anion; m represents 0 or 1; and n represents 0, 1 or 2.

12. A silver halide color photographic material comprising a support having thereon at least one silver halide emulsion layer, said emulsion layer containing a pyrazoloazole series magenta coupler represented by following general formula (XI-1) or (X-2) and a compound represented by following general formula (XVII),

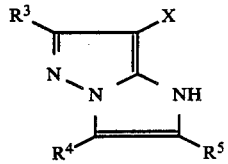
(XI-1)

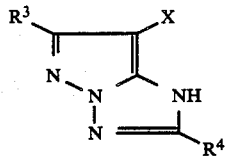
(XI-2)

wherein, X represents a hydrogen atom or a group capable of releasing by a coupling reaction with the oxidation product of an aromatic primary amino developing agent and $R^3$, $R^4$, and $R^5$ each represents a hydrogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycaronylamino group, an aryloxycarbonylamino group, a sulfonamido group, a carbonmoyl group, an acyl group, a sulfamoyl group, a sulfonyl group, a sulfinyl group, an alkoxcarbonyl group, or an aryloxcarbonyl group; at least one of said $R^3$, $R^4$, and $R^5$ represents a group bonding to the pyrazoloazole ring through a secondary or tertiary carbon, and at least one of $R^3$, $R^4$, and $R^5$ is a group having at least one $-NHSO_2-$, $$(CH_2=CH-SO^2)_n Y \quad (XVII)$$

wherein, Y represents a n-valent group and n represents an integer of at least 2.

13. The silver halide color photographic material as claimed in claim 12, wherein the above-described compound represented by general formula (XVII) is a compound represented by following general formula (XvIIa), (XVIIb), or (XVIIc)

$$(CH_2=CH-SO_2)_2 Y^3 \quad (XVIIa)$$

wherein, $Y^3$ represents an alkyl group having 1 to 12 carbon atoms,

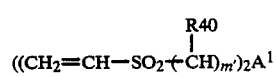
(XVIIb)

wherein, $R^{40}$ represents an hydrogen atom or an alkyl group having at most 3 carbon atoms (said $R^{40}$s may be the same or different); $A^1$ represents a heterocyclic atom; and m' represents an integer of 1 to 4,

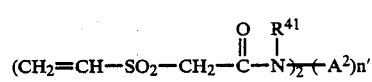
(XVIIc)

wherein, $R^{41}$ represents a hydrogen atom or an alkyl group having 1 to 4 carbon atoms (said $R^{41}$s may be the same or different); $A_2$ represents a divalent group; amd n' represents 0 or 1.

* * * * *